United States Patent
Okamura et al.

(10) Patent No.: US 9,879,083 B2
(45) Date of Patent: Jan. 30, 2018

(54) ANTI-NOTCH3 ANTIBODIES

(71) Applicant: AVEO Pharmaceuticals, Inc., Cambridge, MA (US)

(72) Inventors: Heidi Okamura, Brookline, MA (US); Sandra Abbott, Boston, MA (US); Alisa C. Bell, Bedford, MA (US); Kelly Kreuter, Arvada, CO (US); Ronan O'Hagan, Arlington, MA (US); Samantha Perino, Brighton, MA (US); Hamid Tissire, Abington, MA (US); William M. Winston, Jr., Marlborough, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/653,684

(22) PCT Filed: Dec. 19, 2013

(86) PCT No.: PCT/US2013/076615
§ 371 (c)(1),
(2) Date: Jun. 18, 2015

(87) PCT Pub. No.: WO2014/100435
PCT Pub. Date: Jun. 26, 2014

(65) Prior Publication Data
US 2016/0185852 A1 Jun. 30, 2016

Related U.S. Application Data

(60) Provisional application No. 61/739,435, filed on Dec. 19, 2012, provisional application No. 61/866,787, filed on Aug. 16, 2013.

(51) Int. Cl.
| | | |
|---|---|---|
| *C07K 16/18* | (2006.01) |
| *C07K 16/28* | (2006.01) |
| *A61K 39/395* | (2006.01) |
| *C12N 15/09* | (2006.01) |
| *C12N 15/63* | (2006.01) |
| *C12N 5/10* | (2006.01) |
| *C12N 5/12* | (2006.01) |
| *C12N 5/16* | (2006.01) |
| *C07K 14/705* | (2006.01) |
| *C07K 14/71* | (2006.01) |
| *A61K 39/00* | (2006.01) |

(52) U.S. Cl.
CPC .......... *C07K 16/28* (2013.01); *A61K 39/3955* (2013.01); *C12N 15/09* (2013.01); *C12N 15/63* (2013.01); *A61K 2039/505* (2013.01); *C07K 16/2863* (2013.01); *C07K 2317/14* (2013.01); *C07K 2317/24* (2013.01); *C07K 2317/515* (2013.01); *C07K 2317/56* (2013.01); *C07K 2317/565* (2013.01); *C07K 2317/76* (2013.01); *C07K 2317/92* (2013.01); *C12N 5/10* (2013.01); *C12N 5/12* (2013.01); *C12N 5/16* (2013.01)

(58) Field of Classification Search
CPC ........ A61K 2039/505; A61K 39/39558; A61K 39/3955; A61K 39/395; C07K 2317/76; C07K 16/28; C07K 2317/565; C07K 16/30; C07K 2317/73; C07K 16/2863; C07K 16/18; C07K 2317/24; C07K 2317/56; C07K 14/705; C07K 2316/95
See application file for complete search history.

(56) References Cited

U.S. PATENT DOCUMENTS

| | | | |
|---|---|---|---|
| 7,544,476 B1 | 6/2009 | O'Hagan et al. | |
| 8,425,903 B2 * | 4/2013 | Gurney ................ | C07K 16/462 424/130.1 |
| 2010/0111958 A1 * | 5/2010 | Gurney ................ | C07K 16/462 424/139.1 |
| 2014/0127211 A1 * | 5/2014 | Geles ............... | A61K 47/48438 424/138.1 |

FOREIGN PATENT DOCUMENTS

| | | |
|---|---|---|
| WO | WO-2008/091641 A2 | 7/2008 |
| WO | WO-2010/005566 A2 | 1/2010 |
| WO | WO-2011/041336 A2 | 4/2011 |
| WO | WO-2012/003472 A1 | 1/2012 |
| WO | WO-2014/100435 A1 | 6/2014 |

OTHER PUBLICATIONS

Bellavia et al. Constitutive activation of NF-kB and T-cell leukemia lymphoma in Notch3 transgenic mice. EMBO J 19(13): 3337-3348, 2000.*
Bellavia et al. Combined expression of pTalpha and Notch3 in T cell leukemia identifies the requirement of preTCR for leukemogenesis. Proc Natl Acad Sci USA 99(6): 3788-3793, 2002.*
Bellavia et al. Notch3: from subtle structural differences to functional diversity. Oncogene 27: 5092-5098, 2008.*
Haruki et al. Dominant-negative Notch3 receptor inhibits mitogen-activated protein kinase pathway and the growth of human lung cancers. Cancer Res 65(9): 3555-3561, 2005.*
Joutel et al. Skin biopsy immunostaining with a Notch3 monoclonal antibody for CADASIL diagnosis. Lancet 358: 2049-2051, 2001.*
Park et al. Notch3 gene amplification in ovarian cancer. Cancer Res 66: 6312-6318, 2006.*
Sansone et al. IL-6 triggers malignant features in mammospheres from human ductal breast carcinoma and normal mammary gland (J Clin Invest 117(12): 3988-4002, 2007.*
Aste-Amézaga M et al., (2010), 'Characterization of Notch1 Antibodies that Inhibit Signaling of Both Normal and Mutated Notch1 Receptors,' PLoS One, 5(2):e9094.
Bray SJ, (2006), 'Notch Signalling: A Simple Pathway Becomes Complex,' Nat Rev Mol Cell Biol, 7(9):678-89.

(Continued)

*Primary Examiner* — Bridget E Bunner
(74) *Attorney, Agent, or Firm* — Goodwin Procter LLP

(57) ABSTRACT

Monoclonal antibodies that bind and inhibit activation of human Notch3 are disclosed. The antibodies can be used to treat cell proliferative diseases and disorders, including certain forms of cancer, associated with activation of Notch3.

23 Claims, 18 Drawing Sheets

(56) References Cited

OTHER PUBLICATIONS

International Search Report for Application No. PCT/US2013/076615 (Form ISA/210) dated Aug. 5, 2014 (8 pages).
Kopan R and Ilagan MX, (2009), 'The Canonical Notch Signaling Pathway: Unfolding the Activation Mechanism,' Cell, 137(2):216-33.
Li K et al., (2008), 'Modulation of Notch Signaling by Antibodies Specific for the Extracellular Negative Regulatory Region of Notch3,' J Biol Chem, 283(12):8046-54.
Lin L et al., (2010), 'Targeting Specific Regions of the Notch3 Ligand-Binding Domain Influences Apoptosis and Inhibits Tumor Growth in Lung Cancer,' Cancer Res, 70(2):632-8.
Miele L et al., (2006), 'Notch Signaling as a Novel Cancer Therapeutic Target,' Curr Cancer Drug Targets, 6(4):313-23.
Written Opinion of the International Searching Authority for Application No. PCT/US2013/076615 (Form ISA/237) dated Aug. 5, 2014 (8 pages).
Wu Y et al., (2010), 'Therapeutic Antibody Targeting of Individual Notch Receptors,' Nature, 464(7291):1052-7.

\* cited by examiner

FIG. 2A

Human Notch3 ECD (amino acids 40-1643)

```
                                    40         50         60
                                 A PPCLDGSPCA NGGRCTQLPS
     70         80         90        100        110        120
REAACLCPPG WVGERCQLED PCHSGPCAGR GVCQSSVVAG TARFSCRCPR GFRGPDCSLP
    130        140        150        160        170        180
DPCLSSPCAH GARCSVGPDG RFLCSCPPGY QGRSCRSDVD ECRVGEPCRH GGTCLNTPGS
    190        200        210        220        230        240
FRCQCPAGYT GPLCENPAVP CAPSPCRNGG TCRQSGDLTY DCACLPGFEG QNCEVNVDDC
    250        260        270        280        290        300
PGHRCLNGGT CVDGVNTYNC QCPPEWTGQF CTEDVDECQL QPNACHNGGT CFNTLGGHSC
    310        320        330        340        350        360
VCVNGWTGES CSQNIDDCAT AVCFHGATCH DRVASFYCAC PMGKTGLLCH LDDACVSNPC
    370        380        390        400        410        420
HEDAICDTNP VNGRAICTCP PGFTGGACDQ DVDECSIGAN PCEHLGRCVN TQGSFLCQCG
    430        440        450        460        470        480
RGYTGPRCET DVNECLSGPC RNQATCLDRI GQFTCICMAG FTGTYCEVDI DECQSSPCVN
    490        500        510        520        530        540
GGVCKDRVNG FSCTCPSGFS GSTCQLDVDE CASTPCRNGA KCVDQPDGYE CRCAEGFEGT
    550        560        570        580        590        600
LCDRNVDDCS PDPCHHGRCV DGIASFSCAC APGYTGTRCE SQVDECRSQP CRHGGKCLDL
    610        620        630        640        650        660
VDKYLCRCPS GTTGVNCEVN IDDCASNPCT FGVCRDGINR YDCVCQPGFT GPLCNVEINE
    670        680        690        700        710        720
CASSPCGEGG SCVDGENGFR CLCPPGSLPP LCLPPSHPCA HEPCSHGICY DAPGGFRCVC
    730        740        750        760        770        780
EPGWSGPRCS QSLARDACES QPCRAGGTCS SDGMGFHCTC PPGVQGRQCE LLSPCTPNPC
```

FIG. 2B

```
       790        800        810        820        830        840
EHGGRCESAP GQLPVCSCPQ GWQGPRCQQD VDECAGPAPC GPHGICTNLA GSFSCTCHGG 850        860        870        880        890        900
YTGPSCDQDI NDCDPNPCLN GGSCQDGVGS FSCSCLPGFA GPRCARDVDE CLSNPCGPGT 910        920        930        940        950        960
CTDHVASFTC TCPPGYGGFH CEQDLPDCSP SSCFNGGTCV DGVNSFSCLC RPGYTGAHCQ 970        980        990       1000       1010       1020
HEADPCLSRP CLHGGVCSAA HPGFRCTCLE SFTGPQCQTL VDWCSRQPCQ NGGRCVQTGA 1030       1040       1050       1060       1070       1080
YCLCPPGWSG RLCDIRSLPC REAAAQIGVR LEQLCQAGGQ CVDEDSSHYC VCPEGRTGSH 1090       1100       1110       1120       1130       1140
CEQEVDPCLA QPCQHGGTCR GYMGGYMCEC LPGYNGDNCE DDVDECASQP CQHGGSCIDL 1150       1160       1170       1180       1190       1200
VARYLCSCPP GTLGVLCEIN EDDCGPGPPL DSGPRCLHNG TCVDLVGGFR CTCPPGYTGL 1210       1220       1230       1240       1250       1260
RCEADINECR SGACHAAHTR DCLQDPGGGF RCLCHAGFSG PRCQTVLSPC ESQPCQHGGQ 1270       1280       1290       1300       1310       1320
CRPSPGPGGG LTFTCHCAQP FWGPRCERVA RSCRELQCPV GVPCQQTPRG PRCACPPGLS 1330       1340       1350       1360       1370       1380
GPSCRSFPGS PPGASNASCA AAPCLHGGSC RPAPLAPFFR CACAQGWTGP RCEAPAAAPE 1390       1400       1410       1420       1430       1440
VSEEPRCPRA ACQAKRGDQR CDRECNSPGC GWDGGDCSLS VGDPWRQCEA LQCWRLFNNS 1450       1460       1470       1480       1490       1500
RCDPACSSPA CLYDNFDCHA GGRERTCNPV YEKYCADHFA DGRCDQGCNT EECGWDGLDC 1510       1520       1530       1540       1550       1560
ASEVPALLAR GVLVLTVLLP PEELLRSSAD FLQRLSAILR TSLRFRLDAH GQAMVFPYHR
```

FIG. 2C

```
          1570       1580       1590       1600       1610       1620
     PSPGSEPRAR RELAPEVIGS VVMLEIDNRL CLQSPENDHC FPDAQSAADY LGALSAVERL
          1630       1640
     DFPYPLRDVR GEPLEPPEPS VPL
```

FIG. 3

Human Notch3 EGF-Like Repeats 1-11 (amino acids 40-467)

```
                                        40         50         60
                                         A PPCLDGSPCA NGGRCTQLPS
         70         80         90        100        110        120
REAACLCPPG WVGERCQLED PCHSGPCAGR GVCQSSVVAG TARFSCRCPR GFRGPDCSLP
        130        140        150        160        170        180
DPCLSSPCAH GARCSVGPDG RFLCSCPPGY QGRSCRSDVD ECRVGEPCRH GGTCLNTPGS
        190        200        210        220        230        240
FRCQCPAGYT GPLCENPAVP CAPSPCRNGG TCRQSGDLTY DCACLPGFEG QNCEVNVDDC
        250        260        270        280        290        300
PGHRCLNGGT CVDGVNTYNC QCPPEWTGQF CTEDVDECQL QPNACHNGGT CFNTLGGHSC
        310        320        330        340        350        360
VCVNGWTGES CSQNIDDCAT AVCFHGATCH DRVASFYCAC PMGKTGLLCH LDDACVSNPC
        370        380        390        400        410        420
HEDAICDTNP VNGRAICTCP PGFTGGACDQ DVDECSIGAN PCEHLGRCVN TQGSFLCQCG
        430        440        450        460
RGYTGPRCET DVNECLSGPC RNQATCLDRI GQFTCICMAG FTGTYCE
```

FIG. 7

Complete Heavy Chain Variable Region Amino Acid Alignments

```
                                                                    CDR1
Antibody
                         Ch4F11  EVQLVESGGGLVKPGGSLKLSCAASGFAFS SYDMS WVRQTPEKRLEWVA
                    Sh4F11 Hv3-23  EVQLLESGGGLVQPGGSLRLSCAASGFAFS SYDMS WVRQAPGKGLEWVS
Sh4F11 Hv3-23 A28T S31H T62S       EVQLLESGGGLVQPGGSLRLSCAASGFTFS SHYDMS WVRQAPGKGLEWVS
       Sh4F11 Hv3-23 S31H T62S     EVQLLESGGGLVQPGGSLRLSCAASGFAFS SHYDMS WVRQAPGKGLEWVS
Sh4F11 Hv3-23 A28T S31N T62S       EVQLLESGGGLVQPGGSLRLSCAASGFTFS SNYDMS WVRQAPGKGLEWVS
       Sh4F11 Hv3-23 A28T T62S     EVQLLESGGGLVQPGGSLRLSCAASGFTFS SYDMS WVRQAPGKGLEWVS CDR2
                         Ch4F11  YISRGGGSTYYPDTVKG RFTI
                    Sh4F11 Hv3-23  YISRGGGSTYYPDTVKG RFTI
Sh4F11 Hv3-23 A28T S31H T62S       YISRGGGSTYYPDSVKG RFTI
       Sh4F11 Hv3-23 S31H T62S     YISRGGGSTYYPDSVKG RFTI
Sh4F11 Hv3-23 A28T S31N T62S       YISRGGGSTYYPDSVKG RFTI
       Sh4F11 Hv3-23 A28T T62S     YISRGGGSTYYPDSVKG RFTI CDR3
                         Ch4F11  SRDNAKNTLYLQMSSLKSEDTAMYYCGR HATTAYWYFDV WGAGTTVTVSS  (SEQ ID NO:2)
                    Sh4F11 Hv3-23  SRDNSKNTLYLQMNSLRAEDTAVYYCGR HATTAYWYFDV WGQGTMVTVSS (SEQ ID NO:34)
Sh4F11 Hv3-23 A28T S31H T62S       SRDNSKNTLYLQMNSLRAEDTAVYYCGR HATTAYWYFDV WGQGTMVTVSS (SEQ ID NO:36)
       Sh4F11 Hv3-23 S31H T62S     SRDNSKNTLYLQMNSLRAEDTAVYYCGR HATTAYWYFDV WGQGTMVTVSS (SEQ ID NO:38)
Sh4F11 Hv3-23 A28T S31N T62S       SRDNSKNTLYLQMNSLRAEDTAVYYCGR HATTAYWYFDV WGQGTMVTVSS (SEQ ID NO:40)
       Sh4F11 Hv3-23 A28T T62S     SRDNSKNTLYLQMNSLRAEDTAVYYCGR HATTAYWYFDV WGQGTMVTVSS (SEQ ID NO:42)
```

FIG. 8

Heavy Chain CDR Amino Acid Alignments

| Antibody | CDR1 | | CDR2 | |
|---|---|---|---|---|
| Ch4F11 | SYDMS | (SEQ ID NO:5) | YISRGGSTYYPDTVKG | (SEQ ID NO:6) |
| Sh4F11 Hv3-23 | SYDMS | (SEQ ID NO:5) | YISRGGGSTYYPDTVKG | (SEQ ID NO:6) |
| Sh4F11 Hv3-23 A28T S31H T62S | HYDMS | (SEQ ID NO:51) | YISRGGGSTYYPDSVKG | (SEQ ID NO:53) |
| Sh4F11 Hv3-23 S31H T62S | HYDMS | (SEQ ID NO:51) | YISRGGGSTYYPDSVKG | (SEQ ID NO:53) |
| Sh4F11 Hv3-23 A28T S31N T62S | NYDMS | (SEQ ID NO:52) | YISRGGGSTYYPDSVKG | (SEQ ID NO:53) |
| Sh4F11 Hv3-23 A28T T62S | SYDMS | (SEQ ID NO:5) | YISRGGGSTYYPDSVKG | (SEQ ID NO:53) |

| Antibody | CDR3 | |
|---|---|---|
| Ch4F11 | HATTAYWYFDV | (SEQ ID NO:7) |
| Sh4F11 Hv3-23 | HATTAYWYFDV | (SEQ ID NO:7) |
| Sh4F11 Hv3-23 A28T S31H T62S | HATTAYWYFDV | (SEQ ID NO:7) |
| Sh4F11 Hv3-23 S31H T62S | HATTAYWYFDV | (SEQ ID NO:7) |
| Sh4F11 Hv3-23 A28T S31N T62S | HATTAYWYFDV | (SEQ ID NO:7) |
| Sh4F11 Hv3-23 A28T T62S | HATTAYWYFDV | (SEQ ID NO:7) |

FIG. 9

Complete Light (Kappa) Chain Variable Region Amino Acid Alignments

```
Antibody                    CDR1                                              CDR2
Ch4F11           DVVMTQTPLSLPVSLGDQASISCRSSQSLVHTNGNTYLHWYLQKPGQSPKLLIYKVSNRFSGVPDRFSGS
Hu4F11 Kv2D-29   DVVMTQTPLSLSVTPGQPASISCRSSQSLVHTNGNTYLHWYLQKPGQSPQLLIYKVSNRFSGVPDRFSGS
Hu4F11 Kv2D-29 N28H  DVVMTQTPLSLSVTPGQPASISCRSSQSLVHTHGNTYLHWYLQKPGQSPQLLIYKVSNRFSGVPDRFSGS
Hu4F11 Kv2D-29 N28Q  DVVMTQTPLSLSVTPGQPASISCRSSQSLVHTQGNTYLHWYLQKPGQSPQLLIYKVSNRFSGVPDRFSGS
Hu4F11 Kv2D-29 N28Y  DVVMTQTPLSLSVTPGQPASISCRSSQSLVHTYGNTYLHWYLQKFGQSPQLLIYKVSNRFSGVPDRFSGS CDR3
Ch4F11           GSGTDFTLKISRVEAEDLGVYFCSQSTHVPWTFGGGTKLEIK    (SEQ ID NO:4)
Hu4F11 Kv2D-29   GSGTDFTLKISRVEAEDVGVYFCSQSTHVPWTFGQGTKVEIK    (SEQ ID NO:44)
Hu4F11 Kv2D-29 N28H  GSGTDFTLKISRVEAEDVGVYFCSQSTHVPWTFGQGTKVEIK    (SEQ ID NO:46)
Hu4F11 Kv2D-29 N28Q  GSGTDFTLKISRVEAEDVGVYFCSQSTHVPWTFGQGTKVEIK    (SEQ ID NO:48)
Hu4F11 Kv2D-29 N28Y  GSGTDFTLKISRVEAEDVGVYFCSQSTHVPWTFGQGTKVEIK    (SEQ ID NO:50)
```

FIG. 10

Light (Kappa) Chain CDR Amino Acid Alignments

| Antibody | CDR1 | CDR2 |
|---|---|---|
| CH4F11 | RSSQSLVHTNGNTYLH (SEQ ID NO:8) | KVSNRFS (SEQ ID NO:9) |
| Hu4F11 Kv2D-29 | RSSQSLVHTNGNTYLH (SEQ ID NO:8) | KVSNRFS (SEQ ID NO:9) |
| Hu4F11 Kv2D-29 N28H | RSSQSLVHTHGNTYLH (SEQ ID NO:62) | KVSNRFS (SEQ ID NO:9) |
| Hu4F11 Kv2D-29 N28Q | RSSQSLVHTQGNTYLH (SEQ ID NO:63) | KVSNRFS (SEQ ID NO:9) |
| Hu4F11 Kv2D-29 N28Y | RSSQSLVHTYGNTYLH (SEQ ID NO:64) | KVSNRFS (SEQ ID NO:9) |

| Antibody | CDR3 |
|---|---|
| CH4F11 | SQSTHVPWT (SEQ ID NO:10) |
| Hu4F11 Kv2D-29 | SQSTHVPWT (SEQ ID NO:10) |
| Hu4F11 Kv2D-29 N28H | SQSTHVPWT (SEQ ID NO:10) |
| Hu4F11 Kv2D-29 N28Q | SQSTHVPWT (SEQ ID NO:10) |
| Hu4F11 Kv2D-29 N28Y | SQSTHVPWT (SEQ ID NO:10) | ns

SEQUENCE LISTING

```
<160> NUMBER OF SEQ ID NOS: 96

<210> SEQ ID NO 1
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
gaagtgcagc tggtggagtc tgggggaggc ttagtgaagc ctggagggtc cctgaaactc      60
tcctgtgcag cctctggatt cgctttcagt agctatgaca tgtcttgggt tcgccagact     120
ccggagaaga ggctggagtg ggtcgcatac attagtcgtg gtggtggtag cacctactat     180
ccagacactg tgaagggccg attcaccatc tccagagaca atgccaagaa caccctgtac     240
ctgcaaatga gcagtctgaa gtctgaggac acagccatgt attactgtgg aagacatgct     300
actacggcct actggtactt cgatgtctgg ggcgcaggga ccacggtcac cgtctcctca     360

<210> SEQ ID NO 2
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Arg Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg His Ala Thr Thr Ala Tyr Trp Tyr Phe Asp Val Trp Gly Ala
            100                 105                 110

Gly Thr Thr Val Thr Val Ser Ser
        115                 120

<210> SEQ ID NO 3
<211> LENGTH: 336
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
gatgttgtga tgacccaaac tccactctcc ctgcctgtca gtcttggaga tcaagcctcc    60
atctcttgca gatctagtca gagccttgta cacactaatg caacaccta tttacattgg   120 tacctgcaga agccaggcca gtctccaaaa ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttccg   300
tggacgttcg gtggaggcac caagctggaa atcaaa                             336
```

<210> SEQ ID NO 4
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

```
Ser Tyr Asp Met Ser
1               5
```

<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 6

Tyr Ile Ser Arg Gly Gly Gly Ser Thr Tyr Tyr Pro Asp Thr Val Lys
1               5                   10                  15

Gly

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

His Ala Thr Thr Ala Tyr Trp Tyr Phe Asp Val
1               5                   10

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ser Ser Gln Ser Leu Val His Thr Asn Gly Asn Thr Tyr Leu His
1               5                   10                  15

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Gln Ser Thr His Val Pro Trp Thr
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11
```

Gly Phe Ala Phe Ser Ser Tyr
1               5

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Arg Gly Gly Gly Ser
1               5

<210> SEQ ID NO 13
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
ctaatacgac tcactatagg gcaagcagtg gtatcaacgc agagt            45

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Phe Ala Phe Ser Ser Tyr Asp
1               5

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ile Ser Arg Gly Gly Gly Ser Thr
1               5

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Arg His Ala Thr Thr Ala Tyr Trp Tyr Phe Asp Val
1               5                   10

<210> SEQ ID NO 17

-continued

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ctaatacgac tcactatagg gc                                              22

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
tatgcaaggc ttacaaccac a                                               21

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
cgactgaggc acctccagat gtt                                             23

<210> SEQ ID NO 20
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Ser Leu Val His Thr Asn Gly Asn Thr Tyr
1               5                   10

<210> SEQ ID NO 21
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
gtaaaacgac ggccagt                                                    17

<210> SEQ ID NO 22
<211> LENGTH: 972
<212> TYPE: DNA
<213> ORGANISM: Mus sp.

<400> SEQUENCE: 22
gccaaaacga caccccatc tgtctatcca ctggcccctg atctgctgc ccaaactaac       60
```

```
tccatggtga ccctgggatg cctggtcaag ggctatttcc ctgagccagt gacagtgacc      120
tggaactctg gatccctgtc cagcggtgtg cacaccttcc cagctgtcct gcagtctgac      180
ctctacactc tgagcagctc agtgactgtc ccctccagca cctggcccag cgagaccgtc      240
acctgcaacg ttgcccaccc ggccagcagc accaaggtgg acaagaaaat tgtgcccagg      300
gattgtggtt gtaagccttg catatgtaca gtcccagaag tatcatctgt cttcatcttc      360
cccccaaagc ccaaggatgt gctcaccatt actctgactc ctaaggtcac gtgtgttgtg      420
gtagacatca gcaaggatga tcccgaggtc cagttcagct ggtttgtaga tgatgtggag      480
gtgcacacag ctcagacgca accccgggag gagcagttca acagcacttt ccgctcagtc      540
agtgaacttc ccatcatgca ccaggactgg ctcaatggca aggagttcaa atgcagggtc      600
aacagtgcag ctttccctgc ccccatcgag aaaaccatct ccaaaaccaa aggcagaccg      660
aaggctccac aggtgtacac cattccacct cccaaggagc agatggccaa ggataaagtc      720
agtctgacct gcatgataac agacttcttc cctgaagaca ttactgtgga gtggcagtgg      780
aatgggcagc cagcggagaa ctacaagaac actcagccca tcatggacac agatggctct      840
tacttcgtct acagcaagct caatgtgcag aagagcaact gggaggcagg aaatactttc      900
acctgctctg tgttacatga gggcctgcac aaccaccata ctgagaagag cctctcccac      960
tctcctggta aa                                                         972
```

```
<210> SEQ ID NO 23
<211> LENGTH: 324
<212> TYPE: PRT
<213> ORGANISM: Mus sp.

<400> SEQUENCE: 23

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205
```

```
Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys
```

<210> SEQ ID NO 24
<211> LENGTH: 321
<212> TYPE: DNA
<213> ORGANISM: Mus sp.

<400> SEQUENCE: 24

```
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga acagttggac tgatcaggac     180
agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg t                                              321
```

<210> SEQ ID NO 25
<211> LENGTH: 107
<212> TYPE: PRT
<213> ORGANISM: Mus sp.

<400> SEQUENCE: 25

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 26
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 26

```
gaagtgcagc tggtggagtc tgggggaggc ttagtgaagc ctggagggtc cctgaaactc      60
tcctgtgcag cctctggatt cgctttcagt agctatgaca tgtcttgggt tcgccagact     120
ccggagaaga ggctggagtg ggtcgcatac attagtcgtg gtggtggtag cacctactat     180
ccagacactg tgaagggccg attcaccatc tccagagaca tgccaagaa caccctgtac     240
ctgcaaatga gcagtctgaa gtctgaggac acagccatgt attactgtgg aagacatgct     300
actacggcct actggtactt cgatgtctgg ggcgcaggga ccacggtcac cgtctcctca     360
gccaaaacga cacccccatc tgtctatcca ctggcccctg gatctgctgc ccaaactaac     420
tccatggtga cccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
gattgtggtt gtaagccttg catatgtaca gtcccagaag tatcatctgt cttcatcttc     720
cccccaaagc ccaaggatgt gctcaccatt actctgactc ctaaggtcac gtgtgttgtg     780
gtagacatca gcaaggatga tcccgaggtc cagttcagct ggtttgtaga tgatgtggag     840
gtgcacacag ctcagacgca accccgggag gagcagttca acagcacttt ccgctcagtc     900
agtgaacttc ccatcatgca ccaggactgg ctcaatggca aggagttcaa atgcagggtc     960
aacagtgcag ctttccctgc ccccatcgag aaaaccatct ccaaaaccaa aggcagaccg    1020
aaggctccac aggtgtacac cattccacct cccaaggagc agatggccaa ggataaagtc    1080
agtctgacct gcatgataac agacttcttc cctgaagaca ttactgtgga gtggcagtgg    1140
aatgggcagc cagcggagaa ctacaagaac actcagccca tcatggacac agatggctct    1200
tacttcgtct acagcaagct caatgtgcag aagagcaact gggaggcagg aaatactttc    1260
acctgctctg tgttacatga gggcctgcac aaccaccata ctgagaagag cctctcccac    1320
tctcctggta aa                                                        1332
```

<210> SEQ ID NO 27
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 27

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Arg Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
```

```
                    85                  90                  95
Gly Arg His Ala Thr Ala Tyr Trp Tyr Phe Asp Val Trp Gly Ala
                100                 105                 110
Gly Thr Thr Val Thr Val Ser Ser Ala Lys Thr Thr Pro Pro Ser Val
                115                 120                 125
Tyr Pro Leu Ala Pro Gly Ser Ala Ala Gln Thr Asn Ser Met Val Thr
130             135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Ser Val Thr Val Pro Ser
                180                 185                 190
Ser Thr Trp Pro Ser Glu Thr Val Thr Cys Asn Val Ala His Pro Ala
                195                 200                 205
Ser Ser Thr Lys Val Asp Lys Lys Ile Val Pro Arg Asp Cys Gly Cys
                210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
                245                 250                 255
Thr Cys Val Val Val Asp Ile Ser Lys Asp Asp Pro Glu Val Gln Phe
                260                 265                 270
Ser Trp Phe Val Asp Asp Val Glu Val His Thr Ala Gln Thr Gln Pro
                275                 280                 285
Arg Glu Glu Gln Phe Asn Ser Thr Phe Arg Ser Val Ser Glu Leu Pro
                290                 295                 300
Ile Met His Gln Asp Trp Leu Asn Gly Lys Glu Phe Lys Cys Arg Val
305                 310                 315                 320
Asn Ser Ala Ala Phe Pro Ala Pro Ile Glu Lys Thr Ile Ser Lys Thr
                325                 330                 335
Lys Gly Arg Pro Lys Ala Pro Gln Val Tyr Thr Ile Pro Pro Pro Lys
                340                 345                 350
Glu Gln Met Ala Lys Asp Lys Val Ser Leu Thr Cys Met Ile Thr Asp
                355                 360                 365
Phe Phe Pro Glu Asp Ile Thr Val Glu Trp Gln Trp Asn Gly Gln Pro
                370                 375                 380
Ala Glu Asn Tyr Lys Asn Thr Gln Pro Ile Met Asp Thr Asp Gly Ser
385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
                420                 425                 430
His Thr Glu Lys Ser Leu Ser His Ser Pro Gly Lys
                435                 440

<210> SEQ ID NO 28
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
```

```
gatgttgtga tgacccaaac tccactctcc ctgcctgtca gtcttggaga tcaagcctcc    60
atctcttgca gatctagtca gagccttgta cacactaatg caacaccta tttacattgg   120
tacctgcaga agccaggcca gtctccaaaa ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttccg   300
tggacgttcg gtggaggcac caagctggaa atcaaacggg ctgatgctgc accaactgta   360
tccatcttcc caccatccag tgagcagtta acatctggag gtgcctcagt cgtgtgcttc   420
ttgaacaact ctaccccaa agacatcaat gtcaagtgga gattgatgg cagtgaacga   480
caaaatggcg tcctgaacag ttggactgat caggacagca agacagcac ctacagcatg   540
agcagcaccc tcacgttgac caaggacgag tatgaacgac ataacagcta cctgtgag   600
gccactcaca agacatcaac ttcacccatt gtcaagagct caacaggaa tgagtgt       657
```

<210> SEQ ID NO 29
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 30

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
caggaaacag ctatgacc                                                     18

<210> SEQ ID NO 31
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
gaggtacagc ttgtcgagtc gggaggagga ttggtaaaac cgggtgggtc actcaaattg       60
tcgtgtgcgg cgtcgggatt tgcgttttcg tcgtatgata tgtcgtgggt gcgccagacg      120
ccggaaaaac gattggaatg ggtcgcgtat atctcccgag ggggaggttc gacatactat      180
cccgacacgg tcaaagggcg cttcacgatt tcacgggaca atgcgaaaaa cacgctttat      240
cttcaaatgt cgtcgttgaa atcggaagat accgcgatgt attactgcgg gaggcatgcg      300
acgacggcgt attggtattt cgatgtgtgg ggagccggaa cgacggtgac ggtgtcgtcg      360

<210> SEQ ID NO 32
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
gacgtggtaa tgacgcagac gccgttgtcc cttcctgtct cgctcggaga tcaggcgtcg       60
atctcgtgta gaagctcgca gtcactcgtc cataccaacg ggaatacata tcttcactgg      120
tatttgcaaa agcccggaca gtcaccgaag ctcttgatct acaaagtatc caatcggttt      180 tcggggtgc ccgaccgatt ctcgggatcg ggttcgggga cggattttac gttgaagatt       240
tcgcgggtgg aagcggagga tctccgtgtc tacttttgtt cgcagtcaac gcatgtcccg      300
tggacgttcg gaggcgggac aaaacttgag atcaag                                336

<210> SEQ ID NO 33
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
gaagtacagt tgttggagtc aggaggaggg ttggtccagc cggdtggatc gttgcggctt       60
tcgtgtgcgg cgtcgggatt cgcgttttca tcgtatgaca tgtcgtgggt gaggcaggca      120
ccggggaaag ggcttgaatg ggtatcgtac atttcgagag ggggaggatc gacgtattac      180
ccggatacgg tgaaaggaag gtttacgatc tcgcgcgaca attcaaagaa tacgctttat      240
```

```
cttcagatga actcgctccg agcggaagat acggcggtat actattgcgg tcgccatgcg    300
acgacggcgt attggtattt cgatgtgtgg ggacaaggga cgatggtcac ggtgtcgtcg    360
```

<210> SEQ ID NO 34
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ser
        115                 120
```

<210> SEQ ID NO 35
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35

```
gaagtacagt tgttggagtc aggaggaggg ttggtccagc cgggtggatc gttgcggctt     60
tcgtgtgcgg cgtcgggatt cacctttca cactatgaca tgtcgtgggt gaggcaggca    120
ccggggaaag ggcttgaatg ggtatcgtac atttcgagag gggaggatc gacgtattac    180 ccggattccg tgaaaggaag gtttacgatc tcgcgcgaca attcaaagaa tacgctttat    240
cttcagatga actcgctccg agcggaagat acggcggtat actattgcgg tcgccatgcg    300
acgacggcgt attggtattt cgatgtgtgg ggacaaggga cgatggtcac ggtgtcgtcg    360
```

<210> SEQ ID NO 36
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser His Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ser
        115                 120

<210> SEQ ID NO 37
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gaagtacagt tgttggagtc aggaggaggg ttggtccagc cggttggatc gttgcggctt      60
tcgtgtgcgg cgtcgggatt cgcgttttca cactatgaca tgtcgtgggt gaggcaggca     120
ccggggaaag ggcttgaatg ggtatcgtac atttcgagag ggggaggatc gacgtattac     180
ccggattccg tgaaaggaag gtttacgatc tcgcgcgaca attcaaagaa tacgctttat     240
cttcagatga actcgctccg agcggaagat acggcggtat actattgcgg tcgccatgcg     300
acgacggcgt attggtattt cgatgtgtgg ggacaaggga cgatggtcac ggtgtcgtcg     360

<210> SEQ ID NO 38
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser His Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ser
        115                 120

<210> SEQ ID NO 39
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gaagtacagt tgttggagtc aggaggaggg ttggtccagc cgggtggatc gttgcggctt      60
tcgtgtgcgg cgtcgggatt cacctttca aactatgaca tgtcgtgggt gaggcaggca     120
ccggggaaag ggcttgaatg ggtatcgtac atttcgagag ggaggatc gacgtattac     180 ccggattccg tgaaggaag gtttacgatc tcgcgcgaca attcaaagaa tacgctttat     240
cttcagatga actcgctccg agcggaagat acggcgtat actattgcgg tcgccatgcg     300
acgacggcgt attggtattt cgatgtgtgg ggacaaggga cgatggtcac ggtgtcgtcg     360

<210> SEQ ID NO 40
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ser
        115                 120

<210> SEQ ID NO 41
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
gaagtacagt tgttggagtc aggaggaggg ttggtccagc cgggtggatc gttgcggctt      60
tcgtgtgcgg cgtcgggatt cacctttca tcgtatgaca tgtcgtgggt gaggcaggca     120

```
ccggggaaag ggcttgaatg ggtatcgtac atttcgagag ggggaggatc gacgtattac    180
ccggattccg tgaaaggaag gtttacgatc tcgcgcgaca attcaaagaa tacgctttat    240
cttcagatga actcgctccg agcggaagat acggcggtat actattgcgg tcgccatgcg    300
acgacggcgt attggtattt cgatgtgtgg ggacaaggga cgatggtcac ggtgtcgtcg    360
```

<210> SEQ ID NO 42
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ser
        115                 120

<210> SEQ ID NO 43
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43

```
gatgtagtca tgacccaaac gccgctttcg ttgtcggtga cgcccggaca gcccgcgtca    60
atctcgtgtc ggtcatcgca gtcgttggta cacacaaacg gtaatacgta tctccattgg    120
tatctccaga agcccggcca gtcgccgcag ctcttgatct acaaagtgag caatcgcttt    180
tcgggggtgc cggatcggtt ctcgggatcg ggtcaggaa cggacttcac gcttaagatt    240
tcgagggtcg aggcggagga tgtcggagtc tactttttgtt cgcagtccac acatgtcccc    300
tggacgtttg ggcagggac gaaggtggaa atcaag                               336
```

<210> SEQ ID NO 44
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

<210> SEQ ID NO 45
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gatgtagtca tgacccaaac gccgctttcg ttgtcggtga cgcccggaca gcccgcgtca    60
atctcgtgtc ggtcatcgca gtcgttggta cacacacacg gtaatacgta tctccattgg   120
tatctccaga agcccggcca gtcgccgcag ctcttgatct acaaagtgag caatcgcttt   180 tcggggggtgc cggatcggtt ctcgggatcg ggtcaggaa cggacttcac gcttaagatt   240
tcgagggtcg aggcggagga tgtcggagtc tacttttgtt cgcagtccac acatgtcccc   300
tggacgtttg gcaggggac gaaggtggaa atcaag                              336

<210> SEQ ID NO 46
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

His Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

<210> SEQ ID NO 47
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
gatgtagtca tgacccaaac gccgctttcg ttgtcggtga cgcccggaca gcccgcgtca      60
atctcgtgtc ggtcatcgca gtcgttggta cacacacaag gtaatacgta tctccattgg     120
tatctccaga agcccggcca gtcgccgcag ctcttgatct acaaagtgag caatcgcttt     180 tcggggggtgc cggatcggtt ctcgggatcg ggtcaggaa cggacttcac gcttaagatt     240
tcgagggtcg aggcggagga tgtcggagtc tactttttgtt cgcagtccac acatgtcccc    300
tggacgtttg ggcagggac gaaggtggaa atcaag                                336
```

<210> SEQ ID NO 48
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Gln Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110
```

<210> SEQ ID NO 49
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49

```
gatgtagtca tgacccaaac gccgctttcg ttgtcggtga cgcccggaca gcccgcgtca      60
atctcgtgtc ggtcatcgca gtcgttggta cacacatacg gtaatacgta tctccattgg    120
tatctccaga agcccggcca gtcgccgcag ctcttgatct acaaagtgag caatcgcttt    180 tcggggggtgc cggatcggtt ctcgggatcg ggtcaggaa cggacttcac gcttaagatt    240
tcgagggtcg aggcggagga tgtcggagtc tactttttgtt cgcagtccac acatgtcccc   300
```
tggacgtttg ggcaggggac gaaggtggaa atcaag                                  336

<210> SEQ ID NO 50
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Tyr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

His Tyr Asp Met Ser
1               5

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asn Tyr Asp Met Ser
1               5

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Ile Ser Arg Gly Gly Gly Ser Thr Tyr Tyr Pro Asp Ser Val Lys
1               5                   10                  15

Gly

<210> SEQ ID NO 54
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Phe Thr Phe Ser His Tyr
1               5

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Phe Ala Phe Ser His Tyr
1               5

<210> SEQ ID NO 56
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Phe Thr Phe Ser Asn Tyr
1               5

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Phe Thr Phe Ser Ser Tyr
1               5

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Phe Thr Phe Ser His Tyr Asp
1               5

```
<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Phe Ala Phe Ser His Tyr Asp
1               5

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Phe Thr Phe Ser Asn Tyr Asp
1               5

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Phe Thr Phe Ser Ser Tyr Asp
1               5

<210> SEQ ID NO 62
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Arg Ser Ser Gln Ser Leu Val His Thr His Gly Asn Thr Tyr Leu His
1               5                   10                  15

<210> SEQ ID NO 63
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Arg Ser Ser Gln Ser Leu Val His Thr Gln Gly Asn Thr Tyr Leu His
1               5                   10                  15

<210> SEQ ID NO 64
<211> LENGTH: 16
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 64

Arg Ser Ser Gln Ser Leu Val His Thr Tyr Gly Asn Thr Tyr Leu His
1               5                   10                  15

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gln Ser Leu Val His Thr His Gly Asn Thr Tyr
1               5                   10

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gln Ser Leu Val His Thr Gln Gly Asn Thr Tyr
1               5                   10

<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gln Ser Leu Val His Thr Tyr Gly Asn Thr Tyr
1               5                   10

<210> SEQ ID NO 68
<211> LENGTH: 990
<212> TYPE: DNA
<213> ORGANISM: Homo sapiens

<400> SEQUENCE: 68
gcctcaacaa aaggaccaag tgtgttccca ctcgccccta gcagcaagag tacatccggg      60
ggcactgcag cactcggctg cctcgtcaag gattattttc cagagccagt aaccgtgagc     120
tggaacagtg gagcactcac ttctggtgtc catactttc ctgctgtcct gcaaagctct      180
ggcctgtact cactcagctc cgtcgtgacc gtgccatctt catctctggg cactcagacc     240
tacatctgta atgtaaacca caagcctagc aatactaagg tcgataagcg ggtggaaccc     300
aagagctgcg acaagactca cacttgtccc ccatgccctg cccctgaact tctgggcggt     360
cccagcgtct ttttgttccc accaaagcct aaagatactc tgatgataag tagaacaccc     420
gaggtgacat gtgttgttgt agacgtttcc cacgaggacc cagaggttaa gttcaactgg     480
```

```
tacgttgatg gagtcgaagt acataatgct aagaccaagc ctagagagga gcagtataat    540
agtacatacc gtgtagtcag tgttctcaca gtgctgcacc aagactggct caacggcaaa    600
gaatacaaat gcaaagtgtc caacaaagca ctcccagccc ctatcgagaa gactattagt    660
aaggcaaagg ggcagcctcg tgaaccacag gtgtacactc tgccacccag tagagaggaa    720
atgacaaaga accaagtctc attgacctgc ctggtgaaag gcttctaccc cagcgacatc    780
gccgttgagt gggagagtaa cggtcagcct gagaacaatt acaagacaac ccccccagtg    840
ctggatagtg acgggtcttt ctttctgtac agtaagctga ctgtggacaa gtcccgctgg    900
cagcagggta acgtcttcag ctgttccgtg atgcacgagg cattgcacaa ccactacacc    960
cagaagtcac tgagcctgag cccagggaag                                     990
```

<210> SEQ ID NO 69
<211> LENGTH: 330
<212> TYPE: PRT
<213> ORGANISM: Homo sapiens

<400> SEQUENCE: 69

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 70
<211> LENGTH: 321
<212> TYPE: DNA
<213> ORGANISM: Homo sapiens

<400> SEQUENCE: 70
cgcacagttg ctgcccccag cgtgttcatt ttcccaccta gcgatgagca gctgaaaagc      60
ggtactgcct ctgtcgtatg cttgctcaac aactttttacc cacgtgaggc taaggtgcag    120
tggaaagtgg ataatgcact tcaatctgga aacagtcaag agtccgtgac agaacaggac    180
agcaaagact caacttattc actctcttcc accctgactc tgtccaaggc agactatgaa    240
aaacacaagg tatacgcctg cgaggttaca caccagggtt tgtctagtcc tgtcaccaag    300
tccttcaata ggggcgaatg t                                               321

<210> SEQ ID NO 71
<211> LENGTH: 321
<212> TYPE: DNA
<213> ORGANISM: Homo sapiens

<400> SEQUENCE: 71
cgcacagttg cagcccccag cgtgttcatt ttcccaccta gcgatgagca gctgaaaagc      60
ggtactgcct ctgtcgtatg cttgctcaac aactttttacc cacgtgaggc taaggtgcag    120
tggaaagtgg ataatgcact tcaatctgga aacagtcaag agtccgtgac agaacaggac    180
agcaaagact caacttattc actctcttcc accctgactc tgtccaaggc agactatgaa    240
aaacacaagg tatacgcctg cgaggttaca caccagggtt tgtctagtcc tgtcaccaag    300
tccttcaata ggggcgaatg t                                               321

<210> SEQ ID NO 72
<211> LENGTH: 107
<212> TYPE: PRT
<213> ORGANISM: Homo sapiens

<400> SEQUENCE: 72

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 73
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

```
gaggtacagc ttgtcgagtc gggaggagga ttggtaaaac cgggtgggtc actcaaattg      60
tcgtgtgcgg cgtcgggatt tgcgttttcg tcgtatgata tgtcgtgggt gcgccagacg     120
ccggaaaaac gattggaatg ggtcgcgtat atctcccgag ggggaggttc gacatactat     180
cccgacacgg tcaaagggcg cttcacgatt tcacgggaca atgcgaaaaa cacgctttat     240
cttcaaatgt cgtcgttgaa atcggaagat accgcgatgt attactgcgg gaggcatgcg     300
acgacggcgt attggtattt cgatgtgtgg ggagccggaa cgacggtgac ggtgtcgtcg     360
gcctcaacaa aaggaccaag tgtgttccca ctcgccccta gcagcaagag tacatccggg     420
ggcactgcag cactcggctg cctcgtcaag gattattttc cagagccagt aaccgtgagc     480
tggaacagtg gagcactcac ttctggtgtc catactttc ctgctgtcct gcaaagctct     540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg cccctgaact tctgggcggt     720
cccagcgtct ttttgttccc accaaagcct aaagatactc tgatgataag tagaacaccc     780
gaggtgacat gtgttgttgt agacgtttcc cacgaggacc cagaggttaa gttcaactgg     840
tacgttgatg gagtcgaagt acataatgct aagaccaagc ctagagagga gcagtataat     900
agtacatacc gtgtagtcag tgttctcaca gtgctgcacc aagactggct caacggcaaa     960
gaatacaaat gcaaagtgtc caacaaagca ctcccagccc ctatcgagaa gactattagt    1020
aaggcaaagg ggcagcctcg tgaaccacag gtgtacactc tgccacccag tagagaggaa    1080
atgacaaaga accaagtctc attgacctgc ctggtgaaag gcttctaccc cagcgacatc    1140
gccgttgagt gggagagtaa cggtcagcct gagaacaatt acaagacaac cccccagtg    1200
ctggatagtg acgggtctttt cttctctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                     1350
```

<210> SEQ ID NO 74
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45
```

```
Ala Tyr Ile Ser Arg Gly Gly Gly Ser Thr Tyr Tyr Pro Asp Thr Val
 50                  55                  60
Lys Gly Arg Phe Thr Ile Ser Arg Asp Asn Ala Lys Asn Thr Leu Tyr
 65                  70                  75                  80
Leu Gln Met Ser Ser Leu Lys Ser Glu Asp Thr Ala Met Tyr Tyr Cys
                 85                  90                  95
Gly Arg His Ala Thr Thr Ala Tyr Trp Tyr Phe Asp Val Trp Gly Ala
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```

-continued

<210> SEQ ID NO 75
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
gaagtacagt tgttggagtc aggaggaggg ttggtccagc cgggtggatc gttgcggctt      60
tcgtgtgcgg cgtcgggatt cgcgttttca tcgtatgaca tgtcgtgggt gaggcaggca     120
ccggggaaag ggcttgaatg ggtatcgtac atttcgagag gggaggatc gacgtattac      180
ccggatacgg tgaaaggaag gtttacgatc tcgcgcgaca attcaaagaa tacgctttat     240
cttcagatga actcgctccg agcggaagat acggcggtat actattgcgg tcgccatgcg     300
acgacggcgt attggtattt cgatgtgtgg ggacaaggga cgatggtcac ggtgtcgtcg     360
gcctcaacaa aaggaccaag tgtgttccca ctcgcccta gcagcaagag tacatccggg      420
ggcactgcag cactcggctg cctcgtcaag gattattttc cagagccagt aaccgtgagc     480
tggaacagtg gagcactcac ttctggtgtc catacttttc ctgctgtcct gcaaagctct     540
ggcctgtact cactcagctc cgtcgtgacc gtgccatctt catctctggg cactcagacc     600
tacatctgta atgtaaacca caagcctagc aatactaagg tcgataagcg ggtggaaccc     660
aagagctgcg acaagactca cacttgtccc ccatgccctg cccctgaact tctgggcggt     720
cccagcgtct ttttgttccc accaaagcct aaagatactc tgatgataag tagaacaccc     780
gaggtgacat gtgttgttgt agacgtttcc cacgaggacc cagaggttaa gttcaactgg     840
tacgttgatg gagtcgaagt acataatgct aagaccaagc ctagagagga gcagtataat     900
agtacatacc gtgtagtcag tgttctcaca gtgctgcacc aagactggct caacggcaaa     960
gaatacaaat gcaaagtgtc caacaaagca ctcccagccc ctatcgagaa gactattagt    1020
aaggcaaagg ggcagcctcg tgaaccacag gtgtacactc tgccacccag tagagaggaa    1080
atgacaaaga accaagtctc attgacctgc ctggtgaaag gcttctaccc cagcgacatc    1140
gccgttgagt gggagagtaa cggtcagcct gagaacaatt acaagacaac ccccccagtg    1200
ctggatagtg acgggtcttt ctttctgtac agtaagctga ctgtggacaa gtcccgctgg    1260
cagcagggta acgtcttcag ctgttccgtg atgcacgagg cattgcacaa ccactacacc    1320
cagaagtcac tgagcctgag cccagggaag                                     1350
```

<210> SEQ ID NO 76
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Thr Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg His Ala Thr Thr Ala Tyr Trp Tyr Phe Asp Val Trp Gly Gln
                100                 105                 110

Gly Thr Met Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 77
```

<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

| | | | | | |
|---|---|---|---|---|---|
| gaagtacagt | tgttggagtc | aggaggaggg | ttggtccagc | cgggtggatc | gttgcggctt | 60 |
| tcgtgtgcgg | cgtcgggatt | cacctttttca | cactatgaca | tgtcgtgggt | gaggcaggca | 120 |
| ccggggaaag | ggcttgaatg | ggtatcgtac | atttcgagag | ggggaggatc | gacgtattac | 180 |
| ccggattccg | tgaaaggaag | gtttacgatc | tcgcgcgaca | attcaaagaa | tacgctttat | 240 |
| cttcagatga | actcgctccg | agcggaagat | acggcggtat | actattgcgg | tcgccatgcg | 300 |
| acgacggcgt | attggtattt | cgatgtgtgg | ggacaaggga | cgatggtcac | ggtgtcgtcg | 360 |
| gcctcaacaa | aaggaccaag | tgtgttccca | ctcgcccta | gcagcaagag | tacatccggg | 420 |
| ggcactgcag | cactcggctg | cctcgtcaag | gattattttc | cagagccagt | aaccgtgagc | 480 |
| tggaacagtg | gagcactcac | ttctggtgtc | catactttc | ctgctgtcct | gcaaagctct | 540 |
| ggcctgtact | cactcagctc | cgtcgtgacc | gtgccatctt | catctctggg | cactcagacc | 600 |
| tacatctgta | atgtaaacca | caagcctagc | aatactaagg | tcgataagcg | ggtggaaccc | 660 |
| aagagctgcg | acaagactca | cacttgtccc | ccatgccctg | ccctgaact | tctgggcggt | 720 |
| cccagcgtct | ttttgttccc | accaaagcct | aaagatactc | tgatgataag | tagaacaccc | 780 |
| gaggtgacat | gtgttgttgt | agacgtttcc | cacgaggacc | cagaggttaa | gttcaactgg | 840 |
| tacgttgatg | gagtcgaagt | acataatgct | aagaccaagc | ctagagagga | gcagtataat | 900 |
| agtcatacc | gtgtagtcag | tgttctcaca | gtgctgcacc | aagactggct | caacggcaaa | 960 |
| gaatacaaat | gcaaagtgtc | caacaaagca | ctcccagccc | ctatcgagaa | gactattagt | 1020 |
| aaggcaaagg | ggcagcctcg | tgaaccacag | gtgtacactc | tgccacccag | tagagaggaa | 1080 |
| atgacaaaga | accaagtctc | attgacctgc | ctggtgaaag | gcttctaccc | cagcgacatc | 1140 |
| gccgttgagt | gggagagtaa | cggtcagcct | gagaacaatt | acaagacaac | cccccccagtg | 1200 |
| ctggatagtg | acgggtctttt | cttttctgtac | agtaagctga | ctgtggacaa | gtcccgctgg | 1260 |
| cagcagggta | acgtcttcag | ctgttccgtg | atgcacgagg | cattgcacaa | ccactacacc | 1320 |
| cagaagtcac | tgagcctgag | cccagggaag | | | | 1350 |

<210> SEQ ID NO 78
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Ser Thr Tyr Tyr Pro Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg His Ala Thr Thr Ala Tyr Trp Tyr Phe Asp Val Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 79
<211> LENGTH: 1350
```

<210> SEQ ID NO 79
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
gaagtacagt tgttggagtc aggaggaggg ttggtccagc cgggtggatc gttgcggctt    60
tcgtgtgcgg cgtcgggatt cgcgttttca cactatgaca tgtcgtgggt gaggcaggca   120
ccggggaaag ggcttgaatg ggtatcgtac atttcgagag ggggaggatc gacgtattac   180
ccggattccg tgaaaggaag gtttacgatc tcgcgcgaca attcaaagaa tacgctttat   240
cttcagatga actcgctccg agcggaagat acggcggtat actattgcgg tcgccatgcg   300
acgacggcgt attggtattt cgatgtgtgg ggacaaggga cgatggtcac ggtgtcgtcg   360
gcctcaacaa aaggaccaag tgtgttccca ctcgccccta gcagcaagag tacatccggg   420
ggcactgcag cactcggctg cctcgtcaag gattattttc cagagccagt aaccgtgagc   480
tggaacagtg gagcactcac ttctggtgtc catacttttc ctgctgtcct gcaaagctct   540
ggcctgtact cactcagctc cgtcgtgacc gtgccatctt catctctggg cactcagacc   600
tacatctgta atgtaaacca caagcctagc aatactaagg tcgataagcg ggtggaaccc   660
aagagctgcg acaagactca cacttgtccc ccatgccctg ccctgaact tctgggcggt   720
cccagcgtct ttttgttccc accaaagcct aaagatactc tgatgataag tagaacaccc   780
gaggtgacat gtgttgttgt agacgtttcc cacgaggacc cagaggttaa gttcaactgg   840
tacgttgatg gagtcgaagt acataatgct aagaccaagc ctagagagga gcagtataat   900
agtacatacc gtgtagtcag tgttctcaca gtgctgcacc aagactggct caacggcaaa   960
gaatacaaat gcaaagtgtc caacaaagca ctcccagccc ctatcgagaa gactattagt  1020
aaggcaaagg ggcagcctcg tgaaccacag gtgtacactc tgccacccag tagagaggaa  1080
atgacaaaga accaagtctc attgacctgc ctggtgaaag gcttctaccc cagcgacatc  1140
gccgttgagt gggagagtaa cggtcagcct gagaacaatt acaagacaac ccccccagtg  1200
ctggatagtg acgggtcttt cttttctgtac agtaagctga ctgtggacaa gtcccgctgg  1260
cagcagggta acgtcttcag ctgttccgtg atgcacgagg cattgcacaa ccactacacc  1320
cagaagtcac tgagcctgag cccagggaag                                    1350
```

<210> SEQ ID NO 80
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser His Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg His Ala Thr Thr Ala Tyr Trp Tyr Phe Asp Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 81
<211> LENGTH: 1350
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81

```
gaagtacagt tgttggagtc aggaggaggg ttggtccagc cgggtggatc gttgcggctt      60
tcgtgtgcgg cgtcgggatt cacctttca aactatgaca tgtcgtgggt gaggcaggca      120
ccggggaaag ggcttgaatg ggtatcgtac atttcgagag ggggaggatc gacgtattac     180
ccggattccg tgaaaggaag gtttacgatc tcgcgcgaca attcaaagaa tacgctttat     240
cttcagatga actcgctccg agcggaagat acggcggtat actattgcgg tcgccatgcg    300
acgacggcgt attggtattt cgatgtgtgg ggacaaggga cgatggtcac ggtgtcgtcg    360
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt    720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac cccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 82
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95
Gly Arg His Ala Thr Thr Ala Tyr Trp Tyr Phe Asp Val Trp Gly Gln
                100                 105                 110
Gly Thr Met Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 83
<211> LENGTH: 1350
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 83

| | | | | | |
|---|---|---|---|---|---|
| gaagtacagt | tgttggagtc | aggaggaggg | ttggtccagc | cgggtggatc | gttgcggctt | 60 |
| tcgtgtgcgg | cgtcgggatt | cacctttca | tcgtatgaca | tgtcgtgggt | gaggcaggca | 120 |
| ccggggaaag | ggcttgaatg | ggtatcgtac | atttcgagag | gggaggatc | gacgtattac | 180 |
| ccggattccg | tgaaaggaag | gtttacgatc | tcgcgcgaca | attcaaagaa | tacgctttat | 240 |
| cttcagatga | actcgctccg | agcggaagat | acggcggtat | actattgcgg | tcgccatgcg | 300 |
| acgacggcgt | attggtattt | cgatgtgtgg | ggacaaggga | cgatggtcac | ggtgtcgtcg | 360 |
| gcctcaacaa | aaggaccaag | tgtgttccca | ctcgccccta | gcagcaagag | tacatccggg | 420 |
| ggcactgcag | cactcggctg | cctcgtcaag | gattattttc | cagagccagt | aaccgtgagc | 480 |
| tggaacagtg | gagcactcac | ttctggtgtc | catactttc | ctgctgtcct | gcaaagctct | 540 |
| ggcctgtact | cactcagctc | cgtcgtgacc | gtgccatctt | catctctggg | cactcagacc | 600 |
| tacatctgta | atgtaaacca | caagcctagc | aatactaagg | tcgataagcg | ggtggaaccc | 660 |
| aagagctgcg | acaagactca | cacttgtccc | ccatgccctg | cccctgaact | tctgggcggt | 720 |
| cccagcgtct | ttttgttccc | accaaagcct | aaagatactc | tgatgataag | tagaacaccc | 780 |
| gaggtgacat | gtgttgttgt | agacgttcc | cacgaggacc | cagaggttaa | gttcaactgg | 840 |
| tacgttgatg | gagtcgaagt | acataatgct | aagaccaagc | ctagagagga | gcagtataat | 900 |
| agtacatacc | gtgtagtcag | tgttctcaca | gtgctgcacc | aagactggct | caacggcaaa | 960 |
| gaatacaaat | gcaaagtgtc | caacaaagca | ctcccagccc | ctatcgagaa | gactattagt | 1020 |
| aaggcaaagg | ggcagcctcg | tgaaccacag | gtgtacactc | tgccacccag | tagagaggaa | 1080 |
| atgacaaaga | accaagtctc | attgacctgc | ctggtgaaag | gcttctaccc | cagcgacatc | 1140 |
| gccgttgagt | gggagagtaa | cggtcagcct | gagaacaatt | acaagacaac | ccccccagtg | 1200 |
| ctggatagtg | acgggtcttt | cttctctgtac | agtaagctga | ctgtggacaa | gtcccgctgg | 1260 |
| cagcagggta | acgtcttcag | ctgttccgtg | atgcacgagg | cattgcacaa | ccactacacc | 1320 |
| cagaagtcac | tgagcctgag | cccagggaag | | | | 1350 |

<210> SEQ ID NO 84
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Tyr Ile Ser Arg Gly Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg His Ala Thr Thr Ala Tyr Trp Tyr Phe Asp Val Trp Gly Gln
            100                 105                 110

Gly Thr Met Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 85
<211> LENGTH: 657
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 85
gacgtggtaa tgacgcagac gccgttgtcc cttcctgtct cgctcggaga tcaggcgtcg    60
atctcgtgta gaagctcgca gtcactcgtc cataccaacg ggaatacata tcttcactgg   120
tatttgcaaa agcccggaca gtcaccgaag ctcttgatct acaaagtatc caatcggttt   180 tcggggtgc ccgaccgatt ctcgggatcg ggttcgggga cggattttac gttgaagatt    240
tcgcgggtgg aagcggagga tctcggtgtc tactttttgtt cgcagtcaac gcatgtcccg   300
tggacgttcg gaggcgggac aaaacttgag atcaagcgca cagttgctgc ccccagcgtg   360
ttcattttcc cacctagcga tgagcagctg aaaagcggta ctgcctctgt cgtatgcttg    420
ctcaacaact tttacccacg tgaggctaag gtgcagtgga agtggataa tgcacttcaa    480 tctggaaaca gtcaagagtc cgtgacagaa caggacagca aagactcaac ttattcactc    540
tcttccaccc tgactctgtc caaggcagac tatgaaaaac acaaggtata cgcctgcgag   600
gttacacacc agggtttgtc tagtcctgtc accaagtcct tcaataggg cgaatgt       657

<210> SEQ ID NO 86
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 87
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
gatgtagtca tgacccaaac gccgctttcg ttgtcggtga cgcccggaca gcccgcgtca      60
atctcgtgtc ggtcatcgca gtcgttggta cacacaaacg gtaatacgta tctccattgg     120
tatctccaga agcccggcca gtcgccgcag ctcttgatct acaaagtgag caatcgcttt     180 tcggggggtgc cggatcggtt ctcgggatcg gggtcaggaa cggacttcac gcttaagatt     240 tcgaggggtcg aggcggagga tgtcggagtc tactttttgtt cgcagtccac acatgtcccc    300
tggacgtttg ggcaggggac gaaggtggaa atcaagcgca cagttgctgc ccccagcgtg     360
ttcattttcc cacctagcga tgagcagctg aaaagcggta ctgcctctgt cgtatgcttg     420
ctcaacaact tttacccacg tgaggctaag gtgcagtgga aagtggataa tgcacttcaa     480
tctggaaaca gtcaagagtc cgtgacagaa caggacagca aagactcaac ttattcactc     540
tcttccaccc tgactctgtc caaggcagac tatgaaaaac acaaggtata cgcctgcgag     600
gttacacacc agggtttgtc tagtcctgtc accaagtcct tcaataggggg cgaatgt       657

<210> SEQ ID NO 88
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
210                 215
```

<210> SEQ ID NO 89
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89

```
gatgtagtca tgacccaaac gccgctttcg ttgtcggtga cgcccggaca gcccgcgtca    60
atctcgtgtc ggtcatcgca gtcgttggta cacacacacg gtaatacgta tctccattgg   120
tatctccaga agcccggcca gtcgccgcag ctcttgatct acaaagtgag caatcgcttt   180
tcggggggtgc cggatcggtt ctcgggatcg gggtcaggaa cggacttcac gcttaagatt   240
tcgagggtcg aggcggagga tgtcggagtc tactttttgtt cgcagtccac acatgtcccc   300
tggacgtttg ggcaggggac gaaggtggaa atcaagcgca cagttgcagc ccccagcgtg    360
ttcattttcc cacctagcga tgagcagctg aaaagcggta ctgcctctgt cgtatgcttg    420
ctcaacaact tttacccacg tgaggctaag gtgcagtgga aagtggataa tgcacttcaa    480
tctggaaaca gtcaagagtc cgtgacagaa caggacagca aagactcaac ttattcactc    540
tcttccaccc tgactctgtc caaggcagac tatgaaaaac acaaggtata cgcctgcgag    600
gttacacacc agggtttgtc tagtcctgtc accaagtcct tcaataggggg cgaatgt     657
```

<210> SEQ ID NO 90
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Asp Val Val Met Thr Gln Thr Pro Leu Ser Leu Ser Val Thr Pro Gly
1               5                  10                  15

Gln Pro Ala Ser Ile Ser Cys Arg Ser Ser Gln Ser Leu Val His Thr
            20                  25                  30

His Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110
```

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 91
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
gatgtagtca tgacccaaac gccgctttcg ttgtcggtga cgcccggaca gcccgcgtca     60
atctcgtgtc ggtcatcgca gtcgttggta cacacacaag gtaatacgta tctccattgg   120
tatctccaga agcccggcca gtcgccgcag ctcttgatct acaaagtgag caatcgcttt   180 tcggggggtgc cggatcggtt ctcgggatcg ggtcaggaa cggacttcac gcttaagatt   240
tcgagggtcg aggcggagga tgtcggagtc tactttttgtt cgcagtccac acatgtcccc   300
tggacgtttg ggcaggggac gaaggtggaa atcaagcgca cagttgcagc cccagcgtg    360 ttcattttcc cacctagcga tgagcagctg aaaagcggta ctgcctctgt cgtatgcttg   420
ctcaacaact tttacccacg tgaggctaag gtgcagtgga agtggataa tgcacttcaa    480 tctgaaaaca gtcaagagtc cgtgacagaa caggacagca agactcaac ttattcactc    540 tcttccaccc tgactctgtc caaggcagac tatgaaaaac acaaggtata cgcctgcgag   600
gttacacacc agggttttgtc tagtcctgtc accaagtcct tcaataggg cgaatgt       657
```

```
<210> SEQ ID NO 92
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Thr
            20                  25                  30

Gln Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 93
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93

```
gatgtagtca tgacccaaac gccgctttcg ttgtcggtga cgcccggaca gcccgcgtca    60
atctcgtgtc ggtcatcgca gtcgttggta cacacatacg gtaatacgta tctccattgg   120
tatctccaga agcccggcca gtcgccgcag ctcttgatct acaaagtgag caatcgcttt   180
tcggggtgc cggatcggtt ctcgggatcg ggtcaggaa cggacttcac gcttaagatt   240
tcgagggtcg aggcggagga tgtcggagtc tacttttgtt cgcagtccac acatgtcccc   300
tggacgtttg gcaggggac gaaggtggaa atcaagcgca cagttgcagc ccccagcgtg   360
ttcattttcc cacctagcga tgagcagctg aaaagcggta ctgcctctgt cgtatgcttg   420
ctcaacaact tttacccacg tgaggctaag gtgcagtgga agtggataa tgcacttcaa   480
tctggaaaca gtcaagagtc cgtgacagaa caggacagca aagactcaac ttattcactc   540
tcttccaccc tgactctgtc caaggcagac tatgaaaaac acaaggtata cgcctgcgag   600
gttacacacc agggtttgtc tagtcctgtc accaagtcct tcaatagggg cgaatgt      657
```

<210> SEQ ID NO 94
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
Asp Val Val Met Thr Gln Thr Pro Leu Ser Leu Ser Val Thr Pro Gly
  1               5                  10                  15
```

```
Gln Pro Ala Ser Ile Ser Cys Arg Ser Ser Gln Ser Leu Val His Thr
            20                  25                  30

Tyr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 95
<211> LENGTH: 1604
<212> TYPE: PRT
<213> ORGANISM: Homo sapiens

<400> SEQUENCE: 95

Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
            20                  25                  30

Val Gly Glu Arg Cys Gln Leu Glu Asp Pro Cys His Ser Gly Pro Cys
        35                  40                  45

Ala Gly Arg Gly Val Cys Gln Ser Ser Val Val Ala Gly Thr Ala Arg
    50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95

Val Gly Pro Asp Gly Arg Phe Leu Cys Ser Cys Pro Pro Gly Tyr Gln
            100                 105                 110

Gly Arg Ser Cys Arg Ser Asp Val Asp Glu Cys Arg Val Gly Glu Pro
        115                 120                 125

Cys Arg His Gly Gly Thr Cys Leu Asn Thr Pro Gly Ser Phe Arg Cys
    130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
                165                 170                 175
```

-continued

Gly Asp Leu Thr Tyr Asp Cys Ala Cys Leu Pro Gly Phe Glu Gly Gln
            180                 185                 190

Asn Cys Glu Val Asn Val Asp Cys Pro Gly His Arg Cys Leu Asn
        195                 200                 205

Gly Gly Thr Cys Val Asp Gly Val Asn Thr Tyr Asn Cys Gln Cys Pro
        210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
                245                 250                 255

Gly Gly His Ser Cys Val Cys Val Asn Gly Trp Thr Gly Glu Ser Cys
            260                 265                 270

Ser Gln Asn Ile Asp Asp Cys Ala Thr Ala Val Cys Phe His Gly Ala
        275                 280                 285

Thr Cys His Asp Arg Val Ala Ser Phe Tyr Cys Ala Cys Pro Met Gly
        290                 295                 300

Lys Thr Gly Leu Leu Cys His Leu Asp Asp Ala Cys Val Ser Asn Pro
305                 310                 315                 320

Cys His Glu Asp Ala Ile Cys Asp Thr Asn Pro Val Asn Gly Arg Ala
                325                 330                 335

Ile Cys Thr Cys Pro Pro Gly Phe Thr Gly Gly Ala Cys Asp Gln Asp
            340                 345                 350

Val Asp Glu Cys Ser Ile Gly Ala Asn Pro Cys Glu His Leu Gly Arg
        355                 360                 365

Cys Val Asn Thr Gln Gly Ser Phe Leu Cys Gln Cys Gly Arg Gly Tyr
        370                 375                 380

Thr Gly Pro Arg Cys Glu Thr Asp Val Asn Glu Cys Leu Ser Gly Pro
385                 390                 395                 400

Cys Arg Asn Gln Ala Thr Cys Leu Asp Arg Ile Gly Gln Phe Thr Cys
                405                 410                 415

Ile Cys Met Ala Gly Phe Thr Gly Thr Tyr Cys Glu Val Asp Ile Asp
            420                 425                 430

Glu Cys Gln Ser Ser Pro Cys Val Asn Gly Gly Val Cys Lys Asp Arg
        435                 440                 445

Val Asn Gly Phe Ser Cys Thr Cys Pro Ser Gly Phe Ser Gly Ser Thr
        450                 455                 460

Cys Gln Leu Asp Val Asp Glu Cys Ala Ser Thr Pro Cys Arg Asn Gly
465                 470                 475                 480

Ala Lys Cys Val Asp Gln Pro Asp Gly Tyr Glu Cys Arg Cys Ala Glu
                485                 490                 495

Gly Phe Glu Gly Thr Leu Cys Asp Arg Asn Val Asp Cys Ser Pro
            500                 505                 510

Asp Pro Cys His His Gly Arg Cys Val Asp Gly Ile Ala Ser Phe Ser
        515                 520                 525

Cys Ala Cys Ala Pro Gly Tyr Thr Gly Thr Arg Cys Glu Ser Gln Val
        530                 535                 540

Asp Glu Cys Arg Ser Gln Pro Cys Arg His Gly Gly Lys Cys Leu Asp
545                 550                 555                 560

Leu Val Asp Lys Tyr Leu Cys Arg Cys Pro Ser Gly Thr Thr Gly Val
                565                 570                 575

Asn Cys Glu Val Asn Ile Asp Asp Cys Ala Ser Asn Pro Cys Thr Phe
            580                 585                 590

```
Gly Val Cys Arg Asp Gly Ile Asn Arg Tyr Asp Cys Val Cys Gln Pro
                595                 600                 605

Gly Phe Thr Gly Pro Leu Cys Asn Val Glu Ile Asn Glu Cys Ala Ser
        610                 615                 620

Ser Pro Cys Gly Glu Gly Gly Ser Cys Val Asp Gly Glu Asn Gly Phe
625                 630                 635                 640

Arg Cys Leu Cys Pro Gly Ser Leu Pro Leu Cys Leu Pro Pro
                645                 650                 655

Ser His Pro Cys Ala His Glu Pro Cys Ser His Gly Ile Cys Tyr Asp
                660                 665                 670

Ala Pro Gly Gly Phe Arg Cys Val Cys Glu Pro Gly Trp Ser Gly Pro
        675                 680                 685

Arg Cys Ser Gln Ser Leu Ala Arg Asp Ala Cys Glu Ser Gln Pro Cys
        690                 695                 700

Arg Ala Gly Gly Thr Cys Ser Ser Asp Gly Met Gly Phe His Cys Thr
705                 710                 715                 720

Cys Pro Pro Gly Val Gln Gly Arg Gln Cys Glu Leu Leu Ser Pro Cys
                725                 730                 735

Thr Pro Asn Pro Cys Glu His Gly Gly Arg Cys Glu Ser Ala Pro Gly
        740                 745                 750

Gln Leu Pro Val Cys Ser Cys Pro Gln Gly Trp Gln Gly Pro Arg Cys
        755                 760                 765

Gln Gln Asp Val Asp Glu Cys Ala Gly Pro Ala Pro Cys Gly Pro His
        770                 775                 780

Gly Ile Cys Thr Asn Leu Ala Gly Ser Phe Ser Cys Thr Cys His Gly
785                 790                 795                 800

Gly Tyr Thr Gly Pro Ser Cys Asp Gln Asp Ile Asn Asp Cys Asp Pro
                805                 810                 815

Asn Pro Cys Leu Asn Gly Gly Ser Cys Gln Asp Gly Val Gly Ser Phe
        820                 825                 830

Ser Cys Ser Cys Leu Pro Gly Phe Ala Gly Pro Arg Cys Ala Arg Asp
        835                 840                 845

Val Asp Glu Cys Leu Ser Asn Pro Cys Gly Pro Gly Thr Cys Thr Asp
850                 855                 860

His Val Ala Ser Phe Thr Cys Thr Cys Pro Pro Gly Tyr Gly Gly Phe
865                 870                 875                 880

His Cys Glu Gln Asp Leu Pro Asp Cys Ser Pro Ser Cys Phe Asn
                885                 890                 895

Gly Gly Thr Cys Val Asp Gly Val Asn Ser Phe Ser Cys Leu Cys Arg
        900                 905                 910

Pro Gly Tyr Thr Gly Ala His Cys Gln His Glu Ala Asp Pro Cys Leu
        915                 920                 925

Ser Arg Pro Cys Leu His Gly Gly Val Cys Ser Ala Ala His Pro Gly
930                 935                 940

Phe Arg Cys Thr Cys Leu Glu Ser Phe Thr Gly Pro Gln Cys Gln Thr
945                 950                 955                 960

Leu Val Asp Trp Cys Ser Arg Gln Pro Cys Gln Asn Gly Gly Arg Cys
                965                 970                 975

Val Gln Thr Gly Ala Tyr Cys Leu Cys Pro Pro Gly Trp Ser Gly Arg
        980                 985                 990

Leu Cys Asp Ile Arg Ser Leu Pro  Cys Arg Glu Ala Ala  Ala Gln Ile
        995                 1000                1005

Gly Val  Arg Leu Glu Gln Leu  Cys Gln Ala Gly Gly  Gln Cys Val
```

-continued

```
                1010                1015                1020
Asp Glu Asp Ser Ser His Tyr Cys Val Cys Pro Glu Gly Arg Thr
        1025                1030                1035
Gly Ser His Cys Glu Gln Glu Val Asp Pro Cys Leu Ala Gln Pro
        1040                1045                1050
Cys Gln His Gly Gly Thr Cys Arg Gly Tyr Met Gly Gly Tyr Met
        1055                1060                1065
Cys Glu Cys Leu Pro Gly Tyr Asn Gly Asp Asn Cys Glu Asp Asp
        1070                1075                1080
Val Asp Glu Cys Ala Ser Gln Pro Cys Gln His Gly Gly Ser Cys
        1085                1090                1095
Ile Asp Leu Val Ala Arg Tyr Leu Cys Ser Cys Pro Pro Gly Thr
        1100                1105                1110
Leu Gly Val Leu Cys Glu Ile Asn Glu Asp Asp Cys Gly Pro Gly
        1115                1120                1125
Pro Pro Leu Asp Ser Gly Pro Arg Cys Leu His Asn Gly Thr Cys
        1130                1135                1140
Val Asp Leu Val Gly Gly Phe Arg Cys Thr Cys Pro Pro Gly Tyr
        1145                1150                1155
Thr Gly Leu Arg Cys Glu Ala Asp Ile Asn Glu Cys Arg Ser Gly
        1160                1165                1170
Ala Cys His Ala Ala His Thr Arg Asp Cys Leu Gln Asp Pro Gly
        1175                1180                1185
Gly Gly Phe Arg Cys Leu Cys His Ala Gly Phe Ser Gly Pro Arg
        1190                1195                1200
Cys Gln Thr Val Leu Ser Pro Cys Glu Ser Gln Pro Cys Gln His
        1205                1210                1215
Gly Gly Gln Cys Arg Pro Ser Pro Gly Pro Gly Gly Gly Leu Thr
        1220                1225                1230
Phe Thr Cys His Cys Ala Gln Pro Phe Trp Gly Pro Arg Cys Glu
        1235                1240                1245
Arg Val Ala Arg Ser Cys Arg Glu Leu Gln Cys Pro Val Gly Val
        1250                1255                1260
Pro Cys Gln Gln Thr Pro Arg Gly Pro Arg Cys Ala Cys Pro Pro
        1265                1270                1275
Gly Leu Ser Gly Pro Ser Cys Arg Ser Phe Pro Gly Ser Pro Pro
        1280                1285                1290
Gly Ala Ser Asn Ala Ser Cys Ala Ala Ala Pro Cys Leu His Gly
        1295                1300                1305
Gly Ser Cys Arg Pro Ala Pro Leu Ala Pro Phe Phe Arg Cys Ala
        1310                1315                1320
Cys Ala Gln Gly Trp Thr Gly Pro Arg Cys Glu Ala Pro Ala Ala
        1325                1330                1335
Ala Pro Glu Val Ser Glu Glu Pro Arg Cys Pro Arg Ala Ala Cys
        1340                1345                1350
Gln Ala Lys Arg Gly Asp Gln Arg Cys Asp Arg Glu Cys Asn Ser
        1355                1360                1365
Pro Gly Cys Gly Trp Asp Gly Gly Asp Cys Ser Leu Ser Val Gly
        1370                1375                1380
Asp Pro Trp Arg Gln Cys Glu Ala Leu Gln Cys Trp Arg Leu Phe
        1385                1390                1395
Asn Asn Ser Arg Cys Asp Pro Ala Cys Ser Ser Pro Ala Cys Leu
        1400                1405                1410
```

```
Tyr Asp Asn Phe Asp Cys His Ala Gly Gly Arg Glu Arg Thr Cys
    1415            1420                1425

Asn Pro Val Tyr Glu Lys Tyr Cys Ala Asp His Phe Ala Asp Gly
    1430            1435                1440

Arg Cys Asp Gln Gly Cys Asn Thr Glu Glu Cys Gly Trp Asp Gly
    1445            1450                1455

Leu Asp Cys Ala Ser Glu Val Pro Ala Leu Leu Ala Arg Gly Val
    1460            1465                1470

Leu Val Leu Thr Val Leu Leu Pro Pro Glu Glu Leu Leu Arg Ser
    1475            1480                1485

Ser Ala Asp Phe Leu Gln Arg Leu Ser Ala Ile Leu Arg Thr Ser
    1490            1495                1500

Leu Arg Phe Arg Leu Asp Ala His Gly Gln Ala Met Val Phe Pro
    1505            1510                1515

Tyr His Arg Pro Ser Pro Gly Ser Glu Pro Arg Ala Arg Arg Glu
    1520            1525                1530

Leu Ala Pro Glu Val Ile Gly Ser Val Val Met Leu Glu Ile Asp
    1535            1540                1545

Asn Arg Leu Cys Leu Gln Ser Pro Glu Asn Asp His Cys Phe Pro
    1550            1555                1560

Asp Ala Gln Ser Ala Ala Asp Tyr Leu Gly Ala Leu Ser Ala Val
    1565            1570                1575

Glu Arg Leu Asp Phe Pro Tyr Pro Leu Arg Asp Val Arg Gly Glu
    1580            1585                1590

Pro Leu Glu Pro Pro Glu Pro Ser Val Pro Leu
    1595            1600

<210> SEQ ID NO 96
<211> LENGTH: 428
<212> TYPE: PRT
<213> ORGANISM: Homo sapiens

<400> SEQUENCE: 96

Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
            20                  25                  30

Val Gly Glu Arg Cys Gln Leu Glu Asp Pro Cys His Ser Gly Pro Cys
        35                  40                  45

Ala Gly Arg Gly Val Cys Gln Ser Ser Val Val Ala Gly Thr Ala Arg
    50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95

Val Gly Pro Asp Gly Arg Phe Leu Cys Ser Cys Pro Gly Tyr Gln Gly
            100                 105                 110

Gly Arg Ser Cys Arg Ser Asp Val Asp Glu Cys Arg Val Gly Glu Pro
        115                 120                 125

Cys Arg His Gly Gly Thr Cys Leu Asn Thr Pro Gly Ser Phe Arg Cys
    130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
```

-continued

```
                165                 170                 175
Gly Asp Leu Thr Tyr Asp Cys Ala Cys Leu Pro Gly Phe Glu Gly Gln
            180                 185                 190

Asn Cys Glu Val Asn Val Asp Asp Cys Pro Gly His Arg Cys Leu Asn
        195                 200                 205

Gly Gly Thr Cys Val Asp Gly Val Asn Thr Tyr Asn Cys Gln Cys Pro
    210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
            245                 250                 255

Gly Gly His Ser Cys Val Cys Val Asn Gly Trp Thr Gly Glu Ser Cys
            260                 265                 270

Ser Gln Asn Ile Asp Asp Cys Ala Thr Ala Val Cys Phe His Gly Ala
            275                 280                 285

Thr Cys His Asp Arg Val Ala Ser Phe Tyr Cys Ala Cys Pro Met Gly
            290                 295                 300

Lys Thr Gly Leu Leu Cys His Leu Asp Asp Ala Cys Val Ser Asn Pro
305                 310                 315                 320

Cys His Glu Asp Ala Ile Cys Asp Thr Asn Pro Val Asn Gly Arg Ala
                325                 330                 335

Ile Cys Thr Cys Pro Pro Gly Phe Thr Gly Gly Ala Cys Asp Gln Asp
            340                 345                 350

Val Asp Glu Cys Ser Ile Gly Ala Asn Pro Cys Glu His Leu Gly Arg
            355                 360                 365

Cys Val Asn Thr Gln Gly Ser Phe Leu Cys Gln Cys Gly Arg Gly Tyr
    370                 375                 380

Thr Gly Pro Arg Cys Glu Thr Asp Val Asn Glu Cys Leu Ser Gly Pro
385                 390                 395                 400

Cys Arg Asn Gln Ala Thr Cys Leu Asp Arg Ile Gly Gln Phe Thr Cys
                405                 410                 415

Ile Cys Met Ala Gly Phe Thr Gly Thr Tyr Cys Glu
            420                 425
```

ANTI-NOTCH3 ANTIBODIES

CROSS-REFERENCE TO RELATED APPLICATIONS

This application is a U.S. National Stage application filed under 35 U.S.C. §371 of International Application No. PCT/US2013/076615, filed Dec. 19, 2013, which claims the benefit of and priority to U.S. Provisional Patent Application No. 61/866,787, filed Aug. 16, 2013, and U.S. Provisional Patent Application No. 61/739,435, filed Dec. 19, 2012, the entire disclosure of each of which is incorporated by reference herein in its entirety.

FIELD OF THE INVENTION

The field of the invention is molecular biology, immunology and oncology. More particularly, the field is antibodies that bind human Notch3.

BACKGROUND

Notch pathway signaling is involved in numerous cellular processes, including cell fate determination, differentiation, proliferation, apoptosis, migration and angiogenesis. In mammals, there are four Notch proteins (sometimes called "Notch receptors"), designated Notch1-Notch4. All four Notch proteins have a similar domain structure, which includes an extracellular domain, a negative regulatory region (NRR), a single-pass transmembrane domain, and an intracellular domain. The extracellular domain contains a series of EGF-like repeats that are involved in ligand binding. During maturation, the Notch polypeptide is cleaved by a furin-like protease. This cleavage divides the Notch protein into two subunits that are held together by noncovalent interactions of the NRR. In the absence of ligand binding, the NRR domain functions to keep the Notch protein in a protease-resistant conformation. The intracellular domain is a transcription factor called Notch intracellular domain (NICD), which is released upon proteolytic cleavage by gamma secretase, in response to binding of the Notch protein by a ligand. In mammals, the Notch ligands are Delta-like (e.g., DLL1 and DLL4) and Jagged (also referred to as Jag, e.g., Jag1 and Jag2). When the NICD is released, it travels to the nucleus, where it activates transcription of the Notch-responsive genes, HES1, HES5, NRARP, Deltex1 and c-MYC. For reviews of Notch-related biology, see, e.g., Bray, 2006, NATURE REVIEWS 7:678-689; Kopan et al., 2009, CELL 137:216-233.

While Notch proteins play crucial roles in normal development, dysregulation of the Notch proteins is associated with various types of cancer, including T-cell acute lymphatic leukemia/lymphoma (T-All), breast cancer, colon cancer, ovarian cancer and lung cancer. See, e.g., Miele et al., 2006, CURRENT CANCER DRUG TARGETS 6:313-323. Accordingly, one therapeutic approach for the treatment of cancer is inhibition of Notch pathway signaling. Inhibition of Notch pathway signaling has been achieved using monoclonal antibodies (Wu et al., 2010, NATURE 464:1052-1057; Aste-Amézaga et al., 2010, PLOS ONE 5:1-13 e9094).

Naturally-occurring antibodies are multimeric proteins that contain four polypeptide chains (FIG. 1). Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody.

Each variable region contains three hypervariable regions known as complementarity determining regions (CDRs) flanked by four relatively conserved regions known as framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

There is a need for improved antibodies that neutralize the biological activity of human Notch3 and that can be used as therapeutic agents to treat human patients.

SUMMARY OF THE INVENTION

The invention is based on the discovery of antibodies that specifically bind human Notch3. Antibodies disclosed herein contain Notch3 binding sites based on the CDRs of the anti-Notch3 antibodies described herein. The disclosed antibodies prevent or inhibit activation of human Notch3. They do so by inhibiting Notch3 from binding to Notch ligands, i.e., Jag1, Jag2, DLL1, and DLL4. The disclosed antibodies can be used to inhibit the proliferation of tumor cells in vitro and/or in vivo. When administered to a human cancer patient, the antibodies inhibit or reduce tumor growth in the human patient.

These and other aspects and advantages of the invention are illustrated by the following figures, detailed description and claims. As used herein, "including" means without limitation, and examples cited are non-limiting. As used herein, "antibody 4F11" means antibody 4F11, or humanized variants thereof.

DESCRIPTION OF THE DRAWINGS

The invention can be more completely understood with reference to the following drawings.

FIGS. 2A-C provide the amino acid sequence corresponding to the extracellular domain (ECD; amino acids 40 to 1643) of human Notch3 (SEQ ID NO:95). The amino acid sequence begins in FIG. 2A and continues in FIGS. 2B-C.

FIG. 3 provides the amino acid sequence corresponding to EGF-like repeats 1-11 (amino acids 40 to 467 of the extracellular domain shown in FIGS. 2A-C) of human Notch3 (SEQ ID NO:96).

FIG. 7 is a sequence alignment showing the amino acid sequence of the complete immunoglobulin heavy chain variable region of chimeric 4F11 variable region denoted as Ch4F11 and humanized 4F11 heavy chain variable regions denoted as Sh4F11 Hy3-23, Sh4F11 Hv3-23 A28T S31H T62S, Sh4F11 Hv3-23 S31H T62S, Sh4F11 Hv3-23 A28T S31N T62S, and Sh4F11 Hv3-23 A28T T62S. The amino acid sequences for each heavy chain variable region are aligned against one another, and $CDR_1$, $CDR_2$, and $CDR_3$ sequences (Kabat definition) are identified in boxes. The unboxed sequences represent framework (FR) sequences.

FIG. 8 is a sequence alignment showing the isolated $CDR_1$, $CDR_2$, and $CDR_3$ sequences for each of the immunoglobulin heavy chain variable region sequences in FIG. 7.

FIG. 9 is a sequence alignment showing the amino acid sequence of the complete immunoglobulin light chain variable region of chimeric 4F11 denoted as Ch4F11 and humanized 4F11 light chain variable regions denoted as Hu4F11 Kv2D-29, Hu4F11 Kv2D-29 N28H, Hu4F11 Kv2D-29 N28Q, and Hu4F11 Kv2D-29 N28Y. The light chain variable region amino acid sequences are aligned against one another, and $CDR_1$, $CDR_2$, and $CDR_3$ sequences (Kabat definition) are identified in boxes. The unboxed sequences represent framework (FR) sequences.

FIG. 10 is a sequence alignment showing the isolated $CDR_1$, $CDR_2$, and $CDR_3$ sequences for each of the immunoglobulin light chain variable region sequences in FIG. 9.

DETAILED DESCRIPTION

Figure 1:
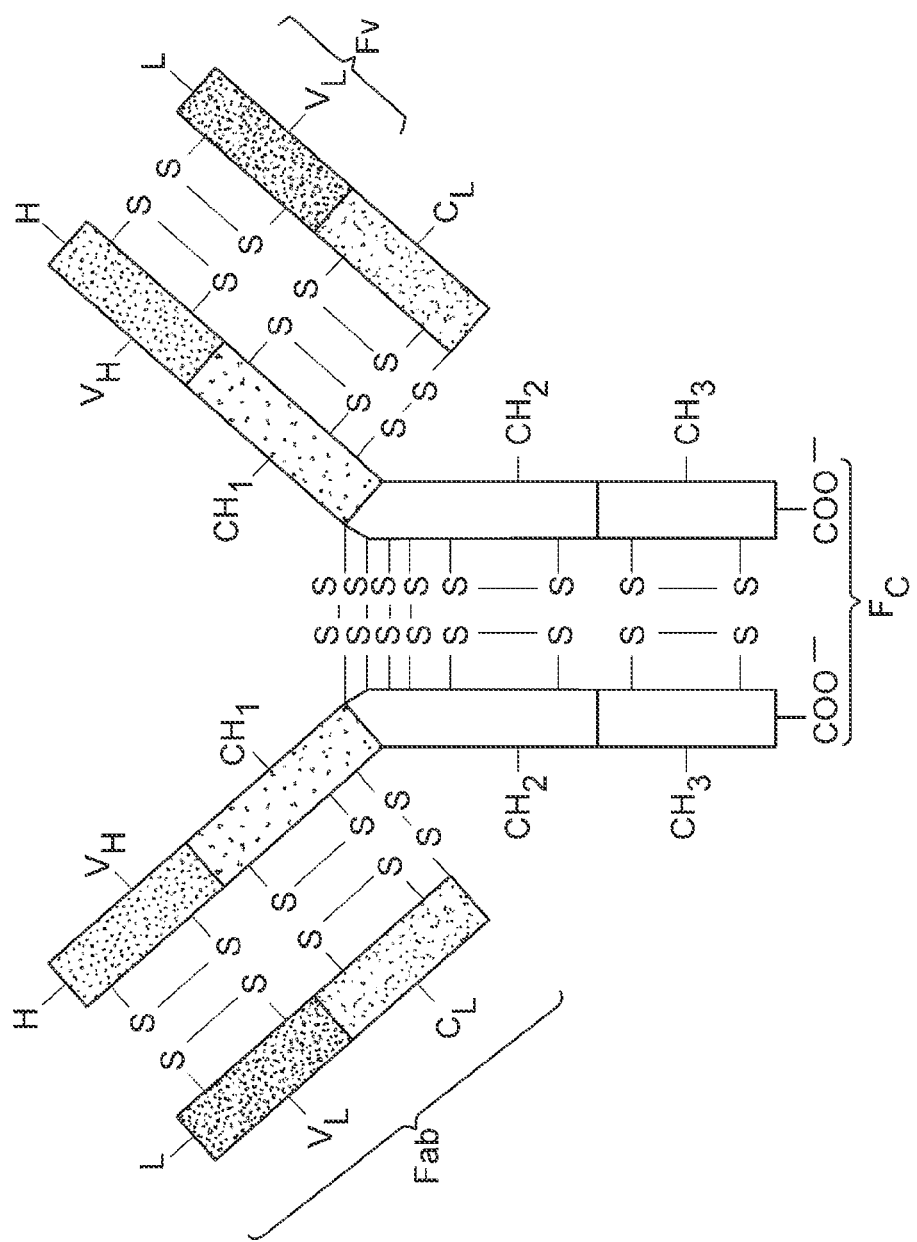
FIG. 1 (prior art) is a schematic representation of a typical naturally-occurring antibody.

The antibodies disclosed herein are based on the antigen binding sites of certain monoclonal antibodies that have been selected on the basis of binding and neutralizing the activity of human Notch3. The antibodies contain immunoglobulin variable region CDR sequences that define a binding site for human Notch3.

Because of the neutralizing activity of these antibodies, they are useful for inhibiting the growth and/or proliferation of certain cancer cells and tumors. The antibodies can be engineered (e.g., humanized) to minimize or eliminate an immune response when administered as a therapeutic antibody to a human patient. Various features and aspects of the invention are discussed in more detail below.

As used herein, unless otherwise indicated, the term "antibody" means an intact antibody (e.g., an intact monoclonal antibody) or antigen-binding fragment of an antibody, including an intact antibody or antigen-binding fragment that has been modified, engineered or chemically conjugated. Examples of antibodies that have been modified or engineered are chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), minibodies, and diabodies. An antibody conjugated to a toxin moiety is an example of a chemically conjugated antibody.

I. Antibodies that Bind Human Notch3

As disclosed herein, the antibodies may comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human Notch3.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding human Notch3. A $CDR_{H1}$ comprises an amino acid sequence selected from the group consisting of SEQ ID NO:5, SEQ ID NO:11, SEQ ID NO:14, SEQ ID NO:51, SEQ ID NO:52, SEQ ID NO:54, SEQ ID NO:55, SEQ ID NO:56, SEQ ID NO:57, SEQ ID NO:58, SEQ ID NO:59, SEQ ID NO:60 and SEQ ID NO:61; a $CDR_{H2}$ comprises an amino acid sequence selected from the group consisting of SEQ ID NO:6, SEQ ID NO:12, SEQ ID NO:15 and SEQ ID NO:53; and a $CDR_{H3}$ comprises an amino acid sequence selected from the group consisting of SEQ ID NO:7 and SEQ ID NO:16. (The immunoglobulin heavy chain variable regions including the referenced CDR sequences can be found in Table 10 and FIGS. 7-8.)

In some embodiments, the antibody comprises an immunoglobulin heavy chain variable region comprising a $CDR_{H1}$ comprising an amino acid sequence selected from the group consisting of SEQ ID NO: 5 and SEQ ID NO: 11, a $CDR_{H2}$ comprising the amino acid sequence of SEQ ID NO: 6, and a $CDR_{H3}$ comprising the amino acid sequence of SEQ ID NO: 7.

In some embodiments, the antibody comprises an immunoglobulin heavy chain variable region comprising a $CDR_{H1}$ comprising an amino acid sequence selected from the group consisting of SEQ ID NO: 51 and SEQ ID NO: 54, a $CDR_{H2}$ comprising the amino acid sequence of SEQ ID NO: 53, and a $CDR_{H3}$ comprising the amino acid sequence of SEQ ID NO: 7.

In some embodiments, the antibody comprises an immunoglobulin heavy chain variable region comprising a $CDR_{H1}$ comprising an amino acid sequence selected from the group consisting of SEQ ID NO: 51 and SEQ ID NO: 55, a $CDR_{H2}$ comprising the amino acid sequence of SEQ ID NO: 53, and a $CDR_{H3}$ comprising the amino acid sequence of SEQ ID NO: 7.

In some embodiments, the antibody comprises an immunoglobulin heavy chain variable region comprising a $CDR_{H1}$ comprising an amino acid sequence selected from the group consisting of SEQ ID NO: 52 and SEQ ID NO: 56, a $CDR_{H2}$ comprising the amino acid sequence of SEQ ID NO: 53, and a $CDR_{H3}$ comprising the amino acid sequence of SEQ ID NO: 7.

In some embodiments, the antibody comprises an immunoglobulin heavy chain variable region comprising a $CDR_{H1}$ comprising an amino acid sequence selected from the group consisting of SEQ ID NO: 5 and SEQ ID NO: 57, a $CDR_{H2}$ comprising the amino acid sequence of SEQ ID NO: 53, and a $CDR_{H3}$ comprising the amino acid sequence of SEQ ID NO: 7.

Preferably, the $CDR_{H1}$, $CDR_{H2}$, and $CDR_{H3}$ sequences are interposed between human or humanized immunoglobulin FR sequences.

In other embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the IgG light chain variable region and the IgG heavy chain variable region together define a single binding site for binding human Notch3. A $CDR_{L1}$ comprises an amino acid sequence selected from the group consisting of SEQ ID NO:8, SEQ ID NO:20, SEQ ID NO:62, SEQ ID NO:63, SEQ ID NO:64, SEQ ID NO:65, SEQ ID NO:66 and SEQ ID NO:67; a $CDR_{L2}$ comprises an amino acid sequence selected from the group consisting of SEQ ID NO:9 or the amino acid sequence of KVS; and a $CDR_{L3}$ comprises an amino acid sequence of SEQ ID NO:10. (The immunoglobulin light chain variable regions including the referenced CDR sequences can be found in Table 11 and FIGS. 9-10.)

In some embodiments, the antibody comprises an immunoglobulin light chain variable region comprising a $CDR_{L1}$ comprising the amino acid sequence of SEQ ID NO: 8, a $CDR_{L2}$ comprising the amino acid sequence of SEQ ID NO: 9, and a $CDR_{L3}$ comprising the amino acid sequence of SEQ ID NO: 10.

In some embodiments, the antibody comprises an immunoglobulin light chain variable region comprising a $CDR_{L1}$ comprising the amino acid sequence of SEQ ID NO: 62, a $CDR_{L2}$ comprising the amino acid sequence of SEQ ID NO: 9, and a $CDR_{L3}$ comprising the amino acid sequence of SEQ ID NO: 10.

In some embodiments, the antibody comprises an immunoglobulin light chain variable region comprising a $CDR_{L1}$ comprising the amino acid sequence of SEQ ID NO: 63, a $CDR_{L2}$ comprising the amino acid sequence of SEQ ID NO: 9, and a $CDR_{L3}$ comprising the amino acid sequence of SEQ ID NO: 10.

In some embodiments, the antibody comprises an immunoglobulin light chain variable region comprising a $CDR_{L1}$ comprising the amino acid sequence of SEQ ID NO: 64, a $CDR_{L2}$ comprising the amino acid sequence of SEQ ID NO: 9, and a $CDR_{L3}$ comprising the amino acid sequence of SEQ ID NO: 10.

Preferably, the $CDR_{L1}$, $CDR_{L2}$, and $CDR_{L3}$ sequences are interposed between human or humanized immunoglobulin FR sequences.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human Notch3. The $CDR_{H1}$ comprises an amino acid sequence selected from the group consisting of SEQ ID NO:5, SEQ ID NO:11, SEQ ID NO:14, SEQ ID NO:51, SEQ ID NO:52, SEQ ID NO:54, SEQ ID NO:55, SEQ ID NO:56, SEQ ID NO:57, SEQ ID NO:58, SEQ ID NO:59, SEQ ID NO:60 and SEQ ID NO:61; the $CDR_{H2}$ comprises an amino acid sequence selected from the group consisting of SEQ ID NO:6, SEQ ID NO:12, SEQ ID NO:15 and SEQ ID NO:53; and the $CDR_{H3}$ comprises an amino acid sequence selected from the group consisting of SEQ ID NO:7 and SEQ ID NO:16. The $CDR_{L1}$ comprises an amino acid sequence selected from the group consisting of SEQ ID NO:8, SEQ ID NO:20, SEQ ID NO:62, SEQ ID NO:63, SEQ ID NO:64, SEQ ID NO:65, SEQ ID NO:66 and SEQ ID NO:67; the $CDR_{L2}$ comprises an amino acid sequence selected from the group consisting of SEQ ID NO:9 or the amino acid sequence of KVS; and the $CDR_{L3}$ comprises an amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:5 and SEQ ID NO:11, a $CDR_{H2}$ comprising the amino acid sequence of SEQ ID NO:6, and a $CDR_{H3}$ comprising the amino acid sequence of SEQ ID NO:7; and an immunoglobulin light chain variable region comprising a $CDR_{L1}$ comprising the amino acid sequence of SEQ ID NO:8, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a $CDR_{H3}$ comprising the amino acid sequence of SEQ ID NO: 7; and an immunoglobulin light chain variable region comprising a $CDR_{L1}$ comprising the amino acid sequence of SEQ ID NO: 62; a $CDR_{L2}$ comprising the amino acid sequence of SEQ ID NO: 9; and a $CDR_{L3}$ comprising the amino acid sequence of SEQ ID NO: 10.

In some embodiments, the antibody comprises an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a $CDR_{H3}$ comprising the amino acid sequence of SEQ ID NO: 7; and an immunoglobulin light chain variable region comprising a $CDR_{L1}$ comprising the amino acid sequence of SEQ ID NO: 63; a $CDR_{L2}$ comprising the amino acid sequence of SEQ ID NO: 9; and a $CDR_{L3}$ comprising the amino acid sequence of SEQ ID NO: 10.

In some embodiments, the antibody comprises an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a $CDR_{H3}$ comprising the amino acid sequence of SEQ ID NO: 7; and an immunoglobulin light chain variable region comprising a $CDR_{L1}$ comprising the amino acid sequence of SEQ ID NO: 64; a $CDR_{L2}$ comprising the amino acid sequence of SEQ ID NO: 9; and a $CDR_{L3}$ comprising the amino acid sequence of SEQ ID NO: 10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 54, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:8, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 54, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:62, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 54, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:63, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 54, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:64, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 55, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:8, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 55, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:62, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 55, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:63, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:51 and SEQ ID NO: 55, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:64, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:52 and SEQ ID NO: 56, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:8, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:52 and SEQ ID NO: 56, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:62, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:52 and SEQ ID NO: 56, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:63, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:52 and SEQ ID NO: 56, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:64, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:5 and SEQ ID NO: 57, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:8, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:5 and SEQ ID NO: 57, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:62, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:5 and SEQ ID NO: 57, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:63, a $CDR_{L2}$ comprising the amino acid sequence of SEQ ID NO:9, and a $CDR_{L3}$ comprising the amino acid sequence of SEQ ID NO:10.

In some embodiments, the antibody comprises an immunoglobulin heavy chain variable region comprising a $CDR_{H1}$ comprising an amino acid sequence selected from the group consisting of SEQ ID NO:5 and SEQ ID NO: 57, a $CDR_{H2}$ comprising the amino acid sequence of SEQ ID NO:53, and a $CDR_{H3}$ comprising the amino acid sequence of SEQ ID NO:7; and an immunoglobulin light chain variable region comprising a $CDR_{L1}$ comprising the amino acid sequence of SEQ ID NO:64, a $CDR_{L2}$ comprising the amino acid sequence of SEQ ID NO:9, and a $CDR_{L3}$ comprising the amino acid sequence of SEQ ID NO:10.

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO:2 (4F11, Ch4F11 Chimeric); SEQ ID NO:34 (Sh4F11 Hv3-23); SEQ ID NO:36 (Sh4F11 Hv3-23 A28T S31H T62S); SEQ ID NO:38 (Sh4F11 Hv3-23 S31H T62S); SEQ ID NO:40 (Sh4F11 Hv3-23 A28T S31N T62S); and SEQ ID NO:42 (Sh4F11 Hv3-23 A28T T62S); and an immunoglobulin light chain variable region. As a convenience for the reader, certain SEQ ID NOs. are followed by a parenthetical including the antibody designation that was the origin of the sequence. For example, "SEQ ID NO:2 (4F11, Ch4F11 Chimeric)" means that SEQ ID NO:2 comes from murine antibody 4F11. SEQ ID NO:2 is also found in the chimeric 4F11 sequence.

In other embodiments, the antibody comprises an immunoglobulin light chain variable region selected from the group consisting of SEQ ID NO:4 (4F11, Ch4F11 Chimeric); SEQ ID NO:44 (Hu4F11 Kv2D-29); SEQ ID NO:46 (Hu4F11 Kv2D-29 N28H); SEQ ID NO:48 (Hu4F11 Kv2D-29 N28Q); and SEQ ID NO:50 (Hu4F11 Kv2D-29 N28Y); and an immunoglobulin heavy chain variable region.

In some embodiments, the antibody comprises an immunoglobulin heavy chain variable region selected from the group consisting of SEQ ID NO:2 (4F11, Ch4F11 Chimeric); SEQ ID NO:34 (Sh4F11 Hv3-23); SEQ ID NO:36 (Sh4F11 Hv3-23 A28T S31H T62S); SEQ ID NO:38 (Sh4F11 Hv3-23 S31H T62S); SEQ ID NO:40 (Sh4F11 Hv3-23 A28T S31N T62S); and SEQ ID NO:42 (Sh4F11 Hv3-23 A28T T62S), and an immunoglobulin light chain variable region selected from the group consisting of SEQ ID NO:4 (4F11, Ch4F11 Chimeric); SEQ ID NO:44 (Hu4F11 Kv2D-29); SEQ ID NO:46 (Hu4F11 Kv2D-29 N28H); SEQ ID NO:48 (Hu4F11 Kv2D-29 N28Q); and SEQ ID NO:50 (Hu4F11 Kv2D-29 N28Y).

In some embodiments, the antibody comprises an immunoglobulin heavy chain variable region comprising the amino acid sequence of SEQ ID NO:2 (4F11, Ch4F11

Chimeric), and an immunoglobulin light chain variable region comprising the amino acid sequence of SEQ ID NO:4 (4F11, Ch4F11 Chimeric).

In some embodiments, the antibody comprises an immunoglobulin heavy chain variable region comprising the amino acid sequence of SEQ ID NO:2 (4F11, Ch4F11 Chimeric), and an immunoglobulin light chain variable region comprising the amino acid sequence of SEQ ID NO:44 (Hu4F11 Kv2D-29).

In some embodiments, the antibody comprises an immunoglobulin heavy chain variable region comprising the amino acid sequence of SEQ ID NO:34 (Sh4F11 Hv3-23), and an immunoglobulin light chain variable region comprising the amino acid sequence of SEQ ID NO:4 (4F11, Ch4F11 Chimeric).

In some embodiments, the antibody comprises an immunoglobulin heavy chain variable region comprising the amino acid sequence of SEQ ID NO:34 (Sh4F11 Hv3-23), and an immunoglobulin light chain variable region comprising the amino acid sequence of SEQ ID NO:44 (Hu4F11 Kv2D-29).

In some embodiments, the antibody comprises an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:46 (Hu4F11 Kv2D-29 N28H).

In some embodiments, the antibody comprises an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:46 (Hu4F11 Kv2D-29 N28H).

In some embodiments, the antibody comprises an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:46 (Hu4F11 Kv2D-29 N28H).

In some embodiments, the antibody comprises an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:46 (Hu4F11 Kv2D-29 N28H).

In some embodiments, the antibody comprises an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:48 (Hu4F11 Kv2D-29 N28Q).

In some embodiments, the antibody comprises an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:48 (Hu4F11 Kv2D-29 N28Q).

In some embodiments, the antibody comprises an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:48 (Hu4F11 Kv2D-29 N28Q).

In some embodiments, the antibody comprises an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:48 (Hu4F11 Kv2D-29 N28Q).

In some embodiments, the antibody comprises an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:50 (Hu4F11 Kv2D-29 N28Y).

In some embodiments, the antibody comprises an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:50 (Hu4F11 Kv2D-29 N28Y).

In some embodiments, the antibody comprises an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:50 (Hu4F11 Kv2D-29 N28Y).

In some embodiments, the antibody comprises an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:50 (Hu4F11 Kv2D-29 N28Y).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO: 27 (4F11); SEQ ID NO:74 (Ch4F11 Chimeric); SEQ ID NO:76 (Sh4F11 Hv3-23); SEQ ID NO:78 (Sh4F11 Hv3-23 A28T S31H T62S); SEQ ID NO:80 (Sh4F11 Hv3-23 S31H T62S); SEQ ID NO:82 (Sh4F11 Hv3-23 A28T S31N T62S); and SEQ ID NO:84 (Sh4F11 Hv3-23 A28T T62S); and an immunoglobulin light chain.

In other embodiments, the antibody comprises an immunoglobulin light chain selected from the group consisting of SEQ ID NO:29 (4F11); SEQ ID NO:86 (Ch4F11 Chimeric); SEQ ID NO:88 (Hu4F11 Kv2D-29 Kappa); SEQ ID NO:90 (Hu4F11 Kv2D-29 N28H Kappa); SEQ ID NO:92 (Hu4F11 Kv2D-29 N28Q Kappa); and SEQ ID NO:94 (Hu4F11 Kv2D-29 N28Y Kappa); and an immunoglobulin heavy chain.

In some embodiments, the antibody comprises an immunoglobulin heavy chain selected from the group consisting of SEQ ID NO: 27 (4F11); SEQ ID NO:74 (Ch4F11 Chimeric); SEQ ID NO:76 (Sh4F11 Hv3-23); SEQ ID NO:78 (Sh4F11 Hv3-23 A28T S31H T62S); SEQ ID NO:80 (Sh4F11 Hv3-23 S31H T62S); SEQ ID NO:82 (Sh4F11 Hv3-23 A28T S31N T62S); and SEQ ID NO:84 (Sh4F11 Hv3-23 A28T T62S); and an immunoglobulin light chain selected from the group consisting of SEQ ID NO:29 (4F11); SEQ ID NO:86 (Ch4F11 Chimeric); SEQ ID NO:88 (Hu4F11 Kv2D-29 Kappa); SEQ ID NO:90 (Hu4F11 Kv2D-29 N28H Kappa); SEQ ID NO:92 (Hu4F11 Kv2D-29 N28Q Kappa); and SEQ ID NO:94 (Hu4F11 Kv2D-29 N28Y Kappa).

In some embodiments, the antibody comprises an immunoglobulin heavy chain comprising the amino acid sequence of SEQ ID NO: 27 (4F11), and an immunoglobulin light chain comprising the amino acid sequence of SEQ ID NO: 29 (4F11).

In some embodiments, the antibody comprises an immunoglobulin heavy chain comprising the amino acid sequence of SEQ ID NO: 74 (Ch4F11), and an immunoglobulin light chain comprising the amino acid sequence of SEQ ID NO: 86 (Ch4F11).

In some embodiments, the antibody comprises an immunoglobulin heavy chain comprising the amino acid sequence of SEQ ID NO: 74 (Ch4F11), and an immunoglobulin light chain comprising the amino acid sequence of SEQ ID NO: 88 (Hu4F11 Kv2D-29).

In some embodiments, the antibody comprises an immunoglobulin heavy chain comprising the amino acid sequence of SEQ ID NO: 76 (Sh4F11 Hv3-23), and an immunoglobulin light chain comprising the amino acid sequence of SEQ ID NO: 86 (Ch4F11).

In some embodiments, the antibody comprises an immunoglobulin heavy chain comprising the amino acid sequence of SEQ ID NO: 76 (Sh4F11 Hv3-23), and an immunoglobulin light chain comprising the amino acid sequence of SEQ ID NO: 88 (Hu4F11 Kv2D-29).

In some embodiments, the antibody comprises an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 90 (Hu4F11 Kv2D-29 N28H Kappa).

In some embodiments, the antibody comprises an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 90 (Hu4F11 Kv2D-29 N28H Kappa).

In some embodiments, the antibody comprises an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 90 (Hu4F11 Kv2D-29 N28H Kappa).

In some embodiments, the antibody comprises an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 90 (Hu4F11 Kv2D-29 N28H Kappa).

In some embodiments, the antibody comprises an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 92 (Hu4F11 Kv2D-29 N28Q Kappa).

In some embodiments, the antibody comprises an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 92 (Hu4F11 Kv2D-29 N28Q Kappa).

In some embodiments, the antibody comprises an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 92 (Hu4F11 Kv2D-29 N28Q Kappa).

In some embodiments, the antibody comprises an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 92 (Hu4F11 Kv2D-29 N28Q Kappa).

In some embodiments, the antibody comprises an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 94 (Hu4F11 Kv2D-29 N28Y Kappa).

In some embodiments, the antibody comprises an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 94 (Hu4F11 Kv2D-29 N28Y Kappa).

In some embodiments, the antibody comprises an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 94 (Hu4F11 Kv2D-29 N28Y Kappa).

In some embodiments, the antibody comprises an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 94 (Hu4F11 Kv2D-29 N28Y Kappa).

In other embodiments, an isolated antibody that binds human Notch3 comprises an immunoglobulin heavy chain variable region comprising an amino acid sequence that is at least 70%, 75%, 80%, 85%, 90%, 95%, 98%, or 99% identical to the entire variable region or the FR sequence of SEQ ID NO:2 (4F11, Ch4F11 Chimeric); SEQ ID NO:34 (Sh4F11 Hv3-23); SEQ ID NO:36 (Sh4F11 Hv3-23 A28T S31H T62S); SEQ ID NO:38 (Sh4F11 Hv3-23 S31H T62S); SEQ ID NO:40 (Sh4F11 Hv3-23 A28T S31N T62S); or SEQ ID NO:42 (Sh4F11 Hv3-23 A28T T62S).

In other embodiments, an isolated antibody that binds human Notch3 comprises an immunoglobulin light chain variable region comprising an amino acid sequence that is at least 70%, 75%, 80%, 85%, 90%, 95%, 98%, or 99% identical to the entire variable region or the FR sequence of SEQ ID NO:4 (4F11, Ch4F11 Chimeric); SEQ ID NO:44 (Hu4F11 Kv2D-29); SEQ ID NO:46 (Hu4F11 Kv2D-29 N28H); SEQ ID NO:48 (Hu4F11 Kv2D-29 N28Q); or SEQ ID NO:50 (Hu4F11 Kv2D-29 N28Y).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36:290-300; Altschul et al., (1997) NUCLEIC ACIDS RES. 25:3389-3402, herein incorporated by reference) are tailored for sequence similarity searching. For a discussion of basic issues in searching sequence databases see Altschul et al., (1994) NATURE GENETICS 6:119-129, herein fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference herein).

Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: –G, Cost to open gap [Integer]: default=5 for nucleotides/11 for proteins; –E, Cost to extend gap [Integer]: default=2 for nucleotides/1 for proteins; –q, Penalty for nucleotide mismatch [Integer]: default=–3; –r, reward for nucleotide match [Integer]: default=1; –e, expect value [Real]: default=10; –W, word-size [Integer]: default=11 for nucleotides/28 for megablast/3 for proteins; –y, Dropoff (X) for blast extensions in bits: default=20 for blastn/7 for others; –X, X dropoff value for gapped alignment (in bits): default=15 for all programs, not applicable to blastn; and –Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that immunoglobulin heavy chain variable region sequences and/or light chain variable region sequences that together bind human Notch3 may contain amino acid alterations (e.g., at least 1, 2, 3, 4, 5, or 10 amino acid substitutions, deletions, or additions) in the framework regions of the heavy and/or light chain variable regions.

In certain embodiments, an isolated antibody binds human Notch3 with a $K_D$ of about 35 nM, 25 nM, 15 nM 10 nM, 5 nM, 1 nM, 900 pM, 850 pM, 800 pM, 750 pM, 700 pM, 650 pM, 600 pM, 500 pM, 400 pM, 300 pM, 250 pM, 200 pM or less. Unless otherwise specified, $K_D$ values are determined by surface plasmon resonance methods under the conditions described in Examples 3 and 9.

In some embodiments, monoclonal antibodies bind to the same epitope on human Notch3 as antibody 4F11. In some embodiments, monoclonal antibodies compete for binding to human Notch3 with antibody 4F11. For example, monoclonal antibodies may compete for binding to the extracellular domain (ECD) of Notch3 with antibody 4F11 (amino acid sequence corresponding to the human Notch3 ECD is shown in FIGS. 2A-C). In another example, monoclonal antibodies may compete for binding to EGF-like repeats 1-11 of human Notch3 with antibody 4F11 (amino acid sequence corresponding to EGF-like repeats 1-11 of human Notch3 is shown in FIG. 3).

Competition assays for determining whether an antibody binds to the same epitope as, or competes for binding with, antibody 4F11 are known in the art. Exemplary competition assays include immunoassays (e.g., ELISA assays, RIA assays), BIAcore analysis, biolayer interferometry and flow cytometry.

Typically, a competition assay involves the use of an antigen (e.g., a human Notch3 protein or fragment thereof) bound to a solid surface or expressed on a cell surface, a test anti-Notch3-binding antibody and a reference antibody (i.e., antibody 4F11). The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

In an exemplary competition assay, a reference anti-Notch3 antibody (i.e., antibody 4F11) is biotinylated using commercially available reagents. The biotinylated reference antibody is mixed with serial dilutions of the test antibody or unlabeled reference antibody (self-competition control) resulting in a mixture of various molar ratios (e.g., 1×, 5×, 10×, 20× or 100×) of test antibody (or unlabeled reference antibody) to labeled reference antibody. The antibody mixture is added to a human Notch3 (e.g., extracellular domain of human Notch3) polypeptide coated-ELISA plate. The plate is then washed and horseradish peroxidase (HRP)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a SpectraMax® M2 spectrometer (Molecular Devices). OD units corresponding to zero percent inhibition are determined from wells without any competing antibody. OD units corresponding to 100% inhibition, i.e., the assay background are determined from wells without any labeled reference antibody or test antibody. Percent inhibition of labeled reference antibody to Notch3 by the test antibody (or the unlabeled reference antibody) at each concentration is calculated as follows: % inhibition= (1–(OD units–100% inhibition)/(0% inhibition–100% inhibition))*100. Persons skilled in the art will appreciate that the competition assay can be performed using various detection systems known in the art.

A competition assay may be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99% as measured in a competitive binding assay.

Two antibodies may be determined to bind to the same epitope if essentially all amino acid mutations in the antigen that reduce or eliminate binding of one antibody reduce or eliminate binding of the other. Two antibodies may be determined to bind to overlapping epitopes if only a subset of the amino acid mutations that reduce or eliminate binding of antibody reduce or eliminate binding of the other.

II. Antibody Production

Methods for producing antibodies of the invention are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibody. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector encoding a polypeptide comprising an entire, or part of, a heavy chain or heavy chain variable region, and another expression vector encoding a polypeptide comprising an entire, or part of, a light chain or light chain variable region).

A polypeptide comprising an immunoglobulin heavy chain variable region or light chain variable region can be produced by growing (culturing) a host cell transfected with an expression vector encoding such variable region, under conditions that permit expression of the polypeptide. Following expression, the polypeptide can be harvested and purified or isolated using techniques known in the art, e.g., affinity tags such as glutathione-S-transferase (GST) and histidine tags.

A monoclonal antibody that binds human Notch3, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment of the antibody) can be harvested and purified or isolated using techniques known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When administered to a human, the disclosed antibodies preferably are "humanized" to reduce or eliminate antigenicity in humans. Preferably, the humanized antibodies have the same, or substantially the same, affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments of the invention, the CDRs of the light and heavy chain variable regions of an anti-Notch3 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody of the invention.

The antibody can be conjugated to an effector moiety such as a small molecule toxin or a radionuclide using standard in vitro conjugation chemistries. If the effector moiety is a polypeptide, the antibody can be chemically conjugated to the effector or joined to the effector as a fusion protein. Construction of fusion proteins is within ordinary skill in the art.

IV. Use of Antibodies

Antibodies disclosed herein may be engineered (e.g., humanized) for administration to humans. Antibodies disclosed herein can be used to treat various forms of cancer, e.g., breast, ovarian, prostate, cervical, colorectal, lung, pancreatic, gastric, and head and neck cancers. The cancer cells are exposed to a therapeutically effective amount of the antibody so as to inhibit or reduce proliferation of the cancer cells. In some embodiments, the antibodies inhibit cancer cell proliferation by at least 40%, 50%, 60%, 70%, 80%, 90%, 95%, 98%, 99% or 100%.

In some embodiments, the disclosed antibodies may inhibit or reduce proliferation of a tumor cell by inhibiting binding of human Notch3 to a ligand, e.g., Jag1, Jag2, DLL1, and DLL4. The disclosed antibodies can be used in a method to inhibit tumor growth in a human patient. The method comprises administering to the patient a therapeutically effective amount of the antibody.

Cancers associated with Notch3 overexpression and/or activation include, but are not limited to, breast cancer, ovarian cancer, prostate cancer, cervical cancer, lung cancer, brain cancer (e.g., glioblastoma, astrocytoma, neuroblastoma), melanomas, gastrointestinal cancers (e.g., colorectal, pancreatic, and gastric), head and neck cancer, sarcomas (e.g. rhabdomyosarcoma, osteosarcoma), and hematopoietic cell cancers, (e.g., multiple myeloma, leukemia, e.g., precursor T acute lymphoblastic leukemia (T-ALL), precursor B acute lymphoblastic leukemia (B-ALL) and B-cell chronic lymphoblastic leukemia (B-CLL)).

As used herein, "treat", "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments, a monoclonal antibody is lyophilized, and then reconstituted in buffered saline, at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™

(BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1: Production of Anti-hNotch3 Monoclonal Antibodies

Immunizations, fusions, and primary screens were conducted using conventional methods following the Repetitive Immunization Multiple Sites (RIMMS) protocol. Five AJ mice and five Balb/c mice were immunized with a protein containing amino acids 1-428 of human Notch3 fused to the Fc portion of human IgG. In addition, five AJ and five Balb/c mice were immunized with a concatemeric protein containing two repeats of the region of Notch3 comprising EGF-like domains 9-12. From each immunization strategy, two AJ mice and 2 Balb/c mice having sera displaying high binding to immunogen by Enzyme Linked ImmunoSorbent Assay (ELISA) were chosen for subsequent fusion. Spleens and lymph nodes from the selected mice were harvested. B cells were harvested and fused with a myeloma line. Fusion products from AJ mice and Balb/c mice were serially diluted in forty 96-well plates to near clonality. A total of 5,280 supernatants from the cell fusions were screened for binding to human Notch3 on the surface of CHO cells, using a Mesoscale electrochemiluminescence assay (MSD). In total, four hundred and twenty supernatants that bound human Notch3 in this assay were identified from the AJ and Balb/c fusions. These fusion products were further characterized by in vitro biochemical and cell-based assays, as discussed below. A panel of hybridomas was selected, the hybridomas were subcloned, and monoclonal hybridomas were expanded. Antibodies were expressed from the hybridoma cell lines and purified by affinity chromatography on Protein G resin under standard conditions.

Example 2: Sequence Analysis of Anti-Notch3 Monoclonal Antibodies

The light chain isotype and heavy chain isotype of the monoclonal antibody, 4F11, in Example 1 was determined using the IsoStrip™ Mouse Monoclonal Antibody Isotyping Kit according to the manufacturer's instructions (Roche Applied Science, Indianapolis, Ind.). The antibody was determined to be kappa light chain and IgG1 heavy chain.

The heavy and light chain variable regions of the mouse monoclonal antibody were sequenced using 5' RACE (Rapid Amplification of cDNA Ends). Total RNA was extracted from the hybridoma cell line using the RNeasy Miniprep kit according to the vendor's instructions (Qiagen, Valencia, Calif.). Full-length first strand cDNA containing 5' ends was generated using the SMARTer™ RACE cDNA Amplification Kit (Clontech, Mountain View, Calif.) according to the manufacturer's instructions using random primers for 5' RACE.

The variable regions of the light (kappa) and heavy (IgG1) chains were amplified by PCR, using KOD Hot Start Polymerase (EMD Chemicals, Gibbstown, N.J.) according to the manufacturer's instructions. For amplification of 5' cDNA ends in conjunction with the SMARTer™ RACE cDNA Amplification Kit, the Universal Primer Mix A primer (Clontech), a mix of 5'CTAATACGACTCAC-TATAGGGCAAGCAGTGGTATCAACGCAGAGT 3' (SEQ ID NO: 13) and 5' CTAATACGACTCAC-TATAGGGC 3' (SEQ ID NO: 17), was used as a 5' primer. The heavy chain variable region was amplified using the above 5' primers and a 3' IgG1 constant region specific primer, 5' TATGCAAGGCTTACAACCACA 3' (SEQ ID NO: 18). The kappa chain variable region was amplified with the above 5' primers and a 3' kappa constant region specific primer, 5' CGACTGAGGCACCTCCAGATGTT 3' (SEQ ID NO: 19).

Individual PCR products were isolated by agarose gel electrophoresis and purified using the Qiaquick Gel Purification kit according to the manufacturer's instructions (Qiagen). The PCR products were subsequently cloned into the pCR® 4Blunt using the Zero Blunt® TOPO® PCR Cloning Kit according to the manufacturer's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO: 21) and M13 Reverse primers (5' CAGGAAACAGC-TATGACC 3') (SEQ ID NO: 30) by Beckman Genomics (Danvers, Mass.), using standard dideoxy DNA sequencing methods to identify the sequence of the variable region sequences. The sequences were analyzed using Vector NTI software (Invitrogen) and the IMGT/V-Quest web server (available on the world wide web at imgt.cines.fr) to identify and confirm variable region sequences.

The nucleic acid sequences encoding and the protein sequences defining variable regions of the murine monoclonal antibodies are summarized below (amino terminal signal peptide sequences are not shown). CDR sequences (Kabat definition) are shown in bold and are underlined in the amino acid sequences.

Nucleic Acid Sequence Encoding the Heavy Chain Variable Region of the 4F11 Antibody (SEQ ID NO: 1)

```
  1 gaagtgcagc tggtggagtc tggggggaggc ttagtgaagc ctggagggtc cctgaaactc 61 tcctgtgcag cctctggatt cgctttcagt agctatgaca tgtcttgggt tcgccagact 121 ccggagaaga ggctggagtg ggtcgcatac attagtcgtg gtggtggtag cacctactat
```

-continued

```
181 ccagacactg tgaagggccg attcaccatc tccagagaca atgccaagaa caccctgtac 241 ctgcaaatga gcagtctgaa gtctgaggac acagccatgt attactgtgg aagacatgct 301 actacggcct actggtactt cgatgtctgg ggcgcaggga ccacggtcac cgtctcctca
```

Protein Sequence Defining the Heavy Chain Variable Region of the 4F11 Antibody (SEQ ID NO: 2)

```
 1 evqlvesggg lvkpggslkl scaasgfafs sydmswvrqt pekrlewvay isrgggstyy 61 pdtvkgrfti srdnakntly lqmsslksed tamyycgrha ttaywyfdvw gagttvtvss
```

Nucleic Acid Sequence Encoding the Kappa Chain Variable Region of the 4F11 Antibody (SEQ ID NO: 3)

```
 1 gatgttgtga tgacccaaac tccactctcc ctgcctgtca gtcttggaga tcaagcctcc 61 atctcttgca gatctagtca gagccttgta cacactaatg caacaccta tttacattgg 121 tacctgcaga agccaggcca gtctccaaaa ctcctgatct acaaagtttc caaccgattt 181 tctggggtcc cagacaggtt cagtggcagt ggatcaggga cagatttcac actcaagatc 241 agcagagtgg aggctgagga tctgggagtt tatttctgct ctcaaagtac acatgttccg 301 tggacgttcg gtggaggcac caagctggaa atcaaa
```

Protein Sequence Defining the Kappa Chain Variable Region of the 4F11 Antibody (SEQ ID NO: 4)

```
 1 dvvmtqtpls lpvslgdqas iscrssqslv htngntylhw ylqkpgqspk lliykvsnrf 61 sgvpdrfsgs gsgtdftlki srveaedlgv yfcsqsthvp wtfgggtkle ik
```

Table 1 is a concordance chart showing the SEQ ID NO. of each sequence discussed in this Example.

TABLE 1

| SEQ. ID NO. | Nucleic Acid or Protein |
|---|---|
| 1 | 4F11 Heavy Chain Variable Region-nucleic acid |
| 2 | 4F11 Heavy Chain Variable Region-protein |
| 3 | 4F11 Light (kappa) Chain Variable Region-nucleic acid |
| 4 | 4F11 Light (kappa) Chain Variable Region-protein |
| 5 | 4F11 Heavy Chain CDR$_1$ |
| 6 | 4F11 Heavy Chain CDR$_2$ |

TABLE 1-continued

| SEQ. ID NO. | Nucleic Acid or Protein |
|---|---|
| 7 | 4F11 Heavy Chain CDR$_3$ |
| 8 | 4F11 Light (kappa) Chain CDR$_1$ |
| 9 | 4F11 Light (kappa) Chain CDR$_2$ |
| 10 | 4F11 Light (kappa) Chain CDR$_3$ |

Mouse monoclonal antibody heavy chain CDR sequences (Kabat, Chothia, and IMGT definitions) for 4F11 are shown in Table 2.

TABLE 2

| | CDR1 | CDR2 | CDR3 |
|---|---|---|---|
| Kabat | SYDMS (SEQ ID NO: 5) | YISRGGGSTYYPDTVKG (SEQ ID NO: 6) | HATTAYWYFDV (SEQ ID NO: 7) |
| Chothia | GFAFSSY (SEQ ID NO: 11) | SRGGGS (SEQ ID NO: 12) | HATTAYWYFDV (SEQ ID NO: 7) |
| IMGT | GFAFSSYD (SEQ ID NO: 14) | ISRGGGST (SEQ ID NO: 15) | GRHATTAYWYFDV (SEQ ID NO: 16) |

Mouse monoclonal antibody kappa light chain CDR sequences (Kabat, Chothia, and IMGT definitions) for 4F11 are shown in Table 3.

TABLE 3

|  | CDR1 | CDR2 | CDR3 |
|---|---|---|---|
| Kabat/Chothia | RSSQSLVHTNGNTYLH (SEQ ID NO: 8) | KVSNRFS (SEQ ID NO: 9) | SQSTHVPWT (SEQ ID NO: 10) |
| IMGT | QSLVHTNGNTY (SEQ ID NO: 20) | KVS | SQSTHVPWT (SEQ ID NO: 10) |

To create the complete heavy or kappa chain antibody sequences, each variable sequence above is combined with its respective constant region. For example, a complete heavy chain comprises a heavy variable sequence followed by the murine IgG1 heavy chain constant sequence, and a complete kappa chain comprises a kappa variable sequence followed by the murine kappa light chain constant sequence.

Nucleic Acid Sequence Encoding the Murine IgG1 Heavy Chain Constant Region (SEQ ID NO: 22)

```
  1 gccaaaacga caccccatc tgtctatcca ctggcccctg gatctgctgc ccaaactaac
 61 tccatggtga ccctgggatg cctggtcaag ggctatttcc ctgagccagt gacagtgacc
121 tggaactctg gatccctgtc cagcggtgtg cacaccttcc cagctgtcct gcagtctgac
181 ctctacactc tgagcagctc agtgactgtc ccctcagca cctggcccag cgagaccgtc
241 acctgcaacg ttgcccaccc ggccagcagc accaaggtgg acaagaaaat tgtgcccagg
301 gattgtggtt gtaagccttg catatgtaca gtcccagaag tatcatctgt cttcatcttc
361 cccccaaagc ccaaggatgt gctcaccatt actctgactc ctaaggtcac gtgtgttgtg
421 gtagacatca gcaaggatga tcccgaggtc cagttcagct ggtttgtaga tgatgtggag
481 gtgcacacag ctcagacgca accccgggag gagcagttca acagcacttt ccgctcagtc
541 agtgaacttc ccatcatgca ccaggactgg ctcaatggca aggagttcaa atgcagggtc
601 aacagtgcag ctttccctgc ccccatcgag aaaaccatct ccaaaaccaa aggcagaccg
661 aaggctccac aggtgtacac cattccacct cccaaggagc agatggccaa ggataaagtc
721 agtctgacct gcatgataac agacttcttc cctgaagaca ttactgtgga gtggcagtgg
781 aatgggcagc cagcggagaa ctacaagaac actcagccca tcatggacac agatggctct
841 tacttcgtct acagcaagct caatgtgcag aagagcaact gggaggcagg aaatactttc
901 acctgctctg tgttacatga gggcctgcac aaccaccata ctgagaagag cctctcccac
961 tctcctggta aa
```

Protein Sequence Defining the Murine IgG1 Heavy Chain Constant Region (SEQ ID NO: 23)

```
  1 akttppsvyp lapgsaaqtn smvtlgclvk gyfpepvtvt wnsgslssgv htfpavlqsd
 61 lytlsssvtv psstwpsetv tcnvahpass tkvdkkivpr dcgckpcict vpevssvfif
121 ppkpkdvlti tltpkvtcvv vdiskddpev qfswfvddve vhtaqtqpre eqfnstfrsv
181 selpimhqdw lngkefkcrv nsaafpapie ktisktkgrp kapqvytipp pkeqmakdkv
241 sltcmitdff peditvewqw ngqpaenykn tqpimdtdgs yfvysklnvq ksnweagntf
301 tcsvlheglh nhhtekslsh spgk
```

Nucleic Acid Sequence Encoding the Murine Kappa Light Chain Constant Region (SEQ ID NO: 24)

```
  1 cgggctgatg ctgcaccaac tgtatccatc ttcccaccat ccagtgagca gttaacatct
 61 ggaggtgcct cagtcgtgtg cttcttgaac aacttctacc ccaaagacat caatgtcaag
121 tggaagattg atggcagtga acgacaaaat ggcgtcctga acagttggac tgatcaggac
181 agcaaagaca gcacctacag catgagcagc accctcacgt tgaccaagga cgagtatgaa
241 cgacataaca gctatacctg tgaggccact cacaagacat caacttcacc cattgtcaag
301 agcttcaaca ggaatgagtg t
```

Protein Sequence Defining the Murine Kappa Light Chain Constant Region (SEQ ID NO: 25)

```
 1 radaaptvsi fppsseqlts ggasvvcfln nfypkdinvk wkidgserqn gvlnswtdqd
61 skdstysmss tltltkdeye rhnsytceat hktstspivk sfnrnec
```

The following sequences represent the actual or contemplated full length heavy and light chain sequences (i.e., containing both the variable and constant regions sequences) for the 4F11 antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length IgG heavy chain and light chain sequences. It is also contemplated that the variable region sequences can be ligated to other constant region sequences to produce active full length IgG heavy and light chains.

Nucleic Acid Sequence Encoding the Full Length Heavy Chain Sequence (Heavy Chain Variable Region and IgG1 Constant Region) of 4F11 (SEQ ID NO: 26)

```
   1 gaagtgcagc tggtggagtc tgggggaggc ttagtgaagc ctggagggtc cctgaaactc
  61 tcctgtgcag cctctggatt cgctttcagt agctatgaca tgtcttgggt tcgccagact
 121 ccggagaaga ggctggagtg ggtcgcatac attagtcgtg gtggtggtag cacctactat
 181 ccagacactg tgaagggccg attcaccatc tccagagaca atgccaagaa caccctgtac
 241 ctgcaaatga gcagtctgaa gtctgaggac acagccatgt attactgtgg aagacatgct
 301 actacggcct actggtactt cgatgtctgg ggcgcaggga ccacggtcac cgtctcctca
 361 gccaaaacga cacccccatc tgtctatcca ctggccctg gatctgctgc ccaaactaac
 421 tccatggtga ccctgggatg cctggtcaag ggctatttcc ctgagccagt gacagtgacc
 481 tggaactctg gatccctgtc cagcggtgtg cacaccttcc cagctgtcct gcagtctgac
 541 ctctacactc tgagcagctc agtgactgtc cctccagca cctggcccag cgagaccgtc
 601 acctgcaacg ttgcccaccc ggccagcagc accaaggtgg acaagaaaat tgtgcccagg
 661 gattgtggtt gtaagccttg catatgtaca gtcccagaag tatcatctgt cttcatcttc
 721 cccccaaagc ccaaggatgt gctcaccatt actctgactc ctaaggtcac gtgtgttgtg
 781 gtagacatca gcaaggatga tcccgaggtc cagttcagct ggtttgtaga tgatgtggag
 841 gtgcacacag ctcagacgca accccgggag gagcagttca acagcacttt ccgctcagtc
 901 agtgaacttc ccatcatgca ccaggactgg ctcaatggca aggagttcaa atgcagggtc
 961 aacagtgcag ctttccctgc ccccatcgag aaaaccatct ccaaaaccaa aggcagaccg
1021 aaggctccac aggtgtacac cattccacct cccaaggagc agatggccaa ggataaagtc
1081 agtctgacct gcatgataac agacttcttc cctgaagaca ttactgtgga gtggcagtgg
1141 aatgggcagc cagcggagaa ctacaagaac actcagccca tcatggacac agatggctct
1201 tacttcgtct acagcaagct caatgtgcag aagagcaact gggaggcagg aaatactttc
```

-continued

```
1261 acctgctctg tgttacatga gggcctgcac aaccaccata ctgagaagag cctctcccac 1321 tctcctggta aa
```

Protein Sequence Defining the Full Length Heavy Chain Sequence (Heavy Chain Variable Region and IgG1 Constant Region) of 4F11 (SEQ ID NO: 27)

```
  1 evqlvesggg lvkpggslkl scaasgfafs sydmswvrqt pekrlewvay isrgggstyy 61 pdtvkgrfti srdnakntly lqmsslksed tamyycgrha ttaywyfdvw gagttvtvss 121 akttppsvyp lapgsaaqtn smvtlgclvk gyfpepvtvt wnsgslssgv htfpavlqsd 181 lytlsssvtv psstwpsetv tcnvahpass tkvdkkivpr dcgckpcict vpevssvfif 241 ppkpkdvlti tltpkvtcvv vdiskddpev qfswfvddve vhtaqtqpre eqfnstfrsv 301 selpimhqdw lngkefkcrv nsaafpapie ktisktkgrp kapqvytipp pkeqmakdkv 361 sltcmitdff peditvewqw ngqpaenykn tqpimdtdgs yfvysklnvq ksnweagntf 421 tcsvlheglh nhhtekslsh spgk
```

Nucleic Acid Sequence Encoding the Full Length Light Chain Sequence (Kappa Chain Variable Region and Constant Region) of 4F11 (SEQ ID NO: 28)

```
  1 gatgttgtga tgacccaaac tccactctcc ctgcctgtca gtcttggaga tcaagcctcc 61 atctcttgca gatctagtca gagccttgta cacactaatg caacaccta tttacattgg 121 tacctgcaga agccaggcca gtctccaaaa ctcctgatct acaaagtttc caaccgattt 181 tctggggtcc cagacaggtt cagtggcagt ggatcaggga cagatttcac actcaagatc 241 agcagagtgg aggctgagga tctgggagtt tatttctgct ctcaaagtac acatgttccg 301 tggacgttcg gtggaggcac caagctggaa atcaaacggg ctgatgctgc accaactgta 361 tccatcttcc caccatccag tgagcagtta acatctggag gtgcctcagt cgtgtgcttc 421 ttgaacaact tctaccccaa agacatcaat gtcaagtgga agattgatgg cagtgaacga 481 caaaatggcg tcctgaacag ttggactgat caggacagca aagacagcac ctacagcatg 541 agcagcaccc tcacgttgac caaggacgag tatgaacgac ataacagcta tacctgtgag 601 gccactcaca agacatcaac ttcacccatt gtcaagagct caacaggaa tgagtgt
```

Protein Sequence Defining the Full Length Light Chain Sequence (Kappa Chain Variable Region and Constant Region) of 4F11 (SEQ ID NO: 29)

```
  1 dvvmtqtpls lpvslgdqas iscrssqslv htngntylhw ylqkpgqspk lliykvsnrf 61 sgvpdrfsgs gsgtdftlki srveaedlgv yfcsqsthvp wtfggtkle ikradaaptv 121 sifppsseql tsggasvvcf lnnfypkdin vkwkidgser qngvlnswtd qdskdstysm 181 sstltltkde yerhnsytce athktstspi vksfnrnec
```

Table 4 is a concordance chart showing the correspondence between the full length sequences of the antibodies discussed in this Example with those presented in the Sequence Listing.

TABLE 4

| SEQ ID NO. | Nucleic Acid or Protein |
|---|---|
| 26 | 4F11 Heavy Variable + IgG1 Constant-nucleic acid |
| 27 | 4F11 Heavy Variable + IgG1 Constant-protein |
| 28 | 4F11 Kappa Variable + Constant-nucleic acid |
| 29 | 4F11 Kappa Variable + Constant-protein |

Example 3: Binding Affinities

The binding affinity and kinetics of binding of antibody 4F11 to recombinant human Notch3 extracellular domain (containing EGF like domains 1-11) Fc fusion protein (rhNotch3-Fc (R&D Systems, Inc., Minneapolis, Minn.)) were measured by surface plasmon resonance using a Biacore® T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, according to a standard protocol. Analyses were performed at 25° C. and 37° C. using PBS containing 0.05% surfactant P20 as running buffer. The antibody was captured in individual flow cells at a flow rate of 10 µl/minute. Injection time was varied for each antibody to yield an Rmax between 30 and 60 resonance units (RU). Buffer or rhNotch3-Fc diluted in running buffer was injected sequentially over a reference surface (no antibody captured) and the active surface (antibody to be tested) for 240 seconds at 60 µl/minute. The dissociation phase was monitored for up to 1500 seconds. The surface was then regenerated with two 60-second injections of 10 mM Glycine-HCl, pH 2.25, at a flow rate of 30 µl/minute. The rhNotch3-Fc concentration range tested was 100 nM to 3.125 nM (2 fold dilution).

Kinetic parameters were determined using the kinetic function of the BIAevaluation software (GE Healthcare) with double reference subtraction. Kinetic parameters for the antibody, $k_a$ (association rate constant), $k_d$ (dissociation rate constant), and $K_D$ (equilibrium dissociation constant) were determined Kinetic values of the monoclonal antibody 4F11 on rhNotch3-Fc at 25° C. and 37° C. are summarized in Table 5.

TABLE 5

| Antibody Binding to rhNotch3-Fc | | | | |
|---|---|---|---|---|
| Temperature | $k_a$ (1/Ms) | $k_d$ (1/s) | $K_D$ (M) | n |
| 25° C. | 7.0E+04 | 4.8E−05 | 8.23E−10 | 3 |
| 37° C. | 7.5E+04 | 5.7E−05 | 7.8E−10 | 3 |

The data in Table 5 demonstrate that the antibody 4F11 binds rhNotch3-Fc with a $K_D$ of about 1 nM, 900 pM, 850 pM, 800 pM, 750 pM, 700 pM, 650 pM, 600 pM, 500 pM, 400 pM, 300 pM, 250 pM, or 200 pM or less.

Binding to cell surface human Notch3 by the antibody 4F11 was measured at 4° C., using Fluorescence Activated Cell Sorting (FACS). CHO N3 (Flp-In-CHO cells (Invitrogen) stably transfected with human Notch3), HCC2429 cells, and RL-952 cells expressing human Notch3 were washed once with PBS containing calcium chloride and magnesium chloride (Invitrogen) and harvested using cell dissociation buffer (Invitrogen). Cells were washed a second time with PBS and resuspended in FACS buffer (PBS with 0.5% BSA (Sigma-Aldrich)) for a final cell concentration of 250,000 cells per well into a 96-well v-bottom plate. Purified antibodies were diluted in FACS buffer over a concentration range of 100 nM to 0.1 nM. Cells were then incubated at 4° C. with 100 µl of antibody for one hour, washed with FACS buffer twice, and resuspended in 100 µl of goat-anti mouse PE-conjugated antibody (Jackson Immuno Research). Cells were incubated at 4° C. for 30 minutes in the dark, washed once with FACS buffer, and then analyzed using a Beckman Coulter Cytomics FC 500 instrument. The geometric mean of the florescent intensity was then calculated for each antibody concentration. These values were then entered into Prism software (GraphPad, La Jolla, Calif.) and used to generate a binding curve by plotting geometric mean versus antibody concentration. From the binding curve, the following equation was used to calculate the $K_D$ and $K_D$ range of 4F11 binding to human Notch3 on the cell surface of the three cell lines.

Equation: One Site Binding (Hyperbola)

$$Y=B_{max}*X/(K_D+X)$$

*describes the binding of a ligand to a receptor that follows the law of mass action. $B_{max}$ is the maximal binding, and $K_D$ is the concentration of ligand required to reach half-maximal binding.

Results are summarized in Table 6.

TABLE 6

| | $K_D$ (nM) | $K_D$ Range (nM) |
|---|---|---|
| CHO N3 | 0.36 | 0.21 to 0.51 |
| HCC2429 | 2.58 | 1.21 to 3.95 |
| RL-952 | 0.9633 | 0.7168 to 1.210 |

The results in Table 6 demonstrate that the antibody 4F11 binds cell surface Notch3 with a $K_D$ of about 1 nM, 750 pM, 650 pM, 600 pM, 500 pM, 400 pM, 300 pM, 250 pM, or 200 pM or less.

Example 4: Binding Specificity

Figure 4:
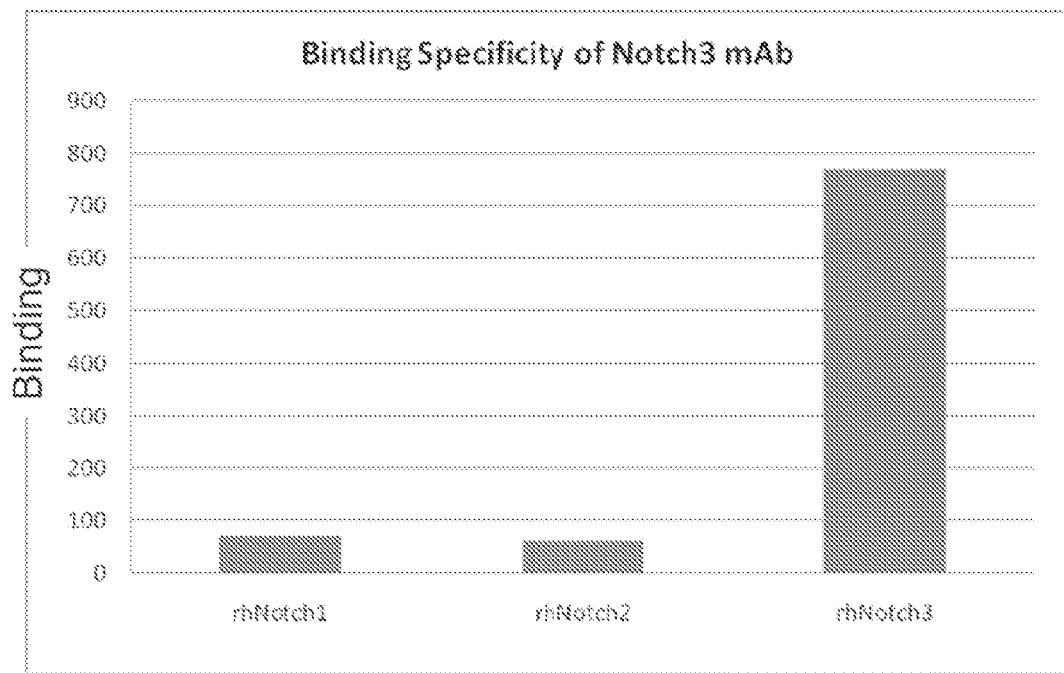
FIG. 4 is a bar chart summarizing results of an experiment to determine specificity of antibody 4F11 binding to Fc-bound recombinant human Notch3 (rhNotch3) using Octet. The results demonstrate that the binding specificity of the 4F11 antibody for rhNotch3 is much higher than for rhNotch1 or rhNotch2.
Figure 5A:
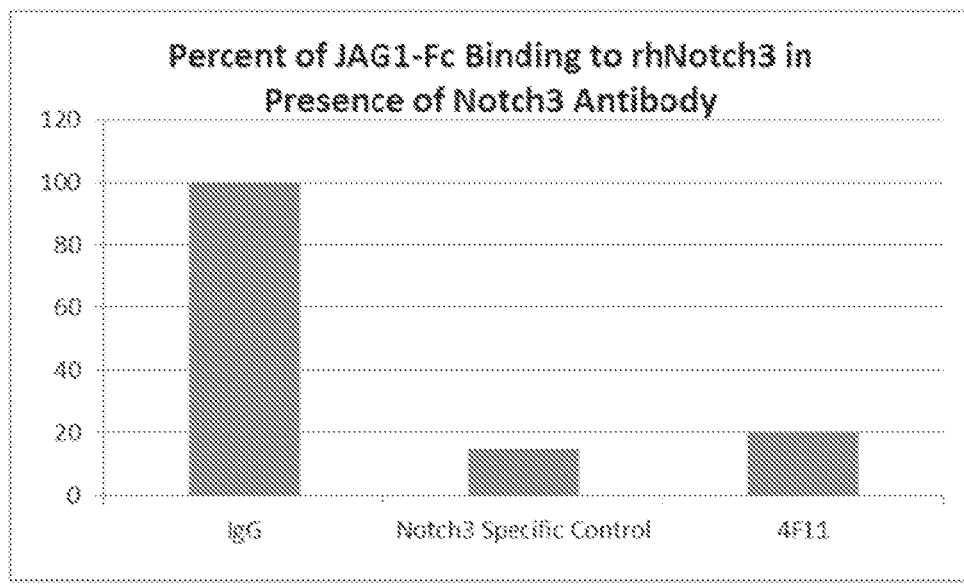
FIG. 5A is a bar chart illustrating the ability of antibody 4F11 to neutralize binding of the ligand Jag1 to human Notch3 protein. The chart shows that the antibody 4F11 and a Notch3 Specific Control, but not human immunoglobulin (hIgG), were able to block binding of recombinant human Fc-bound Jag1 (Jag1-Fc) to rhNotch3, as detected by biolayer interferometry (BLI).
Figure 5B:
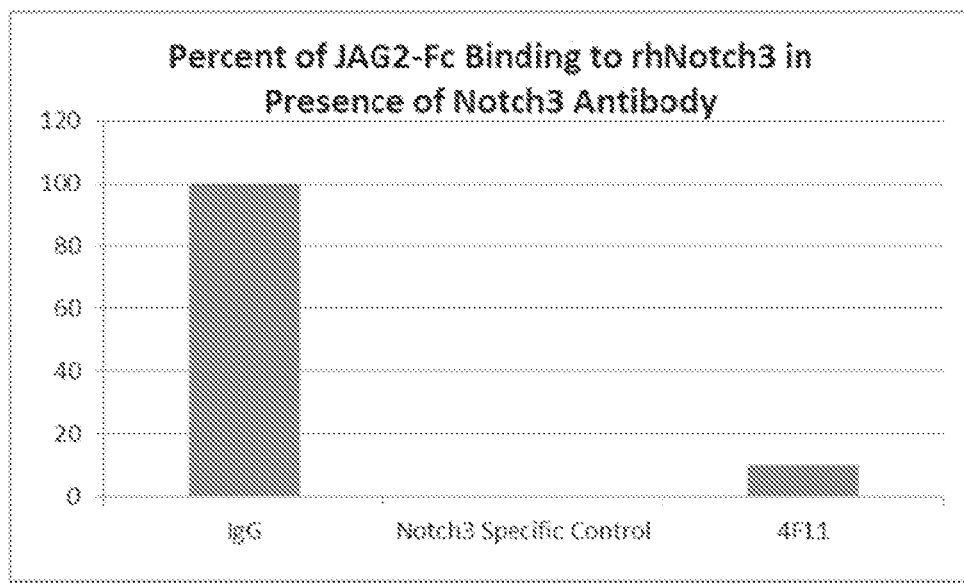
FIG. 5B is a bar chart illustrating the ability of antibody 4F11 to neutralize binding of the ligand Jag2 to human Notch3 protein. The chart shows that the antibody 4F11 and a Notch3 Specific Control, but not hIgG, were able to block binding of recombinant human Fc-bound Jag2 (Jag2-Fc) to rhNotch3, as detected by BLI.
Figure 5C:
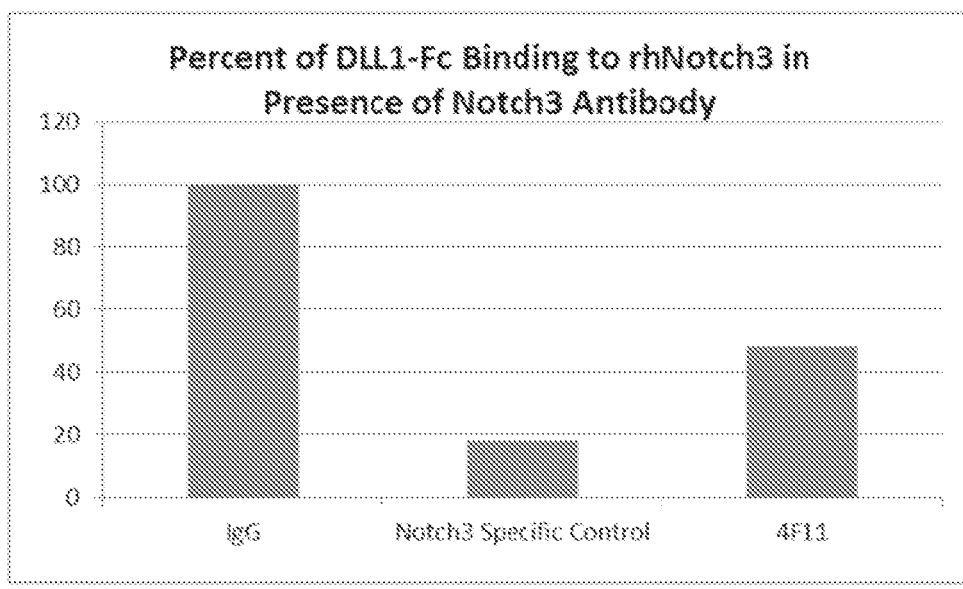
FIG. 5C is a bar chart illustrating the ability of antibody 4F11 to neutralize binding of the ligand DLL1 to human Notch3 protein. The chart shows that the antibody 4F11 and a Notch3 Specific Control, but not hIgG, block binding of recombinant human Fc-bound DLL1 (DLL1-Fc) to rhNotch3, to a greater extent than IgG, as detected by BLI.
Figure 5D:
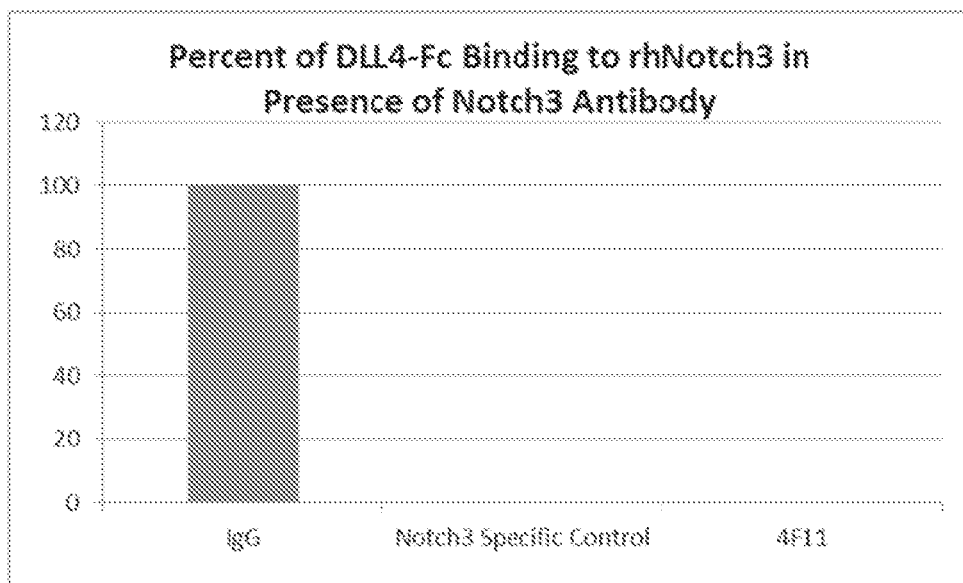
FIG. 5D is a bar chart illustrating the ability of antibody 4F11 to neutralize binding of the ligand DLL4 to human Notch3 protein. The chart shows that the antibody 4F11 and a Notch3 Specific Control, but not hIgG, were able to block binding of recombinant human Fc-bound DLL4 (DLL4-Fc) to rhNotch3, as detected by BLI.

Antibody 4F11 was tested for binding to human Notch1, human Notch2, or human Notch3 proteins. Binding measurements were made by biolayer interferometry (BLI), using a FortéBio Octet® QK instrument (FortéBio, Menlo Park, Calif.). Anti-human-Fc sensors were soaked in PBS containing 1 mg/ml BSA for five minutes prior to binding of antibodies. Then the following proteins (400 nM, in PBS containing 1 mg/ml BSA) were allowed to bind to the sensors: rhNotch1-Fc (R&D Systems, Minneapolis, Minn.; Cat. No. 3647-TK-050), rhNotch2-Fc (R&D Cat. No. 3735-NT-050), rhNotch3-Fc (R&D Cat. No. 1559-NT-050), or rmNotch3-Fc (R&D Cat. No. 1308-NT-050). Notch protein bound sensors were immersed in antibody solution (50 µg/ml) to allow binding of antibody to the Notch protein. Binding was detected by shifts in the interference pattern. These results demonstrated that the antibodies bind specifically to human Notch3 protein, but do not bind to human Notch2 or human Notch1 protein (FIG. 4).

Stable cells lines expressing Notch receptors were produced by transfecting FlpIn™ CHO or FlpIn™ 293 cells (Life Technologies, Grand Island, N.Y.) with full length human Notch1, Notch2, Notch3, or Notch4 cDNAs cloned into the pcDNASFRT vector using Lipofectamine 2000 (Life Technologies) according to the manufacturer's protocol. Twenty-four hours after transfection, CHO cells were split into F12 media containing 10% FBS, 2 mM L-Glutamine and 700 µg/ml hygromycin B (Sigma-Aldrich, St. Louis, Mo.) to select for transfected cells. 293 cells were split into DMEM media containing 10% FBS, 2 mM L-glutamine and 200 µg/ml hygromycin B. Expression of Notch receptors was confirmed by FACS analysis using anti-human Notch1 PE (BioLegend, San Diego, Calif.), anti-Notch2 PE (eBioscience, San Diego, Calif.), or anti-human Notch3 PE (BioLegend, San Diego, Calif.).

To determine specificity of binding to cell surface Notch proteins, antibody 4F11 was tested for binding to human Notch1, human Notch2, human Notch3 and human Notch4 expressed on the surface of CHO cells using electrochemiluminescence (Meso Scale Discovery). A CHO line lacking any human Notch protein was also produced for use as a negative control. Cells were grown under standard conditions (37° C., F12+10% FBS). For binding studies, cells were washed in PBS containing calcium and magnesium, and removed from the plate by treatment with Cell Dissociation Buffer (Life Technologies) for ten minutes at 37° C.

Cells were seeded at a density of 30,000 cells per well, in hybridoma media, instandard 96-well binding plates (Meso Scale Discovery, Cat. No. L15XA-6). Cells were incubated for one hour at 37° C. Antibodies or control IgG were added at 5 µg/ml, in 50 µl hybridoma media, and incubated for one hour at 37° C. The plates were washed twice with PBS containing 3% BSA. Binding of the antibodies to cell surface was detected using 2 µg/ml of MSD anti-mouse IgG secondary antibody (Meso Scale Discovery, Cat. No. R32AC-1) for one hour at 4° C. Plates were washed twice with PBS containing 3% BSA, and 150 µl of read buffer (Meso Scale Discovery Cat. No. R92TC-1) was added. The plates were analyzed on a Sector Imager 2400 instrument (Meso Scale Discovery). This analysis showed that antibody 4F11 binds to human Notch3 displayed on the surfaces of cells, but does not bind to human Notch1, Notch2, or Notch4 displayed on the surfaces of cells. The 4F11 antibody also does not bind CHO-EV (empty vector) cells that express endogenous hamster Notch proteins. These results indicated that antibody 4F11 binds specifically to human Notch3 protein displayed on a cell surface in vitro.

Example 5: Inhibition of Notch3-Ligand Binding

The 4F11 antibody was tested for its ability to inhibit the binding of rhNotch3 binding to human Jag1, Jag2, DLL1 and DLL4. Binding measurements were made by bio-layer interferometry (BLI), using a FortéBio Octet® QK instrument (FortéBio, Menlo Park, Calif.). The ligands tested were rhJag1-Fc (R&D Cat. No. 1277-JG-050), rhJag2-Fc (R&D Cat. No. 1726-JG-050), rhDLL1-Fc (R&D Cat. No. 5026-DL-050), and His tagged rhDLL4 (R&D Cat. No. 1506-D4-050).

To determine the degree of inhibition of Notch3-ligand binding by antibody 4F11, the Octet sensors were loaded with recombinant human Notch3, and the antibody was allowed to bind, as described in Example 4. In positive control samples, a commercially available Notch3 polyclonal antibody capable of blocking ligand binding to recombinant human Notch3 (Notch3 Specific Control) was used instead of the 4F11 antibody. Then sensors were immersed in 500 µg/ml human IgG, to block non-specific binding. Ligands were prepared at a concentration of 400 nM in PBS containing 3% BSA, and were allowed to bind. The on-rate and off-rate for ligand binding were detected using the Octet QK instrument and software. The 4F11 antibody blocked binding of all four ligands to rhNotch3-Fc (FIG. 5A-5D).

Example 6: Inhibition of Ligand-Induced Notch3 ICD Cleavage

Activation of Notch receptors results in cleavage of the Notch intracellular domain (NICD), which can be detected by Western blot. The effect of antibody 4F11 on the activation of Notch3 ICD cleavage was tested.

To create soluble Notch ligands, PCR was used to amplify sequences corresponding to the extracellular domains of human Jag1 or human Jag2 cDNA and fuse them in-frame to the coding sequence of human IgG Fc. This construct was then subcloned into the pEE14.4 expression vector (Lonza), transfected into CHOK1SV cells, and selected to produce stable cell lines that secrete hJag1-hFc or hJag2-hFc fusion protein. 96-well Immunosorp ELISA plates (Nalgene Nunc, Rochester, N.Y.) were coated with 5 µg/ml anti-human Fc (Jackson ImmunoResearch, West Grove, Pa.) overnight at 4° C. After washing wells with PBS/0.5% BSA, 5 µg/ml of soluble hJag1-hFc fusion protein was added and allowed to bind at room temperature for two hours. Unbound protein was removed by washing with PBS/0.5% BSA. FlpIn™ 293 cells engineered to express hNotch3 (as described in Example 4) were plated on Jag1-hFc ligand or hFc in the presence of 10 µg/ml 4F11 or mIgG control antibody. Cells were lysed 24 hours later in RIPA buffer (Boston BioProducts, Ashland, Mass.) containing protease inhibitors. Induction of cleaved NICD was detected by probing the blot with a Notch3 antibody against the C-terminus (Cell Signaling, Danvers, Mass.) that detects both full length protein and the cleaved ICD. Ligand-induced activation and Notch3 ICD cleavage was inhibited by antibody 4F11.

Example 7: Inhibition of Notch3-Dependent Transcription

Figure 6A:
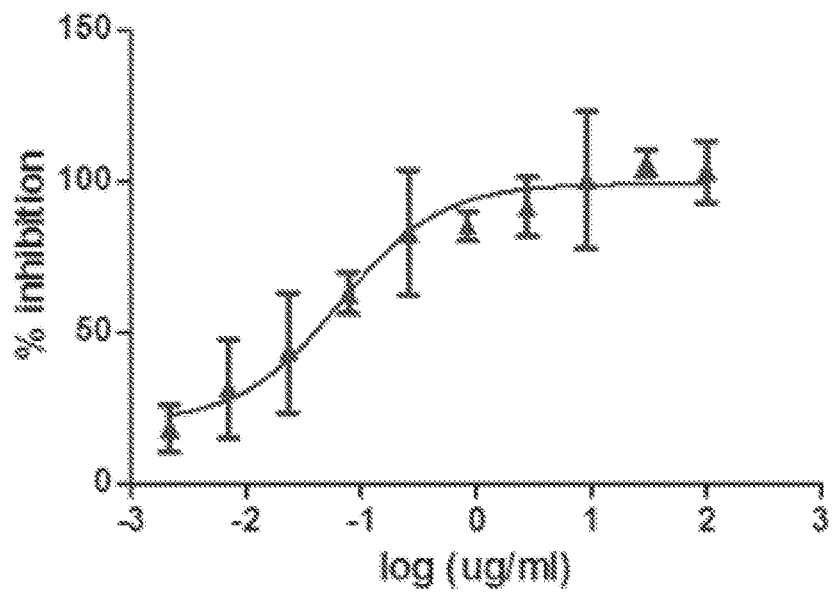
FIG. 6A is a dose-response curve summarizing results from a Notch3 reporter assay showing that antibody 4F11 inhibits Notch3-dependent reporter gene expression in the presence of the Fc-bound ligand Jag2 (Jag2-Fc). The graph shows the relationship between inhibition of Jag2-Fc-stimulated reporter activity (% Inhibition) by antibody 4F11 in transduced cells, in relation to the amount of Jag2-Fc ligand. Reporter activity of cells transduced with the RBP-Jκ-dependent luciferase reporter, exposed to any activating ligand, and treated with mouse IgG (mIgG) was defined as 100% activity for each ligand. Reporter activity of transduced cells not exposed to ligand but treated with mouse IgG was defined as 0% activity.
Figure 6B:
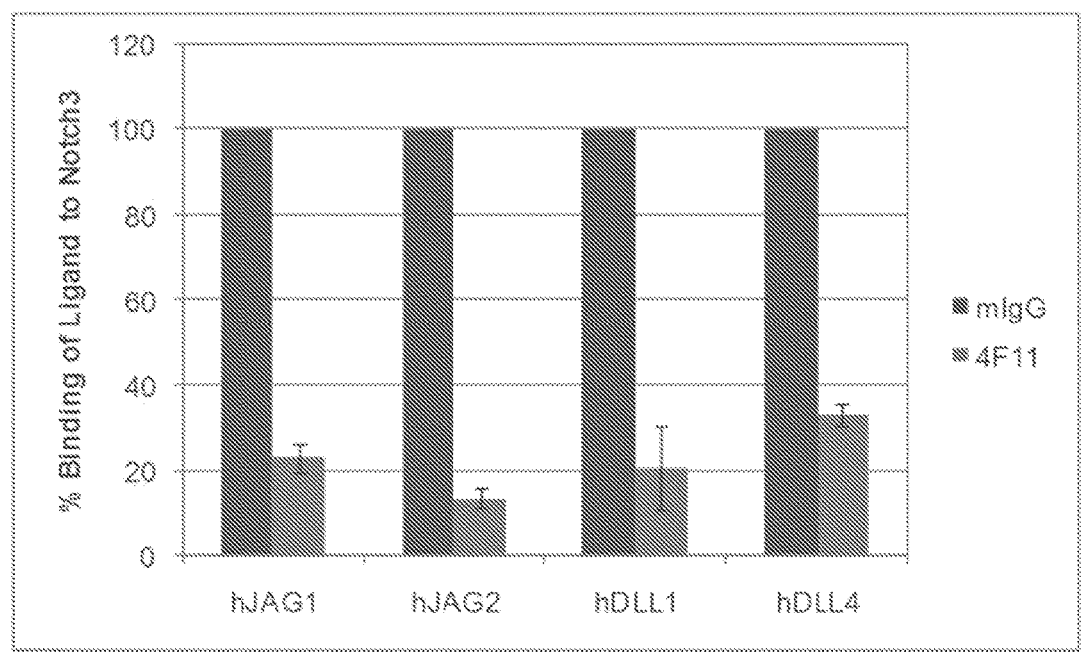
FIG. 6B is a bar chart summarizing results of Notch3 reporter assays showing that antibody 4F11, but not mouse IgG (mIgG), inhibits Notch3-dependent reporter gene expression induced by the ligands hJag1, hJag2, hDLL1 and hDLL4. Reporter activity of cells transduced with the RBP-Jκ-dependent luciferase reporter, exposed to any activating ligand, and treated with mouse IgG (mIgG) was defined as 100% activity for each ligand. Reporter activity of transduced cells not exposed to ligand but treated with mouse IgG was defined as 0% activity.

Reporter cell lines dependent upon Notch3 were produced by lentiviral introduction of a RBP-Jκ-dependent luciferase reporter gene (SABiosciences, Frederick, Md.) into 293-FlpIn Notch3 cells, RL95-2 endometrial cancer cells, HCC1143 breast cancer cells, and MDA-MB-468 breast cancer cells. To activate Notch3-dependent signaling and transcription, cells were plated on ligand-coated wells prepared as described in Example 6. Cells were pre-incubated with a 3-fold dilution series of Notch3 antibody concentrations ranging from 0-300 µg/ml, for one hour at 37° C., before seeding 100 µl of the suspension into 96-well plates coated with ligand or hFc. Cells were incubated in ligand-coated or human-Fc-coated wells for four or twenty-four hours at 37° C., in 5% $CO_2$. Next, 100 µl of Promega Bright Glo™ (Promega, Madison, Wis.) was added to each well. The reaction was allowed to proceed for five minutes in the dark, and then the entire 200 µl volume was transferred to white walled plates and read using a luminometer. Polyclonal antibodies against Notch1 (AF1057, R&D Systems), Notch2 (AF1190, R&D Systems) or Notch3 (AF1559, R&D Systems) were used as controls to confirm that ligand-stimulated reporter activity in each cell line was specifically dependent upon the introduced Notch receptor. As shown in FIG. 6A, Notch3 antibody 4F11 inhibited Notch3-dependent transcription stimulated by the ligand Jag2. Activation of Notch3-dependent transcription by each of the ligands Jag1, Jag2, DLL1, and DLL4 was also inhibited by the Notch3 antibody 4F11 (FIG. 6B and Table 7).

TABLE 7

| Ligand | Jag1 | Jag2 | DLL1 | DLL4 |
|---|---|---|---|---|
| EC$_{50}$ | 2.6 nM | 0.4 nM | 6.0 nM | 4.7 nM |
| Maximum Inhibition | 92% | 99% | 100% | 73% |

Example 8: Humanization of Anti-Notch3 Antibodies

This Example describes the humanization and chimerization of the anti-human Notch3 antibody 4F11, and the characterization of the resulting humanized antibodies. The humanized anti-Notch3 antibodies were designed, affinity matured by targeted CDR mutagenesis, and optimized using methods known in the art. The amino acid sequences were converted to codon-optimized DNA sequences and synthesized to include (in the following order): 5' HindIII restriction site, Kozak consensus sequence, amino terminal signal sequence, humanized variable region, human IgG1 or Kappa constant region, stop codon, and a 3' EcoRI restriction site.

Chimeric (murine variable region and human constant region) 4F11 heavy (human IgG1) and light (human Kappa) chains were also constructed. To generate chimeric antibodies, the murine variable regions were fused to the human constant region, and codon-optimized DNA sequences were synthesized, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using In-Fusion™ PCR cloning (Clontech, Mountain View, Calif.). The humanized and chimeric Kappa light chains were subcloned into pEE14.4 (Lonza) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to Notch3 was measured as described below. The results are summarized in Tables 14-16.

Exemplary combinations of the chimeric or humanized 4F11 immunoglobulin heavy chain and immunoglobulin light chain variable regions is set forth below in Table 8.

TABLE 8

| Antibody Name | Heavy Chain Variable Region | Light Chain Variable Region |
|---|---|---|
| Hu4F11-1 | Ch4F11 Chimeric Heavy (SEQ ID NO: 2) | Ch4F11 Chimeric Kappa (SEQ ID NO: 4) |
| Hu4F11-10 | Sh4F11 Hv3-23 Heavy (SEQ ID NO: 34) | Ch4F11 Chimeric Kappa (SEQ ID NO: 4) |
| Hu4F11-18 | Ch4F11 Chimeric Heavy (SEQ ID NO: 2) | Hu4F11 Kv2D-29 Kappa (SEQ ID NO: 44) |
| Hu4F11-32 | Sh4F11 Hv3-23 Heavy (SEQ ID NO: 34) | Hu4F11 Kv2D-29 Kappa (SEQ ID NO: 44) |
| Hu4F11-69 | Sh4F11 Hv3-23 A28T S31N T62S Heavy (SEQ ID NO: 40) | Hu4F11 Kv2D-29 N28H Kappa (SEQ ID NO: 46) |
| Hu4F11-70 | Sh4F11 Hv3-23 A28T S31H T62S Heavy (SEQ ID NO: 36) | Hu4F11 Kv2D-29 N28H Kappa (SEQ ID NO: 46) |
| Hu4F11-71 | Sh4F11 Hv3-23 A28T T62S Heavy (SEQ ID NO: 42) | Hu4F11 Kv2D-29 N28H Kappa (SEQ ID NO: 46) |
| Hu4F11-72 | Sh4F11 Hv3-23 S31H T62S Heavy (SEQ ID NO: 38) | Hu4F11 Kv2D-29 N28H Kappa (SEQ ID NO: 46) |
| Hu4F11-73 | Sh4F11 Hv3-23 A28T S31N T62S Heavy (SEQ ID NO: 40) | Hu4F11 Kv2D-29 N28Y Kappa (SEQ ID NO: 50) |
| Hu4F11-74 | Sh4F11 Hv3-23 A28T S31H T62S Heavy (SEQ ID NO: 36) | Hu4F11 Kv2D-29 N28Y Kappa (SEQ ID NO: 50) |
| Hu4F11-75 | Sh4F11 Hv3-23 A28T T62S Heavy (SEQ ID NO: 42) | Hu4F11 Kv2D-29 N28Y Kappa (SEQ ID NO: 50) |
| Hu4F11-76 | Sh4F11 Hv3-23 S31H T62S Heavy (SEQ ID NO: 38) | Hu4F11 Kv2D-29 N28Y Kappa (SEQ ID NO: 50) |
| Hu4F11-77 | Sh4F11 Hv3-23 A28T S31N T62S Heavy (SEQ ID NO: 40) | Hu4F11 Kv2D-29 N28Q Kappa (SEQ ID NO: 48) |
| Hu4F11-78 | Sh4F11 Hv3-23 A28T S31H T62S Heavy (SEQ ID NO: 36) | Hu4F11 Kv2D-29 N28Q Kappa (SEQ ID NO: 48) |
| Hu4F11-79 | Sh4F11 Hv3-23 A28T T62S Heavy (SEQ ID NO: 42) | Hu4F11 Kv2D-29 N28Q Kappa (SEQ ID NO: 48) |
| Hu4F11-80 | Sh4F11 Hv3-23 S31H T62S Heavy (SEQ ID NO: 38) | Hu4F11 Kv2D-29 N28Q Kappa (SEQ ID NO: 48) |

The nucleic acid sequences and the encoded protein sequences defining variable regions of the chimeric and humanized 4F11 antibodies are summarized below (amino terminal signal peptide sequences are not shown). CDR sequences (Kabat definition) are shown in bold and are underlined in the amino acid sequences.

Nucleic Acid Sequence Encoding the Ch4F11 Chimeric Heavy Chain Variable Region (SEQ ID NO:31)

```
  1 gaggtacagc ttgtcgagtc gggaggagga ttggtaaaac cgggtgggtc actcaaattg
 61 tcgtgtgcgg cgtcgggatt tgcgttttcg tcgtatgata tgtcgtgggt gcgccagacg
121 ccggaaaaac gattggaatg ggtcgcgtat atctcccgag ggggaggttc gacatactat
181 cccgacacgg tcaaagggcg cttcacgatt tcacgggaca atgcgaaaaa cacgctttat
241 cttcaaatgt cgtcgttgaa atcggaagat accgcgatgt attactgcgg gaggcatgcg
301 acgacggcgt attggtattt cgatgtgtgg ggagccggaa cgacggtgac ggtgtcgtcg
```

Protein Sequence Defining the Ch4F11 Chimeric Heavy Chain Variable Region (SEQ ID NO:2)

```
  1 evqlvesggg lvkpggslkl scaasgfafs sydmswvrqt pekrlewvay isrgggstyy
 61 pdtvkgrfti srdnakntly lqmsslksed tamyycgrha ttaywyfdvw gagttvtvss
```

Nucleic Acid Sequence Encoding the Sh4F11 Hv3-23 Heavy Chain Variable Region (SEQ ID NO:33)

```
  1 gaagtacagt tgttggagtc aggaggaggg ttggtccagc cgggtggatc gttgcggctt
 61 tcgtgtgcgg cgtcgggatt cgcgttttca tcgtatgaca tgtcgtgggt gaggcaggca
121 ccggggaaag gcttgaatg ggtatcgtac atttcgagag ggggaggatc gacgtattac
181 ccggatacgg tgaaaggaag gtttacgatc tcgcgcgaca attcaaagaa tacgctttat
241 cttcagatga actcgctccg agcggaagat acggcggtat actattgcgg tcgccatgcg
301 acgacggcgt attggtattt cgatgtgtgg ggacaaggga cgatggtcac ggtgtcgtcg
```

Protein Sequence Defining the Sh4F11 Hv3-23 Heavy Chain Variable Region (SEQ ID NO:34)

```
  1 evqllesggg lvqpggslrl scaasgfafs sydmswvrqa pgkglewvsy isrgggstyy
 61 pdtvkgrfti srdnskntly lqmnslraed tavyycgrha ttaywyfdvw gqgtmvtvss
```

Nucleic Acid Sequence Encoding the Sh4F11 Hv3-23 A28T S31H T62S Heavy Chain Variable Region (SEQ ID NO:35)

```
  1 gaagtacagt tgttggagtc aggaggaggg ttggtccagc cgggtggatc gttgcggctt
 61 tcgtgtgcgg cgtcgggatt caccttttca cactatgaca tgtcgtgggt gaggcaggca
121 ccggggaaag gcttgaatg ggtatcgtac atttcgagag ggggaggatc gacgtattac
181 ccggattccg tgaaaggaag gtttacgatc tcgcgcgaca attcaaagaa tacgctttat
241 cttcagatga actcgctccg agcggaagat acggcggtat actattgcgg tcgccatgcg
301 acgacggcgt attggtattt cgatgtgtgg ggacaaggga cgatggtcac ggtgtcgtcg
```

Protein Sequence Defining the Sh4F11 Hv3-23 A28T S31H T62S Heavy Chain Variable Region (SEQ ID NO:36)

```
  1 evqllesggg lvqpggslrl scaasgftfs hydmswvrqa pgkglewvsy isrgggstyy
 61 pdsvkgrfti srdnskntly lqmnslraed tavyycgrha ttaywyfdvw gqgtmvtvss
```

Nucleic Acid Sequence Encoding the Sh4F11 Hv3-23 S31H T62S Heavy Chain Variable Region (SEQ ID NO:37)

```
  1 gaagtacagt tgttggagtc aggaggaggg ttggtccagc cgggtggatc gttgcggctt
 61 tcgtgtgcgg cgtcgggatt cgcgttttca cactatgaca tgtcgtgggt gaggcaggca
121 ccggggaaag gcttgaatg ggtatcgtac atttcgagag ggggaggatc gacgtattac
181 ccggattccg tgaaaggaag gtttacgatc tcgcgcgaca attcaaagaa tacgctttat
241 cttcagatga actcgctccg agcggaagat acggcggtat actattgcgg tcgccatgcg
301 acgacggcgt attggtattt cgatgtgtgg ggacaaggga cgatggtcac ggtgtcgtcg
```

Protein Sequence Defining the Sh4F11 Hv3-23 S31H T62S Heavy Chain Variable Region (SEQ ID NO:38)

```
 1 evqllesggg lvqpggslrl scaasgfafs hydmswvrqa pgkglewvsy isrgggstyy
61 pdsvkgrfti srdnskntly lqmnslraed tavyycgrha ttaywyfdvw gqgtmvtvss
```

Nucleic Acid Sequence Encoding the Sh4F11 Hv3-23 A28T S31N T62S Heavy Chain Variable Region (SEQ ID NO:39)

```
  1gaagtacagt tgttggagtc aggaggaggg ttggtccagc cgggtggatc gttgcggctt
 61tcgtgtgcgg cgtcgggatt ccctttttca aactatgaca tgtcgtgggt gaggcaggca
121ccggggaaag gcttgaatg gtatcgtac atttcgagag ggggaggatc gacgtattac
181ccggattccg tgaaaggaag gtttacgatc tcgcgcgaca attcaaagaa tacgctttat
241cttcagatga actcgctccg agcggaagat acggcggtat actattgcgg tcgccatgcg
301acgacggcgt attggtattt cgatgtgtgg ggacaaggga cgatggtcac ggtgtcgtcg
```

Protein Sequence Defining the Sh4F11 Hv3-23 A28T S31N T62S Heavy Chain Variable Region (SEQ ID NO:40)

```
 1 evqllesggg lvqpggslrl scaasgftfs nydmswvrqa pgkglewvsy isrgggstyy
61 pdsvkgrfti srdnskntly lqmnslraed tavyycgrha ttaywyfdvw gqgtmvtvss
```

Nucleic Acid Sequence Encoding the Sh4F11 Hv3-23 A28T T62S Heavy Chain Variable Region (SEQ ID NO:41)

```
  1gaagtacagt tgttggagtc aggaggaggg ttggtccagc cgggtggatc gttgcggctt
 61tcgtgtgcgg cgtcgggatt ccctttttca tcgtatgaca tgtcgtgggt gaggcaggca
121ccggggaaag gcttgaatg gtatcgtac atttcgagag ggggaggatc gacgtattac
181ccggattccg tgaaaggaag gtttacgatc tcgcgcgaca attcaaagaa tacgctttat
241cttcagatga actcgctccg agcggaagat acggcggtat actattgcgg tcgccatgcg
301acgacggcgt attggtattt cgatgtgtgg ggacaaggga cgatggtcac ggtgtcgtcg
```

Protein Sequence Defining the Sh4F11 Hv3-23 A28T T62S Heavy Chain Variable Region (SEQ ID NO:42)

```
 1 evqllesggg lvqpggslrl scaasgftfs sydmswvrqa pgkglewvsy isrgggstyy
61 pdsvkgrfti srdnskntly lqmnslraed tavyycgrha ttaywyfdvw gqgtmvtvss
```

Nucleic Acid Sequence Encoding the Ch4F11 Chimeric Kappa Chain Variable Region (SEQ ID NO:32)

```
  1gacgtggtaa tgacgcagac gccgttgtcc cttcctgtct cgctcggaga tcaggcgtcg
 61atctcgtgta aagctcgca gtcactcgtc cataccaacg gaatacata tcttcactgg
121tatttgcaaa agcccggaca gtcaccgaag ctcttgatct acaaagtatc caatcggttt
181tcggggggtgc ccgaccgatt ctcgggatcg ggttcgggga cggattttac gttgaagatt
241tcgcgggtgg aagcggagga tctcggtgtc tacttttgtt cgcagtcaac gcatgtcccg
301tggacgttcg gaggcgggac aaaacttgag atcaag
```

Protein Sequence Defining the Ch4F11 Chimeric Kappa
Chain Variable Region (SEQ ID NO:4)

```
  1 dvvmtqtpls lpvslgdqas iscrssqslv htngntylhw ylqkpgqspk lliykvsnrf
 61 sgvpdrfsgs gsgtdftlki srveaedlgv yfcsqsthvp wtfgggtkle ik
```

Nucleic Acid Sequence Encoding the Hu4F11 Kv2D-29
Kappa Chain Variable Region (SEQ ID NO:43)

```
  1 gatgtagtca tgacccaaac gccgctttcg ttgtcggtga cgcccggaca gcccgcgtca
 61 atctcgtgtc ggtcatcgca gtcgttggta cacacaaacg gtaatacgta tctccattgg
121 tatctccaga agcccggcca gtcgccgcag ctcttgatct acaaagtgag caatcgcttt
181 tcggggggtgc cggatcggtt ctcgggatcg gggtcaggaa cggacttcac gcttaagatt
241 tcgagggtcg aggcggagga tgtcggagtc tactttttgtt cgcagtccac acatgtcccc
301 tggacgtttg ggcaggggac gaaggtggaa atcaag
```

Protein Sequence Defining the Hu4F11 Kv2D-29 Kappa
Chain Variable Region (SEQ ID NO:44)

```
  1 dvvmtqtpls lsvtpgqpas iscrssqslv htngntylhw ylqkpgqspq lliykvsnrf
 61 sgvpdrfsgs gsgtdftlki srveaedvgv yfcsqsthvp wtfgqgtkve ik
```

Nucleic Acid Sequence Encoding the Hu4F11 Kv2D-29
N28H Kappa Chain Variable Region (SEQ ID NO:45)

```
  1 gatgtagtca tgacccaaac gccgctttcg ttgtcggtga cgcccggaca gcccgcgtca
 61 atctcgtgtc ggtcatcgca gtcgttggta cacacacacg gtaatacgta tctccattgg
121 tatctccaga agcccggcca gtcgccgcag ctcttgatct acaaagtgag caatcgcttt
181 tcggggggtgc cggatcggtt ctcgggatcg gggtcaggaa cggacttcac gcttaagatt
241 tcgagggtcg aggcggagga tgtcggagtc tactttttgtt cgcagtccac acatgtcccc
301 tggacgtttg ggcaggggac gaaggtggaa atcaag
```

Protein Sequence Defining the Hu4F11 Kv2D-29 N28H
Kappa Chain Variable Region (SEQ ID NO:46)

```
  1 dvvmtqtpls lsvtpgqpas iscrssqslv hthgntylhw ylqkpgqspq lliykvsnrf
 61 sgvpdrfsgs gsgtdftlki srveaedvgv yfcsqsthvp wtfgqgtkve ik
```

Nucleic Acid Sequence Encoding the Hu4F11 Kv2D-29
N28Q Kappa Chain Variable Region (SEQ ID NO:47)

```
  1 gatgtagtca tgacccaaac gccgctttcg ttgtcggtga cgcccggaca gcccgcgtca
 61 atctcgtgtc ggtcatcgca gtcgttggta cacacaaag gtaatacgta tctccattgg
121 tatctccaga agcccggcca gtcgccgcag ctcttgatct acaaagtgag caatcgcttt
181 tcggggggtgc cggatcggtt ctcgggatcg gggtcaggaa cggacttcac gcttaagatt
241 tcgagggtcg aggcggagga tgtcggagtc tactttttgtt cgcagtccac acatgtcccc
301 tggacgtttg ggcaggggac gaaggtggaa atcaag
```

Protein Sequence Defining the Hu4F11 Kv2D-29 N28Q
Kappa Chain Variable Region (SEQ ID NO:48)

```
  1 dvvmtqtpls lsvtpgqpas iscrssqslv htqgntylhw ylqkpgqspq lliykvsnrf
 61 sgvpdrfsgs gsgtdftlki srveaedvgv yfcsgsthvp wtfgqgtkve ik
```

Nucleic Acid Sequence Encoding the Hu4F11 Kv2D-29
N28Y Kappa Chain Variable Region (SEQ ID NO:49)

```
  1 gatgtagtca tgacccaaac gccgctttcg ttgtcggtga cgcccggaca gcccgcgtca
 61 atctcgtgtc ggtcatcgca gtcgttggta cacacatacg gtaatacgta tctccattgg
121 tatctccaga agcccggcca gtcgccgcag ctcttgatct acaaagtgag caatcgcttt
181 tcggggtgc cggatcggtt ctcgggatcg gggtcaggaa cggacttcac gcttaagatt
241 tcgagggtcg aggcggagga tgtcggagtc tactttgttt cgcagtccac acatgtcccc
301 tggacgtttg gcaggggac gaaggtggaa atcaag
```

Protein Sequence Defining the Hu4F11 Kv2D-29 N28Y
Kappa Chain Variable Region (SEQ ID NO:50)

```
  1 dvvmtqtpls lsvtpgqpas iscrssqslv htygntylhw ylqkpgqspq lliykvsnrf
 61 sgvpdrfsgs gsgtdftlki srveaedvgv yfcsqsthvp wtfgqgtkve ik
```

The amino acid sequences defining the immunoglobulin heavy chain variable regions for the antibodies produced in Example 8 are aligned in FIG. 7. Amino terminal signal peptide sequences (for proper expression/secretion) are not shown. CDR$_1$, CDR$_2$, and CDR$_3$ (Kabat definition) are identified by boxes. FIG. 8 show an alignment of the separate CDR$_1$, CDR$_2$, and CDR$_3$ sequences for each of the variable region sequences shown in FIG. 7.

The amino acid sequences defining the immunoglobulin light chain variable regions for the antibodies in Example 8 are aligned in FIG. 9. Amino terminal signal peptide sequences (for proper expression/secretion) are not shown. CDR$_1$, CDR$_2$ and CDR$_3$ are identified by boxes. FIG. 10 shows an alignment of the separate CDR$_1$, CDR$_2$, and CDR$_3$ sequences for each of the variable region sequences shown in FIG. 9.

Table 9 is a concordance chart showing the SEQ ID NO. of each sequence discussed in this Example.

TABLE 9

| SEQ. ID NO. | Nucleic Acid or Protein |
|---|---|
| 31 | Ch4F11 Chimeric Heavy Chain Variable Region-nucleic acid |
| 2 | Ch4F11 Chimeric Heavy Chain Variable Region-protein |
| 5 | Ch4F11 Chimeric Heavy Chain CDR$_1$ |
| 6 | Ch4F11 Chimeric Heavy Chain CDR$_2$ |
| 7 | Ch4F11 Chimeric Heavy Chain CDR$_3$ |
| 33 | Sh4F11 Hv3-23 Heavy Chain Variable Region-nucleic acid |
| 34 | Sh4F11 Hv3-23 Heavy Chain Variable Region-protein |
| 5 | Sh4F11 Hv3-23 Heavy Chain CDR$_1$ |
| 6 | Sh4F11 Hv3-23 Heavy Chain CDR$_2$ |
| 7 | Sh4F11 Hv3-23 Heavy Chain CDR$_3$ |
| 35 | Sh4F11 Hv3-23 A28T S31H T62S Heavy Chain Variable Region-nucleic acid |
| 36 | Sh4F11 Hv3-23 A28T S31H T62S Heavy Chain Variable Region-protein |
| 51 | Sh4F11 Hv3-23 A28T S31H T62S Heavy Chain CDR1 |
| 53 | Sh4F11 Hv3-23 A28T S31H T62S Heavy Chain CDR$_2$ |
| 7 | Sh4F11 Hv3-23 A28T S31H T62S Heavy Chain CDR$_3$ |

TABLE 9-continued

| SEQ. ID NO. | Nucleic Acid or Protein |
|---|---|
| 37 | Sh4F11 Hv3-23 S31H T62S Heavy Chain Variable Region-nucleic acid |
| 38 | Sh4F11 Hv3-23 S31H T62S Heavy Chain Variable Region-protein |
| 51 | Sh4F11 Hv3-23 S31H T62S Heavy Chain CDR$_1$ |
| 53 | Sh4F11 Hv3-23 S31H T62S Heavy Chain CDR$_2$ |
| 7 | Sh4F11 Hv3-23 S31H T62S Heavy Chain CDR$_3$ |
| 39 | Sh4F11 Hv3-23 A28T S31N T62S Heavy Chain Variable Region-nucleic acid |
| 40 | Sh4F11 Hv3-23 A28T S31N T62S Heavy Chain Variable Region-protein |
| 52 | Sh4F11 Hv3-23 A28T S31N T62S Heavy Chain CDR$_1$ |
| 53 | Sh4F11 Hv3-23 A28T S31N T62S Heavy Chain CDR$_2$ |
| 7 | Sh4F11 Hv3-23 A28T S31N T62S Heavy Chain CDR$_3$ |
| 41 | Sh4F11 Hv3-23 A28T T62S Heavy Chain Variable Region-nucleic acid |
| 42 | Sh4F11 Hv3-23 A28T T62S Heavy Chain Variable Region-protein |
| 5 | Sh4F11 Hv3-23 A28T T62S Heavy Chain CDR$_1$ |
| 53 | Sh4F11 Hv3-23 A28T T62S Heavy Chain CDR$_2$ |
| 7 | Sh4F11 Hv3-23 A28T T62S Heavy Chain CDR$_3$ |
| 32 | Ch4F11 Chimeric Light (kappa) Chain Variable Region-nucleic acid |
| 4 | Ch4F11 Chimeric Light (kappa) Chain Variable Region-protein |
| 8 | Ch4F11 Chimeric Light (kappa) Chain CDR$_1$ |
| 9 | Ch4F11 Chimeric Light (kappa) Chain CDR$_2$ |
| 10 | Ch4F11 Chimeric Light (kappa) Chain CDR$_3$ |
| 43 | Hu4F11 Kv2D-29 Light (kappa) Chain Variable Region-nucleic acid |
| 44 | Hu4F11 Kv2D-29 Light (kappa) Chain Variable Region-protein |
| 8 | Hu4F11 Kv2D-29 Light (kappa) Chain CDR$_1$ |
| 9 | Hu4F11 Kv2D-29 Light (kappa) Chain CDR$_2$ |
| 10 | Hu4F11 Kv2D-29 Light (kappa) Chain CDR$_3$ |
| 45 | Hu4F11 Kv2D-29 N28H Light (kappa) Chain Variable Region-nucleic acid |
| 46 | Hu4F11 Kv2D-29 N28H Light (kappa) Chain Variable Region-protein |
| 62 | Hu4F11 Kv2D-29 N28H Light (kappa) Chain CDR$_1$ |
| 9 | Hu4F11 Kv2D-29 N28H Light (kappa) Chain CDR$_2$ |

TABLE 9-continued

| SEQ. ID NO. | Nucleic Acid or Protein |
|---|---|
| 10 | Hu4F11 Kv2D-29 N28H Light (kappa) Chain CDR$_3$ |
| 47 | Hu4F11 Kv2D-29 N28Q Light (kappa) Chain Variable Region-nucleic acid |
| 48 | Hu4F11 Kv2D-29 N28Q Light (kappa) Chain Variable Region-protein |
| 63 | Hu4F11 Kv2D-29 N28Q Light (kappa) Chain CDR$_1$ |
| 9 | Hu4F11 Kv2D-29 N28Q Light (kappa) Chain CDR$_2$ |
| 10 | Hu4F11 Kv2D-29 N28Q Light (kappa) Chain CDR$_3$ |
| 49 | Hu4F11 Kv2D-29 N28Y Light (kappa) Chain Variable Region-nucleic acid |
| 50 | Hu4F11 Kv2D-29 N28Y Light (kappa) Chain Variable Region-protein |
| 64 | Hu4F11 Kv2D-29 N28Y Light (kappa) Chain CDR$_1$ |
| 9 | Hu4F11 Kv2D-29 N28Y Light (kappa) Chain CDR$_2$ |
| 10 | Hu4F11 Kv2D-29 N28Y Light (kappa) Chain CDR$_3$ |

Humanized monoclonal antibody heavy chain CDR sequences (Kabat, Chothia, and IMGT definitions) are shown in Table 10.

TABLE 10

| | CDR1 | CRD2 | CDR3 | Variable Region SEQ ID NO: |
|---|---|---|---|---|
| Kabat | | | | |
| Ch4F11 Chimeric | SYDMS (SEQ ID NO: 5) | YISRGGGSTYYPDTVKG (SEQ ID NO: 6) | HATTAYWYFDV (SEQ ID NO: 7) | 2 |
| Sh4F11 Hv3-23 | SYDMS (SEQ ID NO: 5) | YISRGGGSTYYPDTVKG (SEQ ID NO: 6) | HATTAYWYFDV (SEQ ID NO: 7) | 34 |
| Sh4F11 Hv3-23 A28T S31H T62S | HYDMS (SEQ ID NO: 51) | YISRGGGSTYYPDSVKG (SEQ ID NO: 53) | HATTAYWYFDV (SEQ ID NO: 7) | 36 |
| Sh4F11 Hv3-23 S31H T62S | HYDMS (SEQ ID NO: 51) | YISRGGGSTYYPDSVKG (SEQ ID NO: 53) | HATTAYWYFDV (SEQ ID NO: 7) | 38 |
| Sh4F11 Hv3-23 A28T S31N T62S | NYDMS (SEQ ID NO: 52) | YISRGGGSTYYPDSVKG (SEQ ID NO: 53) | HATTAYWYFDV (SEQ ID NO: 7) | 40 |
| Sh4F11 Hv3-23 A28T T62S | SYDMS (SEQ ID NO: 5) | YISRGGGSTYYPDSVKG (SEQ ID NO: 53) | HATTAYWYFDV (SEQ ID NO: 7) | 42 |
| Chothia | | | | |
| Ch4F11 Chimeric | GFAFSSY (SEQ ID NO: 11) | SRGGGS (SEQ ID NO: 12) | HATTAYWYFDV (SEQ ID NO: 7) | 2 |
| Sh4F11 Hv3-23 | GFAFSSY (SEQ ID NO: 11) | SRGGGS (SEQ ID NO: 12) | HATTAYWYFDV (SEQ ID NO: 7) | 34 |
| Sh4F11 Hv3-23 A28T S31H T62S | GFTFSHY (SEQ ID NO: 54) | SRGGGS (SEQ ID NO: 12) | HATTAYWYFDV (SEQ ID NO: 7) | 36 |
| Sh4F11 Hv3-23 S31H T62S | GFAFSHY (SEQ ID NO: 55) | SRGGGS (SEQ ID NO: 12) | HATTAYWYFDV (SEQ ID NO: 7) | 38 |
| Sh4F11 Hv3-23 A28T S31N T62S | GFTFSNY (SEQ ID NO: 56) | SRGGGS (SEQ ID NO: 12) | HATTAYWYFDV (SEQ ID NO: 7) | 40 |
| Sh4F11 Hv3-23 A28T T62S | GFTFSNY (SEQ ID NO: 57) | SRGGGS (SEQ ID NO: 12) | HATTAYWYFDV (SEQ ID NO: 7) | 42 |
| IMGT | | | | |
| Ch4F11 Chimeric | GFAFSSYD (SEQ ID NO: 14) | ISRGGGST (SEQ ID NO: 15) | GRHATTAYWYFDV (SEQ ID NO: 16) | 2 |
| Sh4F11 Hv3-23 | GFAFSSYD (SEQ ID NO: 14) | ISRGGGST (SEQ ID NO: 15) | GRHATTAYWYFDV (SEQ ID NO: 16) | 34 |

TABLE 10-continued

| | CDR1 | CRD2 | CDR3 | Variable Region SEQ ID NO: |
|---|---|---|---|---|
| Sh4F11 Hv3-23 A28T S31H T62S | GFTFSHYD (SEQ ID NO: 58) | ISRGGGST (SEQ ID NO: 15) | GRHATTAYWYFDV (SEQ ID NO: 16) | 36 |
| Sh4F11 Hv3-23 S31H T62S | GFAFSHYD (SEQ ID NO: 59) | ISRGGGST (SEQ ID NO: 15) | GRHATTAYWYFDV (SEQ ID NO: 16) | 38 |
| Sh4F11 Hv3-23 A28T S31N T62S | GFTFSNYD (SEQ ID NO: 60) | ISRGGGST (SEQ ID NO: 15) | GRHATTAYWYFDV (SEQ ID NO: 16) | 40 |
| Sh4F11 Hv3-23 A28T T62S | GFTFSSYD (SEQ ID NO: 61) | ISRGGGST (SEQ ID NO: 15) | GRHATTAYWYFDV (SEQ ID NO: 16) | 42 |

Humanized monoclonal antibody Kappa light chain CDR sequences (Kabat, Chothia, and IMGT definitions) are shown in Table 11.

TABLE 11

| | CDR1 | CRD2 | CDR3 | Variable Region SEQ ID NO: |
|---|---|---|---|---|
| Kabat/Chothia | | | | |
| Ch4F11 Chimeric | RSSQSLVHTNGNTYLH (SEQ ID NO: 8) | KVSNRFS (SEQ ID NO: 9) | SQSTHVPWT (SEQ ID NO: 10) | 4 |
| Hu4F11 Kv2D-29 | RSSQSLVHTNGNTYLH (SEQ ID NO: 8) | KVSNRFS (SEQ ID NO: 9) | SQSTHVPWT (SEQ ID NO: 10) | 44 |
| Hu4F11 Kv2D-29 N28H | RSSQSLVHTHGNTYLH (SEQ ID NO: 62) | KVSNRFS (SEQ ID NO: 9) | SQSTHVPWT (SEQ ID NO: 10) | 46 |
| Hu4F11 Kv2D-29 N28Q | RSSQSLVHTQGNTYLH (SEQ ID NO: 63) | KVSNRFS (SEQ ID NO: 9) | SQSTHVPWT (SEQ ID NO: 10) | 48 |
| Hu4F11 Kv2D-29 N28Y | RSSQSLVHTYGNTYLH (SEQ ID NO: 64) | KVSNRFS (SEQ ID NO: 9) | SQSTHVPWT (SEQ ID NO: 10) | 50 |
| IMGT | | | | |
| Ch4F11 Chimeric | QSLVHTNGNTY (SEQ ID NO: 20) | KVS | SQSTHVPWT (SEQ ID NO: 10) | 4 |
| Hu4F11 Kv2D-29 | QSLVHTNGNTY (SEQ ID NO: 20) | KVS | SQSTHVPWT (SEQ ID NO: 10) | 44 |
| Hu4F11 Kv2D-29 N28H | QSLVHTHGNTY (SEQ ID NO: 65) | KVS | SQSTHVPWT (SEQ ID NO: 10) | 46 |
| Hu4F11 Kv2D-29 N28Q | QSLVHTQGNTY (SEQ ID NO: 66) | KVS | SQSTHVPWT (SEQ ID NO: 10) | 48 |
| Hu4F11 Kv2D-29 N28Y | QSLVHTYGNTY (SEQ ID NO: 67) | KVS | SQSTHVPWT (SEQ ID NO: 10) | 50 |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO:68)

```
  1 gcctcaacaa aaggaccaag tgtgttccca ctcgccccta gcagcaagag tacatccggg
 61 ggcactgcag cactcggctg cctcgtcaag gattattttc cagagccagt aaccgtgagc
121 tggaacagtg gagcactcac ttctggtgtc catactttc ctgctgtcct gcaaagctct
181 ggcctgtact cactcagctc cgtcgtgacc gtgccatctt catctctggg cactcagacc
241 tacatctgta atgtaaacca caagcctagc aatactaagg tcgataagcg ggtggaaccc
301 aagagctgcg acaagactca cacttgtccc ccatgccctg ccctgaact tctgggcggt
361 cccagcgtct ttttgttccc accaaagcct aaagatactc tgatgataag tagaacaccc
421 gaggtgacat gtgttgttgt agacgtttcc cacgaggacc cagaggttaa gttcaactgg
481 tacgttgatg gagtcgaagt acataatgct aagaccaagc ctagagagga gcagtataat
541 agtacatacc gtgtagtcag tgttctcaca gtgctgcacc aagactggct caacggcaaa
601 gaatacaaat gcaaagtgtc caacaaagca ctcccagccc ctatcgaaa gactattagt
661 aaggcaaagg ggcagcctcg tgaaccacag gtgtacactc tgccacccag tagagaggaa
721 atgacaaaga accaagtctc attgacctgc ctggtgaaag gcttctaccc cagcgacatc
781 gccgttgagt gggagagtaa cggtcagcct gagaacaatt acaagacaac cccccagtg
841 ctggatagtg acgggtcttt ctttctgtac agtaagctga ctgtggacaa gtcccgctgg
901 cagcagggta acgtcttcag ctgttccgtg atgcacgagg cattgcacaa ccactacacc
961 cagaagtcac tgagcctgag cccagggaag
```

Protein Sequence Defining the Human IgG1 Heavy Chain Constant Region (SEQ ID NO:69)

```
  1 astkgpsvfp lapssktstsg gtaalgclvk dyfpepvtvs wnsgaltsgv htfpavlqss
 61 glyslssvvt vpssslgtqt yicnvnhkps ntkvdkrvep kscdkthtcp pcpapellgg
121 psvflfppkp kdtlmisrtp evtcvvvdvs hedpevkfnw yvdgvevhna ktkpreeqyn
181 styrvvsvlt vlhqdwlngk eykckvsnka lpapiektis kakgqprepq vytlppsree
241 mtknqvsltc lvkgfypsdi avewesngqp ennykttppv ldsdgsffly skltvdksrw
301 qqgnvfscsv mhealhnhyt qkslslspgk
```

Nucleic Acid Sequence Encoding the Human Kappa Light Chain Constant Region (Version 1) (SEQ ID NO:70)

```
  1 cgcacagttg ctgcccccag cgtgttcatt ttcccaccta gcgatgagca gctgaaaagc
 61 ggtactgcct ctgtcgtatg cttgctcaac aacttttacc cacgtgaggc taaggtgcag
121 tggaaagtgg ataatgcact tcaatctgga aacagtcaag agtccgtgac agaacaggac
181 agcaaagact caacttattc actctcttcc accctgactc tgtccaaggc agactatgaa
241 aaacacaagg tatacgcctg cgaggttaca caccagggtt tgtctagtcc tgtcaccaag
301 tccttcaata ggggcgaatg t
```

Nucleic Acid Sequence Encoding the Human Kappa Light Chain Constant Region (Version 2) (SEQ ID NO:71)

```
  1 cgcacagttg cagcccccag cgtgttcatt ttcccaccta gcgatgagca gctgaaaagc
 61 ggtactgcct ctgtcgtatg cttgctcaac aacttttacc cacgtgaggc taaggtgcag
121 tggaaagtgg ataatgcact tcaatctgga aacagtcaag agtccgtgac agaacaggac
181 agcaaagact caacttattc actctcttcc accctgactc tgtccaaggc agactatgaa
241 aaacacaagg tatacgcctg cgaggttaca caccagggtt tgtctagtcc tgtcaccaag
301 tccttcaata ggggcgaatg t
```

Protein Sequence Defining the Human Kappa Light Chain Constant Region (Nucleic Acid Versions 1 and 2 Encode the Same Amino Acid Sequence) (SEQ ID NO:72)

```
 1 rtvaapsvfi fppsdeqlks gtasvvclln nfypreakvq wkvdnalqsg nsqesvteqd
61 skdstyslss tltlskadye khkvyacevt hqglsspvtk sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Ch4F11 Chimeric Heavy Chain (Mouse Heavy Chain Variable Region and Human IgG1 Constant Region) (SEQ ID NO:73)

```
   1 gaggtacagc ttgtcgagtc gggaggagga ttggtaaaac cgggtgggtc actcaaattg
  61 tcgtgtgcgg cgtcgggatt tgcgttttcg tcgtatgata tgtcgtgggt gcgccagacg
 121 ccggaaaaac gattggaatg ggtcgcgtat atctcccgag ggggaggttc gacatactat
 181 cccgacacgg tcaaagggcg cttcacgatt tcacgggaca atgcgaaaaa cacgctttat
 241 cttcaaatgt cgtcgttgaa atcggaagat accgcgatgt attactgcgg gaggcatgcg
 301 acgacggcgt attggtattt cgatgtgtgg ggagccggaa cgacggtgac ggtgtcgtcg
 361 gcctcaacaa aaggaccaag tgtgttccca ctcgcccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagggaa
1081 atgacaaaga accaagtctc attgacctgc ctggtgaaag cttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
```

```
1261 cagcagggta acgtcttcag ctgttccgtg atgcacgagg cattgcacaa ccactacacc 1321 cagaagtcac tgagcctgag cccagggaag
```

Protein Sequence Defining the Full Length Ch4F11 Chimeric Heavy Chain (Mouse Heavy Chain Variable Region and Human IgG1 Constant Region) (SEQ ID NO:74)

```
  1 evqlvesggg lvkpggslkl scaasgfafs sydmswvrqt pekrlewvay isrgggstyy
 61 pdtvkgrfti srdnakntly lqmsslksed tamyycgrha ttaywyfdvw gagttvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh4F11 Hv3-23 Heavy Chain (Humanized Heavy Chain Variable Region and Human IgG1 Constant Region) (SEQ ID NO:75)

```
   1 gaagtacagt tgttggagtc aggaggaggg ttggtccagc cggtggatc gttgcggctt
  61 tcgtgtgcgg cgtcgggatt cgcgttttca tcgtatgaca tgtcgtgggt gaggcaggca
 121 ccggggaaag ggcttgaatg ggtatcgtac atttcgagag ggggaggatc gacgtattac
 181 ccggatacgg tgaaaggaag gtttacgatc tcgcgcgaca attcaaagaa tacgctttat
 241 cttcagatga actcgctccg agcggaagat acggcggtat actattgcgg tcgccatgcg
 301 acgacggcgt attggtattt cgatgtgtgg ggacaaggga cgatggtcac ggtgtcgtcg
 361 gcctcaacaa aaggaccaag tgtgttccca ctcgcccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc tatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh4F11 Hv3-23 Heavy Chain (Humanized Heavy Chain Variable Region and Human IgG1 Constant Region) (SEQ ID NO:76)

```
  1 evqllesggg lvqpggslrl scaasgfafs sydmswvrqa pgkglewvsy isrgggstyy
 61 pdtvkgrfti srdnskntly lqmnslraed tavyycgrha ttaywyfdvw gqgtmvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh4F11 Hv3-23 A28T S31H T62S Heavy Chain (Humanized Heavy Chain Variable Region and Human IgG1 Constant Region) (SEQ ID NO:77)

```
   1 gaagtacagt tgttggagtc aggaggaggg ttggtccagc cggtggatc gttgcggctt
  61 tcgtgtgcgg cgtcgggatt cacctttca cactatgaca tgtcgtgggt gaggcaggca
 121 ccggggaaag ggcttgaatg ggtatcgtac atttcgagag ggggaggatc gacgtattac
 181 ccggattccg tgaaaggaag gtttacgatc tcgcgcgaca attcaaagaa tacgctttat
 241 cttcagatga actcgctccg agcggaagat acggcggtat actattgcgg tcgccatgcg
 301 acgacggcgt attggtattt cgatgtgtgg ggacaaggga cgatggtcac ggtgtcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh4F11 Hv3-23 A28T S31H T62S Heavy Chain (Humanized Heavy Chain Variable Region and Human IgG1 Constant Region) (SEQ ID NO:78)

```
  1 evqllesggg lvqpggslrl scaasgftfs hydmswvrqa pgkglewvsy isrgggstyy
 61 pdsvkgrfti srdnskntly lqmnslraed tavyycgrha ttaywyfdvw gqgtmvtvss
121 astkgpsvfp lapssksstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh4F11 Hv3-23 S31H T62S Heavy Chain (Humanized Heavy Chain Variable Region and Human IgG1 Constant Region) (SEQ ID NO:79)

```
   1 gaagtacagt tgttggagtc aggaggaggg ttggtccagc cggtggatc gttgcggctt
  61 tcgtgtgcgg cgtcgggatt cgcgttttca cactatgaca tgtcgtgggt gaggcaggca
 121 ccggggaaag ggcttgaatg ggtatcgtac atttcgagag ggggaggatc gacgtattac
 181 ccggattccg tgaaaggaag gtttacgatc tcgcgcgaca attcaaagaa tacgctttat
 241 cttcagatga actcgctccg agcggaagat acggcggtat actattgcgg tcgccatgcg
 301 acgacggcgt attggtattt cgatgtgtgg ggacaaggga cgatggtcac ggtgtcgtcg
 361 gcctcaacaa aaggaccaag tgtgttccca ctcgcccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc tatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh4F11 Hv3-23 S31H T62S Heavy Chain (Humanized Heavy Chain Variable Region and Human IgG1 Constant Region) (SEQ ID NO:80)

```
  1 evqllesggg lvqpggslrl scaasgfafs hydmswvrqa pgkglewvsy isrgggstyy
 61 pdsvkgrfti srdnskntly lqmnslraed tavyycgrha ttaywyfdvw gqgtmvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh4F11 Hv3-23 A28T S31N T62S Heavy Chain (Humanized Heavy Chain Variable Region and Human IgG1 Constant Region) (SEQ ID NO:81)

```
   1 gaagtacagt tgttggagtc aggaggaggg ttggtccagc cgggtggatc gttgcggctt
  61 tcgtgtgcgg cgtcgggatt cacctttca aactatgaca tgtcgtgggt gaggcaggca
 121 ccggggaaag ggcttgaatg ggtatcgtac atttcgagag ggggaggatc gacgtattac
 181 ccggattccg tgaaaggaag gtttacgatc tcgcgcgaca attcaaagaa tacgctttat
 241 cttcagatga actcgctccg agcggaagat acggcggtat actattgcgg tcgccatgcg
 301 acgacggcgt attggtattt cgatgtgtgg ggacaaggga cgatggtcac ggtgtcgtcg
 361 gcctcaacaa aaggaccaag tgtgttccca ctcgcccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh4F11 A28T S31N T62S Heavy Chain (Humanized Heavy Chain Variable Region and Human IgG1 Constant Region) (SEQ ID NO:82)

```
  1 evqllesggg lvqpggslrl scaasgftfs nydmswvrqa pgkglewvsy isrgggstyy
 61 pdsvkgrfti srdnskntly lqmnslraed tavyycgrha ttaywyfdvw gqgtmvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh4F11 Hv3-23 A28T T62S Heavy Chain (Humanized Heavy Chain Variable Region and Human IgG1 Constant Region) (SEQ ID NO:83)

```
   1 gaagtacagt tgttggagtc aggaggaggg ttggtccagc cggghtggatc gttgcggctt
  61 tcgtgtgcgg cgtcgggatt cacctttca tcgtatgaca tgtcgtgggt gaggcaggca
 121 ccggggaaag gcttgaatg ggtatcgtac atttcgagag ggggaggatc gacgtattac
 181 ccggattccg tgaaaggaag gtttacgatc tcgcgcgaca attcaaagaa tacgctttat
 241 cttcagatga actcgctccg agcggaagat acggcggtat actattgcgg tcgccatgcg
 301 acgacggcgt attggtattt cgatgtgtgg ggacaaggga cgatggtcac ggtgtcgtcg
 361 gcctcaacaa aaggaccaag tgtgttccca ctcgcccta gcagcaagag tacatccggg
 421 ggcactgcag cactcggctg cctcgtcaag gattattttc cagagccagt aaccgtgagc
 481 tggaacagtg gagcactcac ttctggtgtc catactttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg ccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac cccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh4F11 Hv3-23 A28T T62S Heavy Chain (Humanized Heavy Chain Variable Region and Human IgG1 Constant Region) (SEQ ID NO:84)

```
  1evqllesggg lvqpggslrl scaasgftfs sydmswvrqa pgkglewvsy isrgggstyy
 61pdsvkgrfti srdnskntly lqmnslraed tavyycgrha ttaywyfdvw gqgtmvtvss
121astkgpsvfp lapsskstsg gtaalgclvk dyfpepvtvs wnsgaltsgv htfpavlqss
181glyslssvvt vpssslgtqt yicnvnhkps ntkvdkrvep kscdkthtcp pcpapellgg
241psvflfppkp kdtlmisrtp evtcvvvdvs hedpevkfnw yvdgvevhna ktkpreeqyn
301styrvvsvlt vlhqdwlngk eykckvsnka lpapiektis kakgqprepq vytlppsree
361mtknqvsltc lvkgfypsdi avewesngqp ennykttppv ldsdgsffly skltvdksrw
421qqgnvfscsv mhealhnhyt qkslslspgk
```

Nucleic Acid Sequence Encoding the Full Length Ch4F11 Chimeric Light Chain (Mouse Kappa Chain Variable Region and Human Kappa Constant Region) (SEQ ID NO:85)

```
  1gacgtggtaa tgacgcagac gccgttgtcc cttcctgtct cgctcggaga tcaggcgtcg
 61atctcgtgta gaagctcgca gtcactcgtc cataccaacg gaatacata tcttcactgg
121tatttgcaaa agcccggaca gtcaccgaag ctcttgatct acaaagtatc caatcggttt
181tcgggggtgc ccgaccgatt ctcgggatcg ggttcgggga cggattttac gttgaagatt
241tcgcgggtgg aagcggagga tctcggtgtc tactttttgtt cgcagtcaac gcatgtcccg
301tggacgttcg gaggcgggac aaaacttgag atcaagcgca cagttgctgc cccagcgtg
361ttcatttttcc cacctagcga tgagcagctg aaaagcggta ctgcctctgt cgtatgcttg
421ctcaacaact tttacccacg tgaggctaag gtgcagtgga agtggataa tgcacttcaa
481tctggaaaca gtcaagagtc cgtgacagaa caggacagca aagactcaac ttattcactc
541tcttccaccc tgactctgtc caaggcagac tatgaaaaac acaaggtata cgcctgcgag
601gttacacacc agggtttgtc tagtcctgtc accaagtcct tcaataggg cgaatgt
```

Protein Sequence Defining the Full Length Ch4F11 Chimeric Light Chain (Mouse Kappa Chain Variable Region and Human Kappa Constant Region) (SEQ ID NO:86)

```
  1dvvmtqtpls lpvslgdqas iscrssqslv htngntylhw ylqkpgqspk lliykvsnrf
 61sgvpdrfsgs gsgtdftlki srveaedlgv yfcsqsthvp wtfggtkle ikrtvaapsv
121fifppsdeql ksgtasvvcl lnnfypreak vqwkvdnalq sgnsqesvte qdskdstysl
181sstltlskad yekhkvyace vthqglsspv tksfnrgec
```

Nucleic Acid Sequence Encoding the Full Length Hu4F11 Kv2D-29 Light Chain (Humanized Kappa Chain Variable Region and Human Kappa Constant Region (Version 1)) (SEQ ID NO:87)

```
  1gatgtagtca tgacccaaac gccgctttcg ttgtcggtga cgcccggaca gcccgcgtca
 61atctcgtgtc ggtcatcgca gtcgttggta cacacaaacg gtaatacgta tctccattgg
121tatctccaga agcccggcca gtcgccgcag ctcttgatct acaaagtgag caatcgcttt
181tcgggggtgc cggatcggtt ctcgggatcg gggtcaggaa cggacttcac gcttaagatt
241tcgagggtcg aggcggagga tgtcggagtc tactttttgtt cgcagtccac acatgtcccc
```

```
301 tggacgtttg ggcaggggac gaaggtggaa atcaagcgca cagttgctgc ccccagcgtg 361 ttcattttcc cacctagcga tgagcagctg aaaagcggta ctgcctctgt cgtatgcttg 421 ctcaacaact tttacccacg tgaggctaag gtgcagtgga agtggataa tgcacttcaa 481 tctggaaaca gtcaagagtc cgtgacagaa caggacagca aagactcaac ttattcactc 541 tcttccaccc tgactctgtc caaggcagac tatgaaaaac acaaggtata cgcctgcgag 601 gttacacacc agggtttgtc tagtcctgtc accaagtcct caatagggg cgaatgt
```

Protein Sequence Defining the Full Length Hu4F11 Kv2D-29 Light Chain (Humanized Kappa Chain Variable Region and Human Kappa Constant Region) (SEQ ID NO:88)

```
  1 dvvmtqtpls lsvtpgqpas iscrssqslv htngntylhw ylqkpgqspq lliykvsnrf
 61 sgvpdrfsgs gsgtdftlki srveaedvgv yfcsqsthvp wtfgqgtkve ikrtvaapsv
121 fifppsdeql ksgtasvvcl lnnfypreak vqwkvdnalq sgnsqesvte qdskdstysl
181 sstltlskad yekhkvyace vthqglsspv tksfnrgec
```

Nucleic Acid Sequence Encoding the Full Length Hu4F11 Kv2D-29 N28H Light Chain (Humanized Kappa Chain Variable Region and Human Kappa Constant Region (Version 2)) (SEQ ID NO:89)

```
  1 gatgtagtca tgacccaaac gccgctttcg ttgtcggtga cgcccggaca gcccgcgtca
 61 atctcgtgtc ggtcatcgca gtcgttggta cacacacacg gtaatacgta tctccattgg
121 tatctccaga gcccggcca gtcgccgcag ctcttgatct acaaagtgag caatcgcttt
181 tcgggggtgc cggatcggtt ctcgggatcg gggtcaggaa cggacttcac gcttaagatt
241 tcgagggtcg aggcggagga tgtcggagtc tacttttgtt cgcagtccac acatgtcccc
301 tggacgtttg gcaggggac gaaggtggaa atcaagcgca cagttgcagc ccccagcgtg
361 ttcattttcc cacctagcga tgagcagctg aaaagcggta ctgcctctgt cgtatgcttg
421 ctcaacaact tttacccacg tgaggctaag gtgcagtgga agtggataa tgcacttcaa
481 tctggaaaca gtcaagagtc cgtgacagaa caggacagca aagactcaac ttattcactc
541 tcttccaccc tgactctgtc caaggcagac tatgaaaaac acaaggtata cgcctgcgag
601 gttacacacc agggtttgtc tagtcctgtc accaagtcct caatagggg cgaatgt
```

Protein Sequence Defining the Full Length Hu4F11 Kv2D-29 N28H Light Chain (Humanized Kappa Chain Variable Region and Human Kappa Constant Region) (SEQ ID NO:90)

```
  1 dvvmtqtpls lsvtpgqpas iscrssqslv hthgntylhw ylqkpgqspq lliykvsnrf 61 sgvpdrfsgs gsgtdftlki srveaedvgv yfcsqsthvp wtfgqgtkve ikrtvaapsv 121 fifppsdeql ksgtasvvcl lnnfypreak vqwkvdnalq sgnsqesvte qdskdstysl 181 sstltlskad yekhkvyace vthqglsspv tksfnrgec
```

Nucleic Acid Sequence Encoding the Full Length Hu4F11 Kv2D-29 N28Q Light Chain (Humanized Kappa Chain Variable Region and Human Kappa Constant Region (Version 2)) (SEQ ID NO:91)

```
  1 gatgtagtca tgacccaaac gccgctttcg ttgtcggtga cgcccggaca gcccgcgtca 61 atctcgtgtc ggtcatcgca gtcgttggta cacacacaag gtaatacgta tctccattgg 121 tatctccaga agcccggcca gtcgccgcag ctcttgatct acaaagtgag caatcgcttt 181 tcgggggtgc cggatcggtt ctcgggatcg gggtcaggaa cggacttcac gcttaagatt 241 tcgagggtcg aggcggagga tgtcggagtc tacttttgtt cgcagtccac acatgtcccc 301 tggacgtttg gcaggggac gaaggtggaa atcaagcgca cagttgcagc ccccagcgtg 361 ttcattttcc cacctagcga tgagcagctg aaaagcggta ctgcctctgt cgtatgcttg 421 ctcaacaact tttacccacg tgaggctaag gtgcagtgga aagtggataa tgcacttcaa 481 tctggaaaca gtcaagagtc cgtgacagaa caggacagca aagactcaac ttattcactc 541 tcttccaccc tgactctgtc caaggcagac tatgaaaaac acaaggtata cgcctgcgag 601 gttacacacc agggtttgtc tagtcctgtc accaagtcct tcaatagggg cgaatgt
```

Protein Sequence Defining the Full Length Hu4F11 Kv2D-29 N28Q Light Chain (Humanized Kappa Chain Variable Region and Human Kappa Constant Region) (SEQ ID NO:92)

```
  1 dvvmtqtpls lsvtpgqpas iscrssqslv htqgntylhw ylqkpgqspq lliykvsnrf 61 sgvpdrfsgs gsgtdftlki srveaedvgv yfcsqsthvp wtfgqgtkve ikrtvaapsv 121 fifppsdeql ksgtasvvcl lnnfypreak vqwkvdnalq sgnsqesvte qdskdstysl 181 sstltlskad yekhkvyace vthqglsspv tksfnrgec
```

Nucleic Acid Sequence Encoding the Full Length Hu4F11 Kv2D-29 N28Y Light Chain (Humanized Kappa Chain Variable Region and Human Kappa Constant Region (Version 2)) (SEQ ID NO:93)

```
  1 gatgtagtca tgacccaaac gccgctttcg ttgtcggtga cgcccggaca gcccgcgtca 61 atctcgtgtc ggtcatcgca gtcgttggta cacacatacg gtaatacgta tctccattgg 121 tatctccaga agcccggcca gtcgccgcag ctcttgatct acaaagtgag caatcgcttt 181 tcgggggtgc cggatcggtt ctcgggatcg gggtcaggaa cggacttcac gcttaagatt 241 tcgagggtcg aggcggagga tgtcggagtc tacttttgtt cgcagtccac acatgtcccc 301 tggacgtttg gcaggggac gaaggtggaa atcaagcgca cagttgcagc ccccagcgtg 361 ttcattttcc cacctagcga tgagcagctg aaaagcggta ctgcctctgt cgtatgcttg 421 ctcaacaact tttacccacg tgaggctaag gtgcagtgga aagtggataa tgcacttcaa 481 tctggaaaca gtcaagagtc cgtgacagaa caggacagca aagactcaac ttattcactc 541 tcttccaccc tgactctgtc caaggcagac tatgaaaaac acaaggtata cgcctgcgag 601 gttacacacc agggtttgtc tagtcctgtc accaagtcct tcaatagggg cgaatgt
```

Protein Sequence Defining the Full Length Hu4F11 Kv2D-29 N28Y Light Chain (Humanized Kappa Chain Variable Region and Human Kappa Constant Region) (SEQ ID NO:94)

```
  1 dvvmtqtpls lsvtpgqpas iscrssqslv htygntylhw ylqkpgqspq lliykvsnrf 61 sgvpdrfsgs gsgtdftlki srveaedvgv yfcsqsthvp wtfgqgtkve ikrtvaapsv 121 fifppsdeql ksgtasvvcl lnnfypreak vqwkvdnalq sgnsqesvte qdskdstysl 181 sstltlskad yekhkvyace vthqglsspv tksfnrgec
```

Table 12 is a concordance chart showing the SEQ ID NO. of each sequence discussed in this Example.

TABLE 12

| SEQ ID NO. | Nucleic Acid or Protein |
|---|---|
| 68 | Human IgG1 constant-nucleic acid |
| 69 | Human IgG1 constant-protein |
| 70 | Human Kappa constant-nucleic acid (version 1) |
| 71 | Human Kappa constant-nucleic acid (version 2) |
| 72 | Human Kappa constant-protein (nucleic acid versions 1 and 2 encode the same amino acid sequence) |
| 73 | Chimeric Ch4F11 Heavy Variable + Human IgG1 constant-nucleic acid |
| 74 | Chimeric Ch4F11 Heavy Variable + Human IgG1 constant-protein |
| 75 | Humanized Sh4F11 Hv3-23 Heavy Human Variable + Human IgG1 constant-nucleic acid |
| 76 | Humanized Sh4F11 Hv3-23 Heavy Human Variable + Human IgG1 constant-protein |
| 77 | Humanized Sh4F11 Hv3-23 A28T S31H T62S Heavy Human Variable + Human IgG1 constant-nucleic acid |
| 78 | Humanized Sh4F11 Hv3-23 A28T S31H T62S Heavy Human Variable + Human IgG1 constant-protein |
| 79 | Humanized Sh4F11 Hv3-23 S31H T62S Heavy Human Variable + Human IgG1 constant-nucleic acid |
| 80 | Humanized Sh4F11 Hv3-23 S31H T62S Heavy Human Variable + Human IgG1 constant-protein |
| 81 | Humanized Sh4F11 Hv3-23 A28T S31N T62S Heavy Human Variable + Human IgG1 constant-nucleic acid |
| 82 | Humanized Sh4F11 Hv3-23 A28T S31N T62S Heavy Human Variable + Human IgG1 constant-protein |
| 83 | Humanized Sh4F11 Hv3-23 A28T T62S Heavy Human Variable + Human IgG1 constant-nucleic acid |
| 84 | Humanized Sh4F11 Hv3-23 A28T T62S Heavy Human Variable + Human IgG1 constant-protein |
| 85 | Chimeric Ch4F11 Kappa Variable + Human Kappa constant-nucleic acid (version 1) |
| 86 | Chimeric Ch4F11 Kappa Variable + Human Kappa constant-protein |
| 87 | Humanized Hu4F11 Kv2D-29 Kappa Human Variable + Human Kappa constant-nucleic acid (version 1) |
| 88 | Humanized Hu4F11 Kv2D-29 Kappa Human Variable + Human Kappa constant-protein |
| 89 | Humanized Hu4F11 Kv2D-29 N28H Kappa Human Variable + Human Kappa constant-nucleic acid (version 2) |
| 90 | Humanized Hu4F11 Kv2D-29 N28H Kappa Human Variable + Human Kappa constant-protein |
| 91 | Humanized Hu4F11 Kv2D-29 N28Q Kappa Human Variable + Human Kappa constant-nucleic acid (version 2) |
| 92 | Humanized Hu4F11 Kv2D-29 N28Q Kappa Human Variable + Human Kappa constant-protein |
| 93 | Humanized Hu4F11 Kv2D-29 N28Y Kappa Human Variable + Human Kappa constant-nucleic acid (version 2) |
| 94 | Humanized Hu4F11 Kv2D-29 N28Y Kappa Human Variable + Human Kappa constant-protein |

Table 13 below shows antibodies containing chimeric immunoglobulin heavy and light chains and exemplary combinations of the full-length chimeric or humanized immunoglobulin heavy and light chains.

TABLE 13

| Antibody Name | Heavy Chain | Light Chain |
|---|---|---|
| Hu4F11-1 | Ch4F11 Chimeric Heavy Variable + Human IgG1 constant (SEQ ID NO: 74) | Ch4F11 Chimeric Kappa Variable + Human Kappa constant (SEQ ID NO: 86) |
| Hu4F11-10 | Humanized Sh4F11 Hv3-23 Heavy Human Variable + Human IgG1 constant (SEQ ID NO: 76) | Ch4F11 Chimeric Kappa Variable + Human Kappa constant (SEQ ID NO: 86) |
| Hu4F11-18 | Ch4F11 Chimeric Heavy Variable + Human IgG1 constant (SEQ ID NO: 74) | Humanized Hu4F11 Kv2D-29 Human Variable + Human Kappa constant (SEQ ID NO: 88) |
| Hu4F11-32 | Humanized Sh4F11 Hv3-23 Heavy Human Variable + Human IgG1 constant (SEQ ID NO: 76) | Humanized Hu4F11 Kv2D-29 Human Kappa Variable + Human Kappa constant (SEQ ID NO: 88) |
| Hu4F11-69 | Humanized Sh4F11 Hv3-23 A28T S31N T62S Heavy Human Variable + Human IgG1 constant (SEQ ID NO: 82) | Humanized Hu4F11 Kv2D-29 N28H Human Kappa Variable + Human Kappa constant (SEQ ID NO: 90) |
| Hu4F11-70 | Humanized Sh4F11 Hv3-23 A28T S31H T62S Heavy Human Variable + Human IgG1 constant (SEQ ID NO: 78) | Humanized Hu4F11 Kv2D-29 N28H Human Kappa Variable + Human Kappa constant (SEQ ID NO: 90) |
| Hu4F11-71 | Humanized Sh4F11 Hv3-23 A28T T62S Heavy Human Variable + Human IgG1 constant (SEQ ID NO: 84) | Humanized Hu4F11 Kv2D-29 N28H Human Kappa Variable + Human Kappa constant (SEQ ID NO: 90) |
| Hu4F11-72 | Humanized Sh4F11 Hv3-23 S31H T62S Heavy Human Variable + Human IgG1 constant (SEQ ID NO: 80) | Humanized Hu4F11 Kv2D-29 N28H Human Kappa Variable + Human Kappa constant (SEQ ID NO: 90) |
| Hu4F11-73 | Humanized Sh4F11 Hv3-23 A28T S31N T62S Heavy Human Variable + Human IgG1 constant (SEQ ID NO: 82) | Humanized Hu4F11 Kv2D-29 N28Y Human Kappa Variable + Human Kappa constant (SEQ ID NO: 94) |
| Hu4F11-74 | Humanized Sh4F11 Hv3-23 A28T S31H T62S Heavy Human Variable + Human IgG1 constant (SEQ ID NO: 78) | Humanized Hu4F11 Kv2D-29 N28Y Human Kappa Variable + Human Kappa constant (SEQ ID NO: 94) |
| Hu4F11-75 | Humanized Sh4F11 Hv3-23 A28T T62S Heavy Human Variable + Human IgG1 constant (SEQ ID NO: 84) | Humanized Hu4F11 Kv2D-29 N28Y Human Kappa Variable + Human Kappa constant (SEQ ID NO: 94) |
| Hu4F11-76 | Humanized Sh4F11 Hv3-23 S31H T62S Heavy Human Variable + Human IgG1 constant (SEQ ID NO: 80) | Humanized Hu4F11 Kv2D-29 N28Y Human Kappa Variable + Human Kappa constant (SEQ ID NO: 94) |
| Hu4F11-77 | Humanized Sh4F11 Hv3-23 A28T S31N T62S Heavy Human Variable + Human IgG1 constant (SEQ ID NO: 82) | Humanized Hu4F11 Kv2D-29 N28Q Human Kappa Variable + Human Kappa constant (SEQ ID NO: 92) |

TABLE 13-continued

| Antibody Name | Heavy Chain | Light Chain |
|---|---|---|
| Hu4F11-78 | Humanized Sh4F11 Hv3-23 A28T S31H T62S Heavy Human Variable + Human IgG1 constant (SEQ ID NO: 78) | Humanized Hu4F11 Kv2D-29 N28Q Human Kappa Variable + Human Kappa constant (SEQ ID NO: 92) |
| Hu4F11-79 | Humanized Sh4F11 Hv3-23 A28T T62S Heavy Human Variable + Human IgG1 constant (SEQ ID NO: 84) | Humanized Hu4F11 Kv2D-29 N28Q Human Kappa Variable + Human Kappa constant (SEQ ID NO: 92) |
| Hu4F11-80 | Humanized Sh4F11 Hv3-23 S31H T62S Heavy Human Variable + Human IgG1 constant (SEQ ID NO: 80) | Humanized Hu4F11 Kv2D-29 N28Q Human Kappa Variable + Human Kappa constant (SEQ ID NO: 92) |

The antibody construct containing the full length chimeric heavy and light chains is designated below:

Chimeric 4F11 (Hu4F11-1)=Full Length Ch4F11 Chimeric Heavy Chain (Mouse Heavy Chain Variable Region and Human IgG1 Constant Region) (SEQ ID NO:74) plus Full Length Ch4F11 Chimeric Light Chain (Mouse Kappa Chain Variable Region and Human Kappa Constant Region) (SEQ ID NO:86)

Thirteen of the possible antibody constructs containing the full length immunoglobulin heavy and light chains containing humanized variable regions are designated below:

Hu4F11-32=Full Length Sh4F11 Hv3-23 Heavy Chain (Humanized Heavy Chain Variable Region and Human IgG1 Constant Region) (SEQ ID NO:76) plus Full Length Hu4F11 Kv2D-29 Light Chain (Humanized Kappa Chain Variable Region and Human Kappa Constant Region) (SEQ ID NO:88)

Hu4F11-69=Full Length Sh4F11 Hv3-23 A28T S31N T62S_Heavy Chain (Humanized Heavy Chain Variable Region and Human IgG1 Constant Region) (SEQ ID NO:82) plus Full Length Hu4F11 Kv2D-29 N28H Light Chain (Humanized Kappa Chain Variable Region and Human Kappa Constant Region) (SEQ ID NO:90)

Hu4F11-70=Full Length Sh4F11 Hv3-23 A28T S31H T62S Heavy Chain (Humanized Heavy Chain Variable Region and Human IgG1 Constant Region) (SEQ ID NO:78) plus Full Length Hu4F11 Kv2D-29 N28H Light Chain (Humanized Kappa Chain Variable Region and Human Kappa Constant Region) (SEQ ID NO:90)

Hu4F11-71=Full Length Sh4F11 Hv3-23 A28T T62S Heavy Chain (Humanized Heavy Chain Variable Region and Human IgG1 Constant Region) (SEQ ID NO:84) plus Full Length Hu4F11 Kv2D-29 N28H Light Chain (Humanized Kappa Chain Variable Region and Human Kappa Constant Region) (SEQ ID NO:90)

Hu4F11-72=Full Length Sh4F11 Hv3-23 S31H T62S Heavy Chain (Humanized Heavy Chain Variable Region and Human IgG1 Constant Region) (SEQ ID NO:80) plus Full Length Hu4F11 Kv2D-29 N28H Light Chain (Humanized Kappa Chain Variable Region and Human Kappa Constant Region) (SEQ ID NO:90)

Hu4F11-73=Full Length Sh4F11 Hv3-23 A28T S31N T62S_Heavy Chain (Humanized Heavy Chain Variable Region and Human IgG1 Constant Region) (SEQ ID NO:82) plus Full Length Hu4F11 Kv2D-29 N28Y Light Chain (Humanized Kappa Chain Variable Region and Human Kappa Constant Region) (SEQ ID NO:94)

Hu4F11-74=Full Length Sh4F11 Hv3-23 A28T S31H T62S Heavy Chain (Humanized Heavy Chain Variable Region and Human IgG1 Constant Region) (SEQ ID NO:78) plus Full Length Hu4F11 Kv2D-29 N28Y Light Chain (Humanized Kappa Chain Variable Region and Human Kappa Constant Region) (SEQ ID NO:94)

Hu4F11-75=Full Length Sh4F11 Hv3-23 A28T T62S Heavy Chain (Humanized Heavy Chain Variable Region and Human IgG1 Constant Region) (SEQ ID NO:84) plus Full Length Hu4F11 Kv2D-29 N28Y Light Chain (Humanized Kappa Chain Variable Region and Human Kappa Constant Region) (SEQ ID NO:94)

Hu4F11-76=Full Length Sh4F11 Hv3-23 S31H T62S Heavy Chain (Humanized Heavy Chain Variable Region and Human IgG1 Constant Region) (SEQ ID NO:80) plus Full Length Hu4F11 Kv2D-29 N28Y Light Chain (Humanized Kappa Chain Variable Region and Human Kappa Constant Region) (SEQ ID NO:94)

Hu4F11-77=Full Length Sh4F11 Hv3-23 A28T S31N T62S_Heavy Chain (Humanized Heavy Chain Variable Region and Human IgG1 Constant Region) (SEQ ID NO:82) plus Full Length Hu4F11 Kv2D-29 N28Q Light Chain (Humanized Kappa Chain Variable Region and Human Kappa Constant Region) (SEQ ID NO:92)

Hu4F11-78=Full Length Sh4F11 Hv3-23 A28T S31H T62S Heavy Chain (Humanized Heavy Chain Variable Region and Human IgG1 Constant Region) (SEQ ID NO:78) plus Full Length Hu4F11 Kv2D-29 N28Q Light Chain (Humanized Kappa Chain Variable Region and Human Kappa Constant Region) (SEQ ID NO:92)

Hu4F11-79=Full Length Sh4F11 Hv3-23 A28T T62S Heavy Chain (Humanized Heavy Chain Variable Region and Human IgG1 Constant Region) (SEQ ID NO:84) plus Full Length Hu4F11 Kv2D-29 N28Q Light Chain (Humanized Kappa Chain Variable Region and Human Kappa Constant Region) (SEQ ID NO:92)

Hu4F11-80=Full Length Sh4F11 Hv3-23 S31H T62S Heavy Chain (Humanized Heavy Chain Variable Region and Human IgG1 Constant Region) (SEQ ID NO:80) plus Full Length Hu4F11 Kv2D-29 N28Q Light Chain (Humanized Kappa Chain Variable Region and Human Kappa Constant Region) (SEQ ID NO:92)

Example 9: Binding Affinities of Humanized and Chimeric Anti-Notch3 Monoclonal Antibodies The binding affinities and kinetics of binding of chimeric and humanized antibodies to monomeric recombinant human Notch3 extracellular domain (containing EGF like domains 1-11) fusion protein (monomeric rhNotch3) and monomeric recombinant cynomologus monkey Notch3 extracellular domain (containing EGF like domains 1-12) fusion protein (monomeric rcNotch3) were measured by surface plasmon resonance, using a BIAcore® T100 instrument (GE Healthcare, Piscataway, N.J.).

Goat anti-human IgGs (Fc fragment specific, Jackson ImmunoResearch, West Grove, Pa.) were immobilized on carboxymethylated dextran CM4 sensor chips by amine coupling, according to a standard protocol. Analyses were performed at 25 and 37° C. using PBS containing 0.05% surfactant P20 as running buffer. The antibodies were captured in individual flow cells at a flow rate of 10 µL/minute. Injection time was varied for each antibody to yield an Rmax between 30 and 60 RU. Buffer or Notch3 protein diluted in running buffer was injected sequentially over a reference surface (no antibody captured) and the active surface (antibody to be tested) for 240 seconds at 60 µL/minute. The dissociation phase was monitored for up to 900 seconds. The surface was then regenerated with two 60-second injections of 10 mM Glycine-HCl, pH 2.25, at a flow rate of 30 µL/minute. The Notch3 concentration range tested was 50 nM to 6.25 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined Kinetic values of purified monoclonal antibodies on monomeric rcNotch3 at 25° C. are summarized in Table 14.

TABLE 14

| Antibody | $k_a$ (1/Ms) | $k_d$ (1/s) | $K_D$ (M) | n |
|---|---|---|---|---|
| Hu4F11-1 | 4.8E+05 | 1.0E-02 | 2.4E-08 | 5 |
| Hu4F11-32 | 7.9E+05 | 7.5E-03 | 1.8E-08 | 8 |
| Hu4F11-69 | 1.2E+05 | 9.4E-04 | 7.7E-09 | 1 |
| Hu4F11-70 | 2.0E+05 | 1.0E-03 | 5.2E-09 | 1 |
| Hu4F11-71 | 1.5E+06 | 4.0E-03 | 2.7E-09 | 1 |
| Hu4F11-72 | 2.8E+06 | 4.5E-03 | 1.6E-09 | 1 |
| Hu4F11-73 | 7.6E+05 | 1.9E-03 | 2.6E-09 | 1 |
| Hu4F11-74 | 9.0E+05 | 2.5E-03 | 2.8E-09 | 1 |
| Hu4F11-75 | 7.2E+05 | 2.6E-03 | 3.7E-09 | 1 |
| Hu4F11-76 | 7.8E+05 | 1.9E-03 | 2.5E-09 | 1 |
| Hu4F11-77 | 9.6E+05 | 2.5E-03 | 2.6E-09 | 1 |
| Hu4F11-78 | 1.8E+06 | 3.8E-03 | 2.2E-09 | 1 |
| Hu4F11-79 | 1.3E+06 | 4.6E-03 | 3.4E-09 | 1 |
| Hu4F11-80 | 8.2E+05 | 3.2E-03 | 4.0E-09 | 1 |

Additional kinetic measurements were conducted for each antibody shown in Table 14. These measurements confirmed that the antibodies have affinities ranging from about 1 nM to about 25 nM for monomeric rcNotch3 at 25° C.

Kinetic values of purified monoclonal antibodies on monomeric rcNotch3 at 37° C. are summarized in Table 15.

TABLE 15

| Antibody | $k_a$ (1/Ms) | $k_d$ (1/s) | $K_D$ (M) | n |
|---|---|---|---|---|
| Hu4F11-32 | 5.0E+05 | 1.6E-02 | 3.2E-08 | 5 |
| Hu4F11-69 | 4.0E+05 | 3.8E-03 | 1.1E-08 | 3 |
| Hu4F11-70 | 3.7E+05 | 2.9E-03 | 9.1E-09 | 3 |
| Hu4F11-71 | 4.1E+05 | 5.6E-03 | 1.4E-08 | 3 |
| Hu4F11-72 | 4.4E+05 | 3.2E-03 | 9.8E-09 | 3 |
| Hu4F11-73 | 5.0E+05 | 6.3E-03 | 1.5E-08 | 3 |
| Hu4F11-74 | 4.4E+05 | 4.5E-03 | 1.2E-08 | 3 |
| Hu4F11-75 | 3.8E+05 | 8.9E-03 | 2.4E-08 | 3 |
| Hu4F11-76 | 5.4E+05 | 6.2E-03 | 1.2E-08 | 3 |
| Hu4F11-77 | 9.1E+05 | 1.0E-02 | 1.2E-08 | 3 |
| Hu4F11-78 | 6.6E+05 | 7.0E-03 | 1.1E-08 | 3 |
| Hu4F11-79 | 9.8E+05 | 2.1E-02 | 2.3E-08 | 3 |
| Hu4F11-80 | 9.1E+05 | 1.0E-02 | 1.2E-08 | 3 |

Additional kinetic measurements were conducted for each antibody shown in Table 15. These measurements confirmed that the antibodies have affinities ranging from about 9 nM to about 35 nM for monomeric rcNotch3 at 37° C.

Kinetic values of purified monoclonal antibodies on monomeric rhNotch3 at 37° C. are summarized in Table 16.

TABLE 16

| Antibody | $k_a$ (1/Ms) | $k_d$ (1/s) | $K_D$ (M) | n |
|---|---|---|---|---|
| Hu4F11-32 | 1.7E+06 | 4.6E-03 | 2.7E-09 | 1 |
| Hu4F11-69 | 1.3E+06 | 3.8E-03 | 2.9E-09 | 1 |
| Hu4F11-70 | 9.4E+05 | 2.8E-03 | 3.0E-09 | 1 |
| Hu4F11-71 | 1.2E+06 | 3.7E-03 | 3.0E-09 | 1 |

TABLE 16-continued

| Antibody | $k_a$ (1/Ms) | $k_d$ (1/s) | $K_D$ (M) | n |
|---|---|---|---|---|
| Hu4F11-72 | 1.8E+05 | 9.4E-04 | 5.2E-09 | 1 |
| Hu4F11-73 | 2.1E+05 | 1.3E-03 | 5.9E-09 | 1 |
| Hu4F11-74 | 5.6E+05 | 2.2E-03 | 3.9E-09 | 1 |
| Hu4F11-75 | 2.7E+06 | 9.0E-03 | 3.4E-09 | 1 |
| Hu4F11-76 | 1.7E+06 | 5.5E-03 | 3.3E-09 | 1 |
| Hu4F11-77 | 2.2E+06 | 7.3E-03 | 3.3E-09 | 1 |
| Hu4F11-78 | 1.5E+06 | 5.5E-03 | 3.8E-09 | 1 |
| Hu4F11-79 | 1.8E+06 | 6.0E-03 | 3.2E-09 | 1 |
| Hu4F11-80 | 1.1E+06 | 4.1E-03 | 3.8E-09 | 1 |

Additional kinetic measurements were conducted for each antibody shown in Table 16. The additional measurements were averaged together with those presented in Table 16. These combined measurements indicated that the antibodies have affinities ranging from about 7 nM to about 16 nM for monomeric rhNotch3 at 37° C. (Table 17).

TABLE 17

| Antibody | $k_a$ (1/Ms) | $k_d$ (1/s) | $K_D$ (M) | n |
|---|---|---|---|---|
| Hu4F11-32 | 7.4E+06 | 8.4E-02 | 7.6E-09 | 2 |
| Hu4F11-69 | 7.1E+05 | 3.7E-03 | 8.5E-09 | 3 |
| Hu4F11-70 | 6.9E+05 | 3.9E-03 | 7.5E-09 | 4 |
| Hu4F11-71 | 1.1E+06 | 9.5E-03 | 9.2E-09 | 3 |
| Hu4F11-72 | 7.1E+05 | 6.9E-03 | 7.0E-09 | 4 |
| Hu4F11-73 | 4.9E+05 | 4.6E-03 | 1.1E-08 | 3 |
| Hu4F11-74 | 4.9E+05 | 5.1E-03 | 1.0E-08 | 4 |
| Hu4F11-75 | 1.7E+06 | 1.3E-02 | 1.0E-08 | 3 |
| Hu4F11-76 | 9.8E+05 | 6.4E-03 | 8.2E-09 | 3 |
| Hu4F11-77 | 1.2E+06 | 7.4E-03 | 8.6E-09 | 3 |
| Hu4F11-78 | 8.2E+05 | 6.0E-03 | 9.0E-09 | 4 |
| Hu4F11-79 | 9.0E+05 | 9.1E-03 | 1.6E-08 | 3 |
| Hu4F11-80 | 5.9E+05 | 5.6E-03 | 1.4E-08 | 3 |

The results in Tables 14-17 demonstrate that the chimeric and each of the humanized antibodies, have fast association rates ($k_a$), very slow disassociation rates ($k_d$) and very high affinities ($K_D$). In particular, the antibodies have affinities ranging from about 1 nM to about 35 nM.

Example 10: Binding of Humanized 4F11 Antibodies to Cell Surface-Expressed Notch3

Binding of humanized 4F11 variants to cell surface Notch3 receptor was confirmed by FACS. FlpIn™ CHO lines stably expressing human Notch3, or FlpIn™ CHO lines expressing no human Notch receptors, were used for binding experiments. CHO cells were harvested using Cell Dissociation Buffer (Life Technologies, Grand Island, N.Y.) and resuspended at 2.5×10⁶ cells/ml in PBS/0.5% BSA. 100 µl of cell suspension per sample was added to a 96 well v-bottom plate. 4F11 humanized antibodies or human IgG were added at 5 ng/ml to the wells, mixed, and incubated on ice for one hour. After washing with PBS/0.5% BSA, anti-human PE conjugated secondary antibody was added at a 1:100 dilution in PBS/0.5% BSA and allowed to incubate on ice in the dark for 30 minutes. Cells were washed with PBS/0.5% BSA, then resuspended in 300 µl PBS/0.5% BSA and FACS analysis was performed. Expression of human Notch3 receptor was confirmed using anti-human Notch3 PE (BioLegend, San Diego, Calif.) as a positive control. FACS analysis confirmed that the humanized 4F11 antibody variants bind to human Notch3 expressed on the cell surface.

Example 11: Inhibition of Ligand-Induced Notch3 ICD Cleavage by Humanized 4F11 Antibodies Selected humanized 4F11 variants were tested for their ability to inhibit ligand-induced activation of Notch3, as measured by the presence of cleaved ICD. The MDA-MB-468 breast cancer cell line, which expresses endogenous human Notch3, was plated in 96-well plates previously coated with hJag2-mFc fusion protein. The wells were prepared by diluting α-mouse Fc (Jackson ImmunoResearch, West Grove, Pa.) to 5 µg/ml in sterile-filtered carbonate-bicarbonate coating buffer, pH 9.4 (Thermo Fisher Scientific, Rockland, Md.). Then 100 µl of the diluted antibody was added to each well of a 96-well Maxisorp™ plate and incubated overnight at 4° C. The next day, wells were washed three times with PBS/0.5% BSA before adding 100 µl of soluble Jag2-mFc fusion protein or mouse IgG Fc (Jackson Immunolabs) diluted to 5 µg/ml in PBS/0.5% BSA. After incubating for two hours at room temperature on an orbital shaker, the wells were washed three times with PBS/0.5% BSA to remove unbound ligand. MDA-MB-468 cells were counted and resuspended in fresh growth media at $0.4 \times 10^6$ cells/ml. Cells were pre-incubated with 10 µg/ml of the 4F11 humanized antibodies for 30 minutes at 37° C., before seeding 100 µl of the suspension into 96-well plates coated with hJag2-mFc ligand or mFc. Cells were incubated overnight at 37° C. The next day wells were gently washed with ice cold PBS, then cells harvested by adding RIPA buffer containing protease inhibitors directly to the well. Lysates were clarified by centrifugation in a refrigerated microcentrifuge. Supernatants were boiled with 5×SDS sample buffer before loading onto an SDS PAGE gel and Western blotting. Blots were probed with a α-Notch3 antibody to detect the cleaved intracellular domain (Cell Signaling, Danvers, Mass.). The same blots were also probed with anti-β tubulin (Cell Signaling) for use as a loading control. Bands were quantitated using ImageLab software (BioRad, Hercules, Calif.) and values adjusted relative to their respective loading control. Each sample was then normalized relative to the value of the Notch3 ICD band from cells plated on wells without ligand in the presence of hIgG control antibody.

Figure 11:
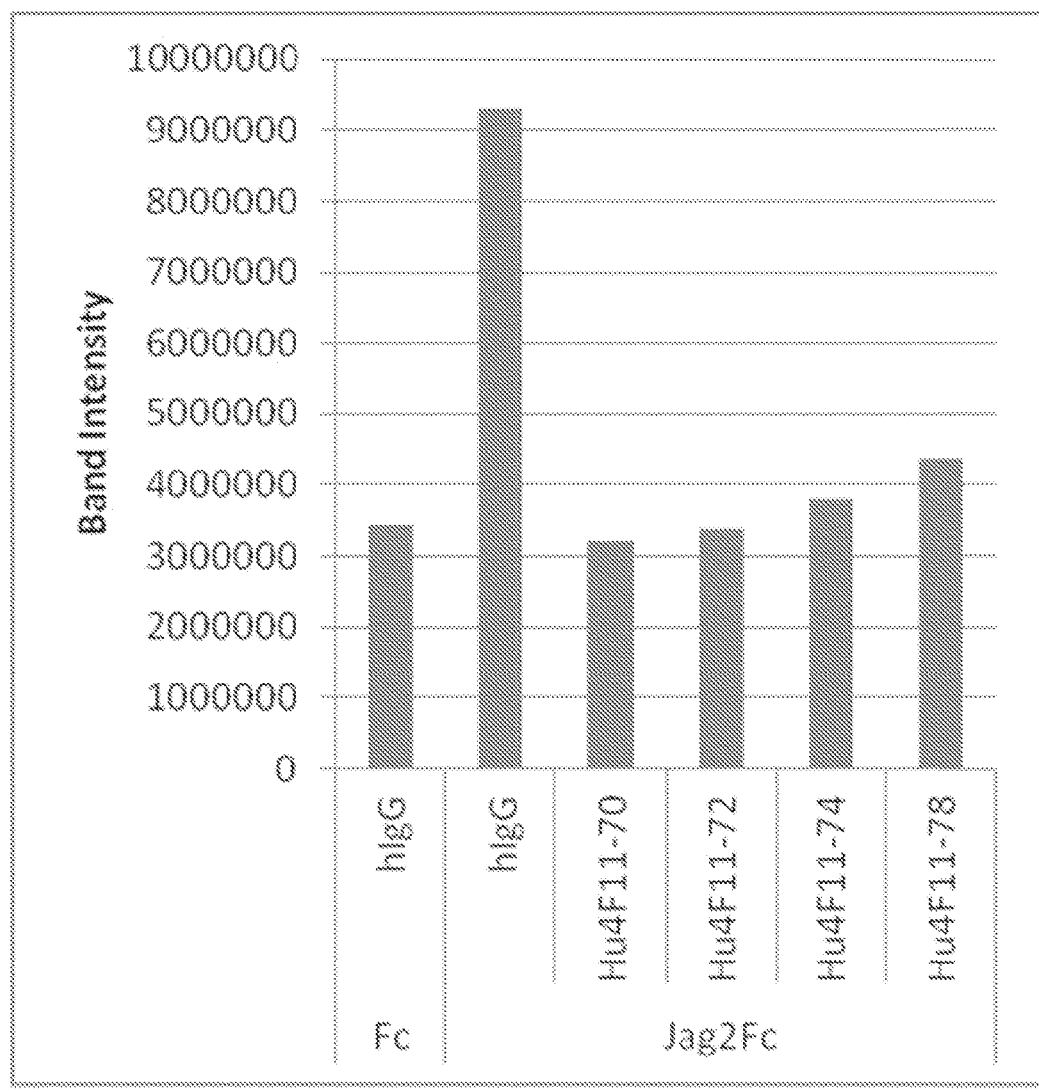
FIG. 11 is a graph illustrating the ability of selected humanized 4F11 (i.e., Hu4F11-70, Hu4F11-72, Hu4F11-74, and Hu4F11-78) antibodies to inhibit ligand-induced Notch3 ICD cleavage in MDA-MB-468 cells plated on Jag2mFc. MDA-MB-468 cells exposed to either one of the 4F11 antibodies or hIgG were plated in wells coated with hJag2-mFc, incubated overnight, washed, and their lysates collected for detection of NICD by Western blot. The graph shows intensity of the cleaved NICD band in each sample as detected by Western blot. Blots were also probed with anti-β tubulin as a control, and bands were quantitated using ImageLab software. As a negative control, cells exposed to hIgG were plated in plates coated with mFc (Fc) rather than Jag2mFc.

The humanized 4F11 antibody variants significantly inhibit ligand-induced cleavage of the Notch3 ICD as summarized in FIG. 11.

Example 12: Inhibition of Notch3-Dependent Transcription by Humanized 4F11 Antibodies Luciferase reporter assays were used to assess the ability of certain humanized 4F11 antibodies to inhibit ligand-dependent Notch3 receptor signaling and transcriptional activity. HCC1143 reporter lines co-cultured with CHO cells expressing Notch ligands were utilized for these assays.

Stable lines expressing full length Notch ligands at the cell surface were produced by transfecting FlpIn™ CHO cells with Jag1, Jag2, DLL1, or DLL4 cDNAs cloned into the pcDNA5FRT vector using Lipofectamine 2000 (Life Technologies) according to the manufacturer's protocol. Twenty-four hours after transfection, CHO cells were split into F12 media containing 10% FBS, 2 mM L-Glutamine and 700 µg/ml hygromycin B (Sigma-Aldrich, St. Louis, Mo.) to select for transfected cells. Expression of Notch ligands was confirmed by FACS analysis using antibodies against Jag1 (R&D Systems, Inc., Minneapolis, Minn.), Jag2 (R&D Systems), DLL1 (R&D Systems), and DLL4 (BioLegend, San Diego, Calif.).

FlpIn™ CHO lines stably expressing Notch ligands were trypsinized, counted and seeded in 96-well plates at 60K cells/well in 100 µl of Ham's F12 K media without hygromycin B. The next day, HCC1143 reporter cells were spun down and resuspended in RPMI media containing 2% FBS at $0.2 \times 10^6$ cells/ml. Antibodies were serially diluted into RPMI without FBS, and 100 µl of antibody solution was added to an equal volume of reporter cells for 30 minutes at 37° C. in a 5% CO2 incubator. After removing media from the hJag2 CHO cells, 100 µl of the HCC1143 reporter/antibody mix was added to the ligand-expressing cells and allowed to incubate at 37° C. overnight. Twenty-four hours later, 96-well plates placed at room temperature for 20 minutes, then processed with the Bright Glo (Promega, Madison, Wis.) reporter assay protocol per the manufacturer's instructions. Lysates were transferred to white-walled 96 well plates (Greiner Bio-One, Frickenhausen, Germany) and read on a GloMax Luminometer (Promega) using the Bright Glo program.

Figure 12A:
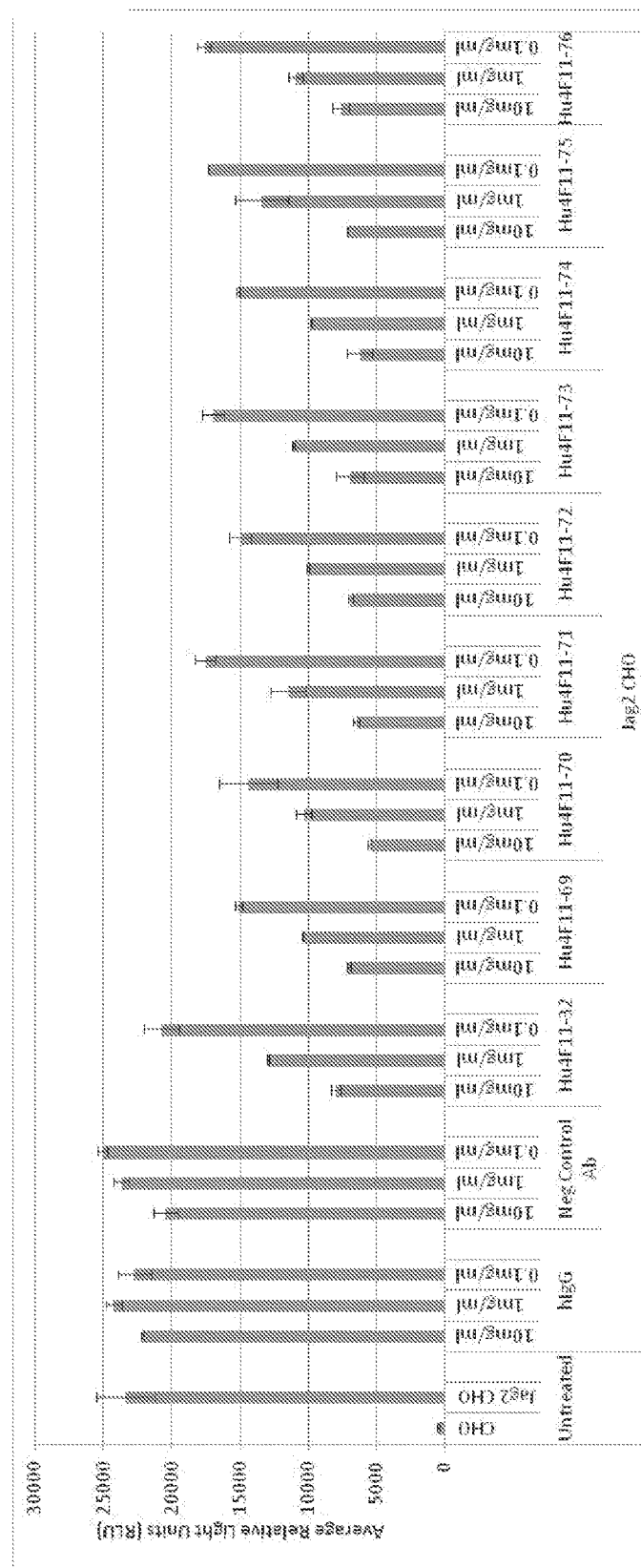
FIG. 12A and FIG. 12B are graphs summarizing results of a Notch3 reporter assay showing that the humanized variants of 4F11 inhibit Notch3-dependent reporter gene expression induced by the ligand Jag2. CHO cells transfected with Jag2 cDNA expression vector were incubated for 24 hours with a mixture of HCC1143 reporter cells and 0.1 mg/ml, 1 mg/ml, or 10 mg/ml of 4F11 antibody variants (i.e., Hu4F11-32, Hu4F11-69, Hu4F11-70, Hu4F11-71, Hu4F11-72, Hu4F11-73, Hu4F11-74, Hu4F11-75, Hu4F11-76, Hu4F11-77, Hu4F11-78, Hu4F11-79, or Hu4F11-80), a negative control antibody (Neg Control Ab), or human immunoglobulin G (IgG), or were left untreated. 24 hours after exposing reporter cells to Jag2-expressing CHO cells, cells were processed using the Bright Glo (Promega, Madison, Wis.) reporter assay protocol and average relative light units (RLU) were detected on a GloMax Luminometer (Promega) (FIG. 12A and FIG. 12B).
Figure 12B:
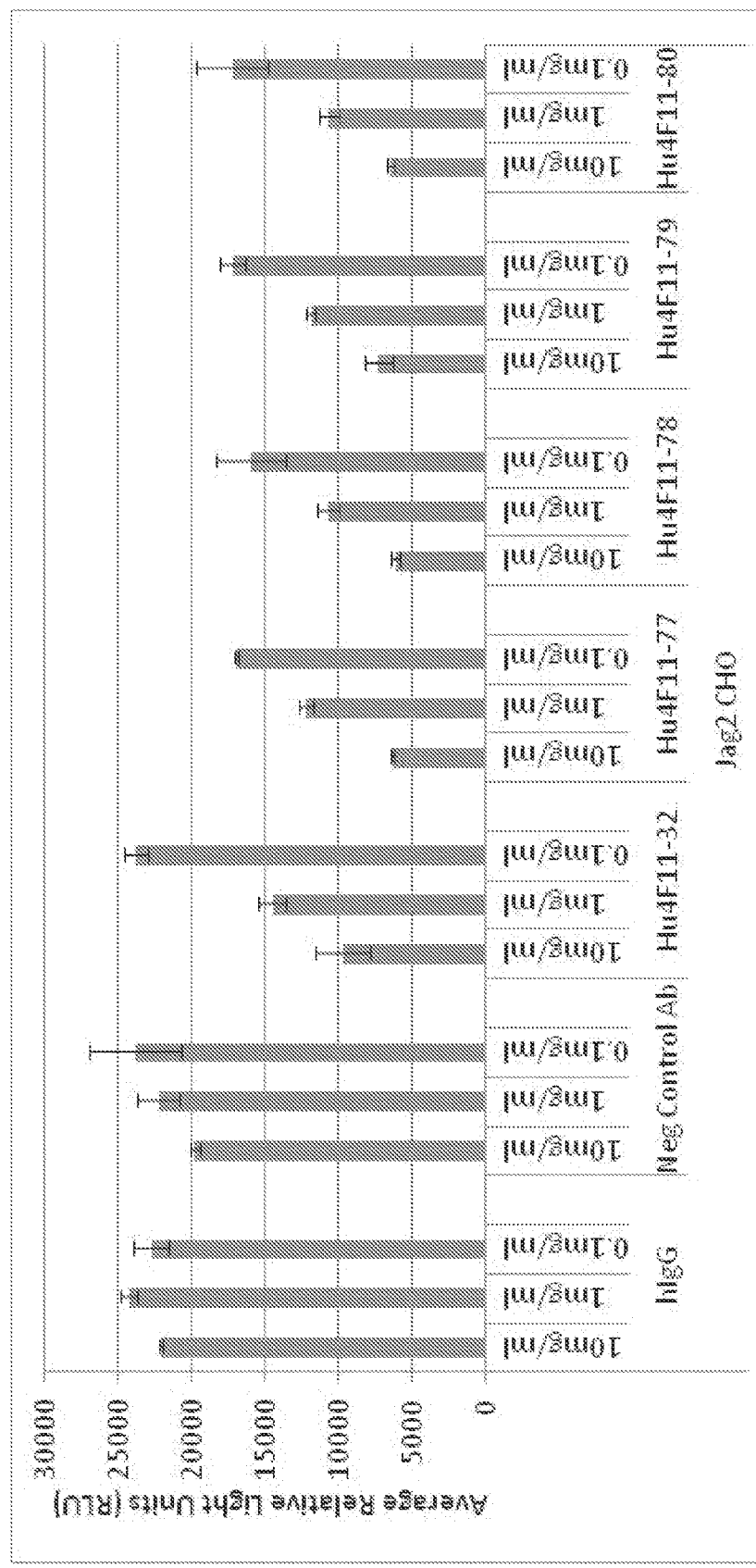

As shown in FIG. 12A-B, the humanized 4F11 antibody variants inhibit activation of ligand-induced transcription in the HCC1143 reporter cell line.

Example 13: Inhibition of Notch3 ICD Cleavage In Vivo

Selected humanized 4F11 antibodies (i.e., Hu4F11-70, Hu4F11-72, Hu4F11-78) were tested for their ability to inhibit cleavage of Notch3 ICD expressed in HCC2429 tumors in vivo.

All mice were treated in accordance with the OLAW Public Health Service Policy on Human Care and Use of Laboratory Animals and the ILAR Guide for the Care and Use of Laboratory Animals. All in vivo studies were conducted following the protocols approved by the AVEO Institutional Animal Care and Use Committee. HCC2429 is a lung cancer cell line harboring a translocation of chromosome 19 that results in overexpression of the Notch3 receptor. For the Notch3 ICD cleavage experiments, approximately thirteen week old NCR nude mice (Taconic, Germantown, N.Y.) were inoculated subcutaneously into the right flank with $5 \times 10^6$ cells in 1:1 DMEM+Matrigel (Invitrogen, Carlsbad, Calif.)/Matrigel (BD Biosciences, San Jose, Calif.). Tumor measurements were taken twice weekly, using vernier calipers. Tumor volume was calculated using the formula: $V = 0.5 \times width \times width \times length$. When tumors approached a volume of 300-400 mm$^3$, mice were randomized into groups of three animals each (corresponds to mouse 1 (m1) through mouse 3 (m3), as designated in FIG. 13). The next day, mice were treated with 20 mg/kg hIgG (control), or 20 mg/kg of antibodies Hu4F11-70, Hu4F11-72, Hu4F11-78 or murine 4F11 (mu4F11) by intraperitoneal injection. Mice were dosed once, and tumors were collected 24 hours later and snap frozen.

Figure 13:
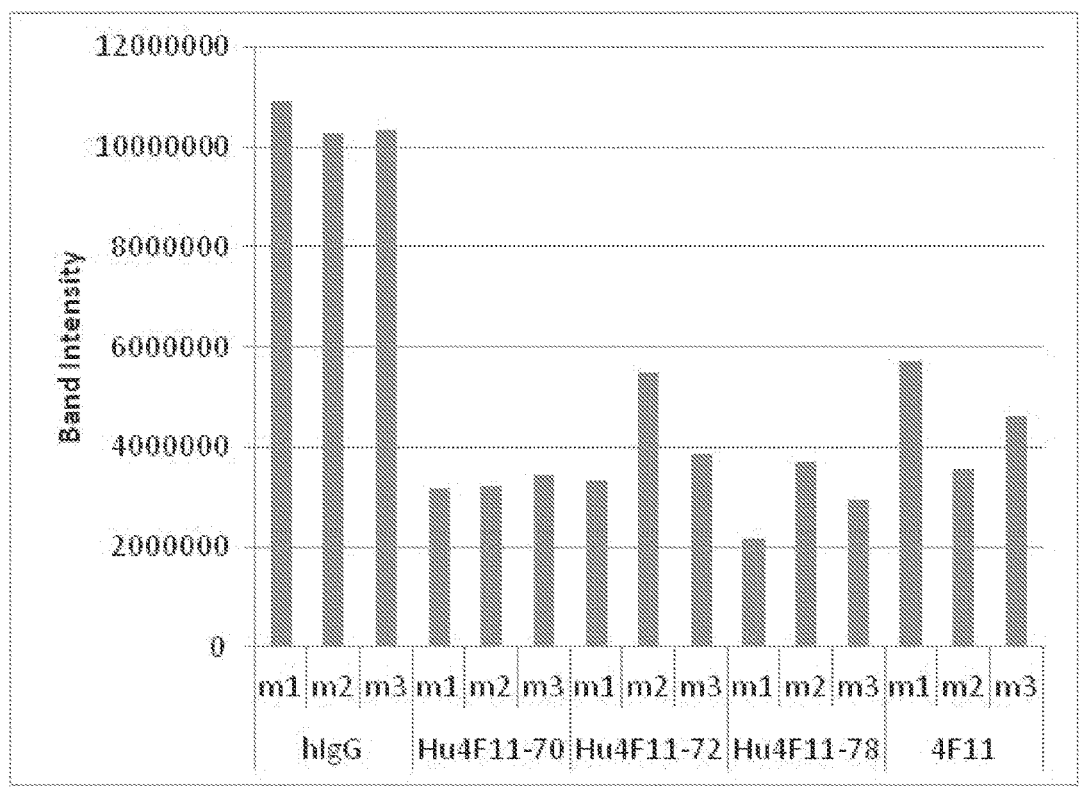
FIG. 13 is a graph illustrating the ability of selected humanized 4F11 antibodies (i.e., Hu4F11-70, Hu4F11-72 and Hu4F11-78) to inhibit activation of Notch3 receptor in vivo after treatment of mice bearing HCC2429 xenograft tumors. Mice inoculated with matrigel and HCC2429 Notch3-expressing cells were allowed to develop tumors of 300-400 $mm^3$, at which point three mice (m1, m2, and m3 in FIG. 13) each were treated with 20 mg/kg of hIgG, 4F11, or humanized Notch3 antibody. Tumors were then harvested and lysates collected, and Western blotting was performed using an antibody specific for the Notch3 C-terminus in order to detect the extent of Notch intracellular domain cleavage. Western blot band intensity of the cleaved Notch intracellular domain fragment was calculated, normalizing to β-tubulin loading control.

To assess levels of cleaved Notch3 ICD, tumors were pulverized using a Covaris cryoPREP™ impactor (Covaris, Woburn, Mass.), resuspended in RIPA buffer (Boston BioProducts) containing protease inhibitors, and rotated at 4° C. for 1 hour. Lysates were clarified by spinning at 14 k rpm for 15 minutes in a refrigerated microcentrifuge. Protein concentration for each sample was measured using the BioRad DC protein assay (BioRad). Equal concentrations of protein from each sample were loaded onto an SDS PAGE gel and transferred onto nitrocellulose by Western blotting. Blots were probed with antibody against the C-terminus of Notch3 (Cell Signaling) to detect levels of the cleaved ICD. Blots were also probed with antibody against β-tubulin (Cell Signaling) for use as a loading control. Bands were quantified using Image Lab 3.0 software (BioRad), and the intensity of Notch3 ICD bands were normalized to their respective β-tubulin loading control. All humanized 4F11 antibodies tested (i.e., Hu4F11-70, Hu4F11-72, Hu4F11-78)

significantly inhibit Notch3 activation in vivo, as measured by Notch3 ICD levels present in tumors 24 hours after single dose antibody treatment (FIG. 13).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human Notch3 comprising an immunoglobulin heavy chain variable region and an immunoglobulin light chain variable region selected from the group consisting of:
   (a) (i) an immunoglobulin heavy chain variable region comprising a $CDR_{H1}$ comprising the amino acid sequence of SEQ ID NO:51, a $CDR_{H2}$ comprising the amino acid sequence of SEQ ID NO:53, and a $CDR_{H3}$ comprising the amino acid sequence of SEQ ID NO:7; and
      (ii) an immunoglobulin light chain variable region comprising a $CDR_{L1}$ comprising the amino acid sequence of SEQ ID NO:62, a $CDR_{L2}$ comprising the amino acid sequence of SEQ ID NO:9, and a $CDR_{L3}$ comprising the amino acid sequence of SEQ ID NO:10;
   (b) (i) an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a $CDR_{H3}$ comprising the amino acid sequence of SEQ ID NO: 7; and
      (ii) an immunoglobulin light chain variable region comprising a $CDR_{L1}$ comprising the amino acid sequence of SEQ ID NO: 8; a $CDR_{L2}$ comprising the amino acid sequence of SEQ ID NO: 9; and a $CDR_{L3}$ comprising the amino acid sequence of SEQ ID NO: 10;
   (c) (i) an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a $CDR_{H3}$ comprising the amino acid sequence of SEQ ID NO: 7; and
      (ii) an immunoglobulin light chain variable region comprising a $CDR_{L1}$ comprising the amino acid sequence of SEQ ID NO: 62; a $CDR_{L2}$ comprising the amino acid sequence of SEQ ID NO: 9; and a $CDR_{L3}$ comprising the amino acid sequence of SEQ ID NO: 10;
   (d) (i) an immunoglobulin heavy chain variable region comprising a $CDR_{H1}$ comprising an amino acid sequence selected from the group consisting of SEQ ID NO: 5 and SEQ ID NO:11; a $CDR_{H2}$ comprising the amino acid sequence of SEQ ID NO: 6; and a CDR$_{H3}$ comprising the amino acid sequence of SEQ ID NO: 7; and (ii) an immunoglobulin light chain variable region comprising a CDR$_{L1}$ comprising the amino acid sequence of SEQ ID NO: 63; a CDR$_{L2}$ comprising the amino acid sequence of SEQ ID NO: 9; and a CDR$_{L3}$ comprising the amino acid sequence of SEQ ID NO: 10;

(e) (i) an immunoglobulin heavy chain variable region comprising a CDR$_{H1}$ comprising an amino acid sequence selected from the group consisting of SEQ ID NO: 5 and SEQ ID NO:11; a CDR$_{H2}$ comprising the amino acid sequence of SEQ ID NO: 6; and a CDR$_{H3}$ comprising the amino acid sequence of SEQ ID NO: 7; and (ii) an immunoglobulin light chain variable region comprising a CDR$_{L1}$ comprising the amino acid sequence of SEQ ID NO: 64; a CDR$_{L2}$ comprising the amino acid sequence of SEQ ID NO: 9; and a CDR$_{L3}$ comprising the amino acid sequence of SEQ ID NO: 10;

(f) (i) an immunoglobulin heavy chain variable region comprising a CDR$_{H1}$ comprising the amino acid sequence of SEQ ID NO:51, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:8, a CDR$_{L2}$ comprising the amino acid sequence of SEQ ID NO:9, and a CDR$_{L3}$ comprising the amino acid sequence of SEQ ID NO:10;

(g) (i) an immunoglobulin heavy chain variable region comprising a CDR$_{H1}$ comprising the amino acid sequence of SEQ ID NO:51, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:63, a CDR$_{L2}$ comprising the amino acid sequence of SEQ ID NO:9, and a CDR$_{L3}$ comprising the amino acid sequence of SEQ ID NO:10;

(h) (i) an immunoglobulin heavy chain variable region comprising a CDR$_{H1}$ comprising the amino acid sequence of SEQ ID NO:51, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:64, a CDR$_{L2}$ comprising the amino acid sequence of SEQ ID NO:9, and a CDR$_{L3}$ comprising the amino acid sequence of SEQ ID NO:10;

(i) (i) an immunoglobulin heavy chain variable region comprising a CDR$_{H1}$ comprising an amino acid sequence selected from the group consisting of SEQ ID NO:52 and SEQ ID NO: 56, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:8, a CDR$_{L2}$ comprising the amino acid sequence of SEQ ID NO:9, and a CDR$_{L3}$ comprising the amino acid sequence of SEQ ID NO:10;

(j) (i) an immunoglobulin heavy chain variable region comprising a CDR$_{H1}$ comprising an amino acid sequence selected from the group consisting of SEQ ID NO:52 and SEQ ID NO: 56, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:62, a CDR$_{L2}$ comprising the amino acid sequence of SEQ ID NO:9, and a CDR$_{L3}$ comprising the amino acid sequence of SEQ ID NO:10;

(k) (i) an immunoglobulin heavy chain variable region comprising a CDR$_{H1}$ comprising an amino acid sequence selected from the group consisting of SEQ ID NO:52 and SEQ ID NO: 56, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:63, a CDR$_{L2}$ comprising the amino acid sequence of SEQ ID NO:9, and a CDR$_{L3}$ comprising the amino acid sequence of SEQ ID NO:10;

(l) (i) an immunoglobulin heavy chain variable region comprising a CDR$_{H1}$ comprising an amino acid sequence selected from the group consisting of SEQ ID NO:52 and SEQ ID NO: 56, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:64, a CDR$_{L2}$ comprising the amino acid sequence of SEQ ID NO:9, and a CDR$_{L3}$ comprising the amino acid sequence of SEQ ID NO:10;

(m) (i) an immunoglobulin heavy chain variable region comprising a CDR$_{H1}$ comprising an amino acid sequence selected from the group consisting of SEQ ID NO:5 and SEQ ID NO: 57, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:8, a CDR$_{L2}$ comprising the amino acid sequence of SEQ ID NO:9, and a CDR$_{L3}$ comprising the amino acid sequence of SEQ ID NO:10;

(n) (i) an immunoglobulin heavy chain variable region comprising a CDR$_{H1}$ comprising an amino acid sequence selected from the group consisting of SEQ ID NO:5 and SEQ ID NO: 57, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:62, a CDR$_{L2}$ comprising the amino acid sequence of SEQ ID NO:9, and a CDR$_{L3}$ comprising the amino acid sequence of SEQ ID NO:10;

(o) (i) an immunoglobulin heavy chain variable region comprising a CDR$_{H1}$ comprising an amino acid sequence selected from the group consisting of SEQ ID NO:5 and SEQ ID NO: 57, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:63, a CDR$_{L2}$ comprising the amino acid sequence of SEQ ID NO:9, and a CDR$_{L3}$ comprising the amino acid sequence of SEQ ID NO:10; and (p) (i) an immunoglobulin heavy chain variable region comprising a CDR$_{H1}$ comprising an amino acid sequence selected from the group consisting of SEQ ID NO:5 and SEQ ID NO: 57, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:64, a CDR$_{L2}$ comprising the amino acid sequence of SEQ ID NO:9, and a CDR$_{L3}$ comprising the amino acid sequence of SEQ ID NO:10.

2. The antibody of claim 1, wherein the CDR sequences are interposed between human or humanized framework sequences.

3. An isolated nucleic acid comprising a nucleotide sequence encoding an immunoglobulin heavy chain variable region of claim 1.

4. An expression vector comprising the nucleic acid of claim 3.

5. A host cell comprising the expression vector of claim 4.

6. An isolated nucleic acid comprising a nucleotide sequence encoding an immunoglobulin light chain variable region of claim 1.

7. An expression vector comprising the nucleic acid of claim 6.

8. The expression vector of claim 6, further comprising the nucleic acid of claim 3.

9. A host cell comprising the expression vector of claim 8.

10. A method of producing an antibody that binds human Notch3 or an antigen binding fragment of the antibody, the method comprising:

(a) growing the host cell of claim 9 under conditions so that the host cell expresses a polypeptide or polypeptides comprising the immunoglobulin heavy chain variable region and the immunoglobulin light chain variable region, thereby producing the antibody or the antigen-binding fragment of the antibody; and (b) purifying the antibody or the antigen-binding fragment of the antibody.

11. A host cell comprising the expression vector of claim 7.

12. A host cell of claim 11, further comprising the expression vector of claim 4.

13. A method of producing an antibody that binds human Notch3 or an antigen binding fragment of the antibody, the method comprising:

(a) growing the host cell of claim 12 under conditions so that the host cell expresses a polypeptide or polypeptides comprising the immunoglobulin heavy chain variable region and the immunoglobulin light chain variable region, thereby producing the antibody or the antigen-binding fragment of the antibody; and (b) purifying the antibody or the antigen-binding fragment of the antibody.

14. A method of producing a polypeptide comprising an immunoglobulin heavy chain variable region or an immunoglobulin light chain variable region, the method comprising:

(a) growing the host cell of claim 5 or 11 under conditions so that the host cell expresses the polypeptide comprising the immunoglobulin heavy chain variable region or the immunoglobulin light chain variable region; and (b) purifying the polypeptide comprising the immunoglobulin heavy chain variable region or the immunoglobulin light chain variable region.

15. A method of inhibiting or reducing proliferation of a tumor cell comprising exposing the cell to an effective amount of the antibody of claim 1 to inhibit or reduce proliferation of the tumor cell.

16. A method of inhibiting or reducing tumor growth in a mammal, the method comprising exposing the mammal to an effective amount of the antibody of claim 1 to inhibit or reduce proliferation of the tumor.

17. A method of treating cancer in a human subject, the method comprising administering to the subject an effective amount of the antibody of claim 1 to a human subject in need thereof.

18. The antibody of claim 1, wherein the antibody has a K$_D$ of 35 nM or lower as measured by surface plasmon resonance.

19. The isolated antibody of claim 1, wherein the antibody comprises:

(i) an immunoglobulin heavy chain variable region comprising a CDR$_{H1}$ comprising the amino acid sequence of SEQ ID NO:51, a CDR$_{H2}$ comprising the amino acid sequence of SEQ ID NO:53, and a CDR$_{H3}$ comprising the amino acid sequence of SEQ ID NO:7; and (ii) an immunoglobulin light chain variable region comprising a CDR$_{L1}$ comprising the amino acid sequence of SEQ ID NO:62, a CDR$_{L2}$ comprising the amino acid sequence of SEQ ID NO:9, and a CDR$_{L3}$ comprising the amino acid sequence of SEQ ID NO:10.

20. An isolated antibody that binds human Notch3 comprising an immunoglobulin heavy chain variable region and an immunoglobulin light chain variable region selected from the group consisting of:

(a) an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:46 (Hu4F11 Kv2D-29 N28H);

(b) an immunoglobulin heavy chain variable region comprising the amino acid sequence of SEQ ID NO:2 (4F11, Ch4F11 Chimeric), and an immunoglobulin light chain variable region comprising the amino acid sequence of SEQ ID NO:4 (4F11, Ch4F11 Chimeric);

(c) an immunoglobulin heavy chain variable region comprising the amino acid sequence of SEQ ID NO:2 (4F11, Ch4F11 Chimeric), and an immunoglobulin light chain variable region comprising the amino acid sequence of SEQ ID NO:44 (Hu4F11 Kv2D-29);

(d) an immunoglobulin heavy chain variable region comprising the amino acid sequence of SEQ ID NO:34 (Sh4F11 Hv3-23), and an immunoglobulin light chain variable region comprising the amino acid sequence of SEQ ID NO:4 (4F11, Ch4F11 Chimeric);
(e) an immunoglobulin heavy chain variable region comprising the amino acid sequence of SEQ ID NO:34 (Sh4F11 Hv3-23), and an immunoglobulin light chain variable region comprising the amino acid sequence of SEQ ID NO:44 (Hu4F11 Kv2D-29);
(f) an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:46 (Hu4F11 Kv2D-29 N28H);
(g) an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:46 (Hu4F11 Kv2D-29 N28H);
(h) an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:46 (Hu4F11 Kv2D-29 N28H);
(i) an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:48 (Hu4F11 Kv2D-29 N28Q);
(j) an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:48 (Hu4F11 Kv2D-29 N28Q);
(k) an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:48 (Hu4F11 Kv2D-29 N28Q);
(l) an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:48 (Hu4F11 Kv2D-29 N28Q);
(m) an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:50 (Hu4F11 Kv2D-29 N28Y);
(n) an immunoglobulin heavy chain variable region comprising the amino acid sequence of SEQ ID NO:38 (Sh4F11 Hv3-23 S31H T62S), and an immunoglobulin light chain variable region comprising the amino acid sequence of SEQ ID NO:50 (Hu4F11 Kv2D-29 N28Y);
(o) an immunoglobulin heavy chain variable region comprising the amino acid sequence of SEQ ID NO:40 (Sh4F11 Hv3-23 A28T S31N T62S), and an immunoglobulin light chain variable region comprising the amino acid sequence of SEQ ID NO:50 (Hu4F11 Kv2D-29 N28Y); and
(p) an immunoglobulin heavy chain variable region comprising the amino acid sequence of SEQ ID NO:42 (Sh4F11 Hv3-23 A28T T62S), and an immunoglobulin light chain variable region comprising the amino acid sequence of SEQ ID NO:50 (Hu4F11 Kv2D-29 N28Y).

21. The isolated antibody of claim 20, wherein the antibody comprises an immunoglobulin heavy chain variable region comprising the amino acid sequence of SEQ ID NO:36 (Sh4F11 Hv3-23 A28T S31H T62S), and an immunoglobulin light chain variable region comprising the amino acid sequence of SEQ ID NO:46 (Hu4F11 Kv2D-29 N28H).

22. An isolated antibody that binds human Notch3 comprising an immunoglobulin heavy chain and an immunoglobulin light chain selected from the group consisting of:
(a) an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 90 (Hu4F11 Kv2D-29 N28H Kappa);
(b) an immunoglobulin heavy chain comprising the amino acid sequence of SEQ ID NO: 27 (4F11), and an immunoglobulin light chain comprising the amino acid sequence of SEQ ID NO: 29 (4F11);
(c) an immunoglobulin heavy chain comprising the amino acid sequence of SEQ ID NO: 74 (Ch4F11), and an immunoglobulin light chain comprising the amino acid sequence of SEQ ID NO: 86 (Ch4F11);
(d) an immunoglobulin heavy chain comprising the amino acid sequence of SEQ ID NO: 74 (Ch4F11), and an immunoglobulin light chain comprising the amino acid sequence of SEQ ID NO: 88 (Hu4F11 Kv2D-29);
(e) an immunoglobulin heavy chain comprising the amino acid sequence of SEQ ID NO: 76 (Sh4F11 Hv3-23), and an immunoglobulin light chain comprising the amino acid sequence of SEQ ID NO: 86 (Ch4F11);
(f) an immunoglobulin heavy chain comprising the amino acid sequence of SEQ ID NO: 76 (Sh4F11 Hv3-23), and an immunoglobulin light chain comprising the amino acid sequence of SEQ ID NO: 88 (Hu4F11 Kv2D-29);
(g) an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 90 (Hu4F11 Kv2D-29 N28H Kappa);
(h) an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 90 (Hu4F11 Kv2D-29 N28H Kappa);
(i) an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 90 (Hu4F11 Kv2D-29 N28H Kappa);
(j) an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 92 (Hu4F11 Kv2D-29 N28Q Kappa);
(k) an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 92 (Hu4F11 Kv2D-29 N28Q Kappa);
(l) an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 92 (Hu4F11 Kv2D-29 N28Q Kappa);

(m) an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 92 (Hu4F11 Kv2D-29 N28Q Kappa);

(n) an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 94 (Hu4F11 Kv2D-29 N28Y Kappa);

(o) an immunoglobulin heavy chain comprising the amino acid sequence of SEQ ID NO: 80 (Sh4F11 Hv3-23 S31H T62S), and an immunoglobulin light chain comprising the amino acid sequence of SEQ ID NO: 94 (Hu4F11 Kv2D-29 N28Y Kappa);

(p) an immunoglobulin heavy chain comprising the amino acid sequence of SEQ ID NO: 82 (Sh4F11 Hv3-23 A28T S31N T62S), and an immunoglobulin light chain comprising the amino acid sequence of SEQ ID NO: 94 (Hu4F11 Kv2D-29 N28Y Kappa); and (q) an immunoglobulin heavy chain comprising the amino acid sequence of SEQ ID NO: 84 (Sh4F11 Hv3-23 A28T T62S), and an immunoglobulin light chain comprising the amino acid sequence of SEQ ID NO: 94 (Hu4F11 Kv2D-29 N28Y Kappa).

23. The isolated antibody of claim 22, wherein the antibody comprises an immunoglobulin heavy chain comprising the amino acid sequence of SEQ ID NO: 78 (Sh4F11 Hv3-23 A28T S31H T62S), and an immunoglobulin light chain comprising the amino acid sequence of SEQ ID NO: 90 (Hu4F11 Kv2D-29 N28H Kappa).

* * * * *

UNITED STATES PATENT AND TRADEMARK OFFICE
CERTIFICATE OF CORRECTION

PATENT NO. : 9,879,083 B2  
APPLICATION NO. : 14/653684  
DATED : January 30, 2018  
INVENTOR(S) : Heidi Okamura et al.

Page 1 of 1

It is certified that error appears in the above-identified patent and that said Letters Patent is hereby corrected as shown below:

In Claim 8, at Column 171, Line 46, replace "vector of claim 6" with --vector of claim 7--.

Signed and Sealed this  
Twelfth Day of June, 2018

Andrei Iancu  
*Director of the United States Patent and Trademark Office*